US012357205B2

(12) United States Patent
Thomas et al.

(10) Patent No.: US 12,357,205 B2
(45) Date of Patent: *Jul. 15, 2025

(54) SYSTEMS AND METHODS FOR THE DETECTION AND QUANTIFICATION OF AMMONIA AND AMMONIUM IN FLUIDS

(71) Applicants: Mayo Foundation for Medical Education and Research, Rochester, MN (US); Arizona Board of Regents on behalf of Arizona State University, Scottsdale, AZ (US)

(72) Inventors: Marylaura Thomas, Scottsdale, AZ (US); Leslie Thomas, Scottsdale, AZ (US); Erica Forzani, Scottsdale, AZ (US)

(73) Assignees: Mayo Foundation for Medical Education and Research, Rochester, MN (US); Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/736,041

(22) Filed: Jun. 6, 2024

(65) Prior Publication Data

US 2024/0335146 A1    Oct. 10, 2024

Related U.S. Application Data

(63) Continuation of application No. 18/212,358, filed on Jun. 21, 2023, now Pat. No. 12,178,575, which is a (Continued)

(51) Int. Cl.
*A61B 5/1455* (2006.01)
*A61B 5/00* (2006.01)
(Continued)

(52) U.S. Cl.
CPC ...... *A61B 5/14552* (2013.01); *A61B 5/14546* (2013.01); *A61B 5/201* (2013.01);
(Continued)

(58) Field of Classification Search
CPC ... A61B 5/1455; A61B 5/14552; A61B 5/201; A61B 5/4866; B01D 53/228; B01D 2259/10
See application file for complete search history.

(56) References Cited

U.S. PATENT DOCUMENTS 3,926,734 A    12/1975  Gray et al.
11,793,431 B2  10/2023  Thomas et al.
(Continued)

FOREIGN PATENT DOCUMENTS

AU    2016255825 A1    11/2017
CN    102565040 A      7/2012
(Continued)

OTHER PUBLICATIONS

Aguilar et al., "Breath Ammonia Sensor Based on Conducting Polymer Nanojunctions," IEEE Sens. Journal, Feb. 2008, 8(3):269-273.
(Continued)

*Primary Examiner* — Eric F Winakur
(74) *Attorney, Agent, or Firm* — Fish & Richardson P.C.

(57) ABSTRACT

A system with an analyzer device in fluid communication with a sample of a bodily fluid is configured to chemically or electrochemically convert at least a portion of ammonium ($NH_4^+$) contained within the bodily fluid into ammonia ($NH_3$) and dispel the converted ammonia ($NH_3$) into a gas sensing chamber. An ammonia ($NH_3$) sensor located within the gas sensing chamber in conjunction with a processor can
(Continued)

quantify an amount of ammonia (NH$_3$) present in the gas sensing chamber in relation to the total ammonia of the bodily fluid.

12 Claims, 40 Drawing Sheets

Related U.S. Application Data continuation of application No. 16/959,551, filed as application No. PCT/US2019/013237 on Jan. 11, 2019, now Pat. No. 11,793,431.

(60) Provisional application No. 62/617,053, filed on Jan. 12, 2018.

(51) Int. Cl.
  *A61B 5/145* (2006.01)
  *A61B 5/20* (2006.01)
  *B01D 53/22* (2006.01)

(52) U.S. Cl.
  CPC .......... *A61B 5/4866* (2013.01); *B01D 53/228* (2013.01); *B01D 2259/10* (2013.01)

(56) References Cited

U.S. PATENT DOCUMENTS

| | | |
|---|---|---|
| 12,178,575 B2 | 12/2024 | Thomas et al. |
| 2003/0113931 A1 | 6/2003 | Pan et al. |
| 2003/0113932 A1 | 6/2003 | Sternberg et al. |
| 2007/0083094 A1 | 4/2007 | Colburn et al. |
| 2008/0041136 A1 | 2/2008 | Kopelman et al. |
| 2009/0312726 A1 | 12/2009 | Kim |
| 2010/0184198 A1 | 7/2010 | Joseph et al. |
| 2012/0309048 A1 | 12/2012 | Ratcliffe et al. |
| 2014/0263061 A1 | 9/2014 | Taylor et al. |
| 2015/0226702 A1 | 8/2015 | Veltman et al. |
| 2015/0343372 A1 | 12/2015 | Marei et al. |
| 2016/0074567 A1 | 3/2016 | Giordano et al. |
| 2016/0231310 A1 | 8/2016 | Ayyub et al. |
| 2021/0076999 A1 | 3/2021 | Thomas et al. |
| 2023/0329596 A1 | 10/2023 | Thomas et al. |

FOREIGN PATENT DOCUMENTS

| | | |
|---|---|---|
| CN | 105940300 A | 9/2016 |
| EP | 0481436 A1 | 4/1992 |
| EP | 0525550 A1 | 2/1993 |
| JP | S5877663 A | 5/1983 |
| JP | S58193459 A | 11/1983 |
| JP | 2000146899 A | 5/2000 |
| JP | 2006084398 A | 3/2006 |
| JP | 2010038666 A | 2/2010 |
| JP | 2016529515 A | 9/2016 |
| JP | 2017530773 A | 10/2017 |
| WO | WO 2007089571 A2 | 8/2007 |
| WO | WO 2016176366 A1 | 11/2016 |

OTHER PUBLICATIONS

Airoudj et al., "A new evanescent wave ammonia sensor based on polyaniline composite," Talanta, Jul. 2008, 76(2):314-319.
Airoudj et al., "New sensitive layer based on pulsed plasma-polymerized aniline for integrated optical ammonia sensor," Anal. Chim. Acta, Sep. 2008, 626(1):44-52.
biovision.com [online], "Ammonium Colorimetric Assay Kit," available on or before Feb. 2, 2017, via Internet Archive: Wayback Machine URL<https://www.biovision.com/ammonia-colorimetric-assay-kit.html>, retrieved on Dec. 31, 2020, retrieved from URL<http://www.biovision.com/ammonia-colorimetric-assay-kit.html>, 2 pages.
Clifford et al., "Characteristics of Semiconductor Gas Sensors I. Steady State Gas Response," Sens. Actuators, Jan. 1982, 3:233-254.
craigmedical.com [online], "Professional Urinalysis Reagent Test Strips," available on or before Apr. 3, 2002, via Internet Archive: Wayback Machine URL<https://web.archive.org/web/20020403024137/http://craigmedical.com/urine_diagnostics.htm>, retrieved on Dec. 31, 2020, retrieved from URL<http://craigmedical.com/urine_diagnostics.htm>, 3 pages.
Da Fonseca-Wollheim, "Enzymatic assay based on 2-oxoglutarate with glutamate dehydrogenase for detection of ammonia in biological samples (Direkte Plasmaarnmoniakbestimmung ohne Enteiweissung)," J. Clin. Chem. Clin. Biochemistry, 1973, 11:421-431 (with English abstract).
Davies et al., "Quantitative analysis of ammonia on the breath of patients in end-stage renal failure," Kidney International, Jul. 1997, 52(1):223-228.
Filho et al., "Ammonia detection by using quantum-cascade laser photoacoustic spectroscopy," Appl. Optics, Jul. 2006, 45(20):4966-4971.
Filho et al., "Detection of ammonia released from zeolite by the quantum cascade laser based photoacoustic set-up," Eur. Phys. J. Spec. Topics, Jan. 2008, 153:547-550.
Georges, "Determination of Ammonia and Urea in Urine and of Urea in Blood by Use of an Ammonia-Selective Electrode," Clin. Chemistry, Nov. 1979, 25(11):1888-1890.
Grote et al., "Solid-Phase Microextraction for the Analysis of Human Breath," Anal. Chemistry, Feb. 1997, 69(4):587-596.
Hibbard, "Breath ammonia analysis: Clinical application and measurement," Crit. Rev. Anal. Chemistry, Jan. 2011, 41(1):21-35.
Hübner et al., "Tin Oxide Gas Sensors: an Analytical Comparison of Gas-sensitive and Non-gas-sensitive Thin Films," Sens. Actuators B Chemical, Jun. 1991, 4(3-4):463-466.
Imawan et al., "Gas-sensing characteristics of modified-MoO3 thin films using Ti-overlayers for NH3 gas sensors," Sens. Actuators B Chemical, Jun. 2000, 64(1-3):193-197.
International Preliminary Report on Patentability in International Appln. No. PCT/US2019/013237 mailed on Jul. 14, 2020, 8 pages.
International Search Report and Written Opinion in International Appln. No. PCT/US2019/013237 mailed on Apr. 22, 2019, 10 pages.
Jayawardane et al., "Development of a gas-diffusion microfluidic paper-based analytical device (uPAD) for the determination of ammonia in wastewater samples," Anal. Chemistry, May 2015, 87(9):4621-4626.
Ji et al., "Electrochemical Ammonia Gas Sensing in Nonaqueous Systems: A Comparison of Propylene Carbonate with Room Temperature Ionic Liquids," Electroanalysis, Nov. 2007, 19(21):2194-2201.
Kharat et al., "Synthesis of polypyrrole films for the development of ammonia sensor," Polym. Adv. Technologies, May 2007, 18(5):397-402.
Krkosova et al., "Temperature-programmed gas chromatography linear retention indices of all C-4-C-30 monomethylalkanes on methylsilicone OV-1 stationary phase—Contribution towards a better understanding of volatile organic compounds in exhaled breath," J. Chromatography A, Jan. 2008, 1179(1):59-68.
Kukla et al., "Ammonia sensors based on sensitive polyaniline films," Sens. Actuators B Chemical, Dec. 1996, 37(3):135-140.
Lahdesmaki et al., "A polypyrrole-based amperometric ammonia sensor," Talanta, Jan. 1996, 43(1):125-134.
Lahdesmaki et al., "Interferences in a polypyrrole-based amperometric ammonia sensor," Talanta, Jun. 2000, 52(2):269-275.
Manne et al., "Pulsed quantum cascade laser-based cavity ring-down spectroscopy for ammonia detection in breath," Appl. Optics, Dec. 2006, 45(36):9230-9237.
Passaro et al., "Ammonia Optical Sensing by Microring Resonators," Sensors, Nov. 2007, 7(11):2741-2749.
pranalytica.com [online], "Pranalytica: World leading designer and manufacturer of high power midwave Infrared and longwave Infrared Quantum Cascade Lasers for defense, homeland security and commercial applications and sensor systems," available on or before Nov. 28, 2001, via Internet Archive: Wayback Machine URL<https://web.archive.org/web/20011128185803/http://www.

(56) References Cited

OTHER PUBLICATIONS pranalytica.com/>, retrieved on Dec. 31, 2020, retrieved from URL<http://www.pranalytica.com/>, 1 page.
Prasad et al., "Ammonia sensing characteristics of thin film based on polyelectrolyte templated polyaniline," Sens. Actuators B Chemical, May 2005, 106(2):626-631.
preclaboratories.com [online], "Ammonia Test Strips," upon information and belief, available no later than Jan. 12, 2018, retrieved on Dec. 31, 2020, retrieved from URL<https://preclaboratories.com/product/ammonia-test-strips/>, 3 pages.
Sberveglieri, "Recent Developments in Semiconducting Thin-Film Gas Sensors," Sens. Actuators B Chemical, 1995, 23(2-3):103-109.
Smith et al., "A comparative study of the analysis of human urine headspace using gas chromatography-mass spectrometry," J. Breath Research, Sep. 2008, 2(3):037022, 10 pages.
Spanel et al., "Progress in SIFT-MS: Breath Analysis and Other Applications," Mass Spectrom. Reviews, Mar. 2011, 30(2)236-267.
Spanel et al., "Quantification of Ammonia in Human Breath by the Selected Ion Flow Tube Analytical Method Using H30+ and O2 Precursor Ions," Rapid Commun. Mass Spectrometry, Jun. 1998, 12(12):763-766.
Srivastava et al, "Sensing mechanism in tin oxide-based thick-film gas sensors," Sens. Actuators B Chemical, Sep. 1994, 21(3):213-218.
Sutar et al., "Preparation of nanofibrous polyaniline films and their application as ammonia gas sensor," Sens. Actuators B Chemical, Dec. 2007, 128(1):286-292.
Timmer et al., "Ammonia sensors and their applications—a review," Sens. Actuators B Chemical, Jun. 2005, 107(2):666-677.
Toda et al., "Measurement of Ammonia in Human Breath with a Liquid-Film Conductivity Sensor," Anal. Chemistry, Oct. 2006, 78(20):7284-7291.
Turner et al., "A longitudinal study of ammonia, acetone and propanol in the exhaled breath of 30 subjects using selected ion flow tube mass spectrometry, SIFT-MS," Physiol. Measurement, Feb. 2006, 27:321-337.
Vallet et al., "Urinary ammonia and long-term outcomes in chronic kidney disease," Kidney Int., Jul. 2015, 88(1):137-145.
Wang et al., "Analysis of breath, exhaled via the mouth and nose, and the air of oral cavity," J. Breath Research, Sep. 2008, 2(3):037013, 13 pages.

SYSTEMS AND METHODS FOR THE DETECTION AND QUANTIFICATION OF AMMONIA AND AMMONIUM IN FLUIDS

CROSS-REFERENCE TO RELATED APPLICATIONS

This application is a continuation application of U.S. application Ser. No. 18/212,358, filed Jun. 21, 2023, which is a continuation application of U.S. application Ser. No. 16/959,551, filed Jul. 1, 2020 (now U.S. Pat. No. 11,793,431), which is a National Stage application under 35 U.S.C. § 371 of International Application No. PCT/US2019/013237, having an International Filing Date of Jan. 11, 2019, which claims priority to U.S. Provisional Application Ser. No. 62/617,053, filed Jan. 12, 2018. The disclosure of the prior applications are considered part of (and are incorporated by reference in) the disclosure of this application.

FIELD OF THE INVENTION

The present invention is directed to systems and methods for the detection and quantification of "total ammonia" (defined herein as the sum of ammonia ($NH_3$) and ammonium ($NH_4^+$)).

BACKGROUND

Hospital-acquired acute kidney injury (AKI) is a significant health care problem that may impact up to 30% of children and 20% of adults in the hospital setting. AKI is associated with increased mortality and may result in chronic kidney disease (CKD) which is strongly correlated with future hospitalizations, cardiovascular events, and shortened life-expectancy.

In most cases, hospital-acquired AKI is exceedingly difficult to diagnose quickly (i.e., within minutes or hours) because the symptoms and signs of AKI are generally not apparent as AKI begins to occur. Accordingly, medical care for AKI is stunted because of under and delayed recognition of AKI. Furthermore, the "diagnostic hallmarks" of AKI (i.e., elevated serum creatinine concentration, decreased rate of urine output) are in actuality quite poor markers of early kidney tissue distress or early AKI (nascent AKI) because they do not necessarily change rapidly and may lag well behind (hours or days) the first moments of nascent AKI. Also, changes in serum creatinine or urine output are not specific for AKI. Indeed, the serum creatinine level may rise and the rate of urine output may fall (without kidney tissue injury actually occurring) in many commonly encountered clinical scenarios (e.g., decreased oral fluid intake, gastrointestinal fluid losses, transdermal fluid losses) in which blood perfusion to the kidney tissue ("effective circulating volume") is decreased sufficiently. The adaptive response to decreased effective circulating volume includes decreased kidney glomerular filtration rate (which leads to decreased creatinine clearance and increased serum creatinine) and increased kidney water recovery within the kidney's collecting tubules as a response to increased circulating levels of antidiuretic hormone (which leads to the production of a more concentrated urine and decreased urine output). Serum creatinine levels may also be impacted significantly by the administration of certain drugs without kidney tissue injury actually being present. These drugs include cimetidine, trimethoprim, pyrimethamine, salicylates, phenacemide, corticosteroids, and some vitamin D derivatives. The use of angiotensin converting enzyme inhibitors, angiotension II receptor blockers, and diuretics also influence creatinine clearance (and thus serum creatinine levels) without causing AKI. Accordingly, improving the diagnostic process to recognize nascent AKI in the hospitalized patient is an unmet clinical need.

There is intense interest in discovering and validating novel AKI detecting methods. Conventional AKI detection methods may include the serial testing of lagging blood markers (i.e., creatinine) and the monitoring of urine flow rates (i.e., urine volume output per hour). Exposing a patient to serial blood draws to monitor for changes in serum creatinine is inherently problematic, as each sample taken necessarily involves the removal of that body tissue. In addition to its lagging nature and lack of specificity for AKI, a serum creatinine level that has significantly changed as a result of AKI is indicative of tissue damage and global organ dysfunction rather than early kidney tissue cellular distress. Novel urine biomarkers for AKI (including neutrophil gelatinase-associated lipocalin (NGAL), kidney injury molecule-1 (KIM-1), insulin like growth factor binding protein 7 (IGFBP7), and tissue inhibitor of metalloproteinases 2 (TIMP2)) correlate with AKI (as defined by the traditional hallmark markers) and may change more rapidly than serum creatinine, but share the same limitation as creatinine in being relatively delayed (i.e., they change hours rather than minutes after kidney injury has occurred). Furthermore, novel urine AKI biomarkers perform more poorly in predicting and/or diagnosing AKI in patients with certain health conditions, including chronic kidney disease (CKD) and sepsis. Considering further that the discrimination of whether a specific episode of AKI may or may not be best treated by quick application of maneuvers to augment effective circulating volume is of critical clinical significance in many cases, the inherent inability of each and every standard and novel AKI laboratory test to aid in that determination also limits their overall usefulness in the health care setting. Accordingly, there is a need for AKI detection systems and methods that are capable of rapidly detecting at risk kidney tissue, kidney tissue distress, and/or nascent AKI prior to the occurrence of significant kidney tissue damage (AKI).

To that end, urine "total ammonia" (ammonia ($NH_3$) and ammonium ($NH_4^+$)) can be used as a novel urine biomarker for the rapid detection of at risk kidney tissue, kidney tissue distress, nascent AKI, and/or AKI. In fluids, ammonia ($NH_3$) and ammonium ($NH_4^+$) exist in equilibrium with each other, and the amount of each species is dependent upon the surrounding environmental conditions (e.g., pH, temperature, pressure). The renal production of total ammonia (renal ammoniagenesis) mainly depends upon the metabolism of glutamine within the renal proximal tubular cells in addition to other intrarenal conditions. Renal ammoniagenesis normally changes or adapts in response to various systemic conditions, including systemic acid/base status, potassium status, and with fluctuations in dietary protein intake. Changing levels of systemic total ammonia, such as with changes in hepatic function, also lead to alterations in the urine total ammonia level. A reduced effective circulating volume and/or AKI quickly impact renal ammoniagenesis, decrease urine total ammonia content, and decrease the total ammonia excreted by the kidney tissue. Therefore, continuous, automated, prospective monitoring for dynamic changes in the urine total ammonia concentration and/or content can be used to rapidly detect an underlying change in renal blood flow (effective circulating volume), at risk kidney tissue, kidney cellular distress, nascent AKI, and/or AKI. Additionally, continuous, automated monitoring for dynamic changes (increasing or decreasing levels) in the urine total ammonia can be used to detect underlying changes in any systemic condition that impacts renal ammoniagenesis and/or urine total ammonia, including systemic acid/base status, potassium status, dietary protein intake, and liver function status.

Accordingly, there is a need for systems and methods that allow for the continuous, automated monitoring of changes in the quantity of total ammonia (ammonia ($NH_3$) and ammonium ($NH_4^+$)) in fluids, including those excreted from the body (i.e., urine).

Conventional systems and methods for ammonia ($NH_3$) and ammonium ($NH_4^+$) measurement are often inaccurate, difficult to use, cumbersome, and neither amenable to bedside urine testing nor continuous monitoring. Conventional systems for ammonia or ammonium measurement include: (1) colorimetric sensors, (2) spectroscopic based sensors, (3) nanomaterial based sensors, (4) contactless conductivity based sensors, and (5) reagent sticks.

Colorimetric sensors are used for measurement of ammonia ($NH_3$) and/or ammonium ($NH_4^+$) in wastewater and blood. This type of sensor consists of a thin membrane embedded with an ammonia ($NH_3$)-sensitive pH dye attached to the end of a detection unit (e.g. optic fiber). These devices possess high sensitivity, but further instrumental improvements are required for use with biological samples.

For example, the blood analytic techniques in a ROCHE COBAS INTEGRA® are based on an enzymatic method requiring the use of two reagents and analysis within thirty minutes of blood sample collection. This method used for blood analysis is not directly applicable to measurement of urine. When used for urine, the urine (milli-molar urine total ammonia concentration) must be diluted by at least a factor of 10 to 1000 to achieve a concentration that is within the limits of the blood analytic technique (micro-molar blood total ammonia concentration). Thus, the blood analytic technique is not amenable to bedside urine testing.

In another example, a hand-held portable device may detect levels of ammonium ($NH_4^+$) in blood. The hand-held portable device may use a color-based sensor and a partition membrane that converts ammonium ($NH_4^+$) into ammonia ($NH_3$). However, the hand-held device may be single use, provide only a one point in time measure of ammonium ($NH_4^+$), and may not be amenable to continuous, automated, or repeated measures. Additionally, the described hand-held portable device may be used with blood, which requires invasive blood sampling and makes assessment more difficult and cumbersome if continuous monitoring of a patient is desired. Moreover, as the described hand-held portable device is used with blood, it may not be adaptable for use outside of a medical setting (i.e., in a patient's home). Furthermore, the device does not provide continuous quantification for at least 24 hours, which is needed for monitoring critical clinical conditions. Additionally, conventional hand-held portable devices have demonstrated inadequate accuracy and are prone to both false positive and false negative test results.

Conventional methods for detecting ammonium ($NH_4^+$) or ammonia ($NH_3$) in samples may also include laboratory-based methods with manual or pump-based handling of liquids and samples, and external detection instruments such as scanners or optical fiber with a photomultiplier tube. These conventional systems may use a paper-based extraction membrane or solution mixtures for analysis of ammonium ($NH_4^+$) or ammonia ($NH_3$) in water, or pure samples. The laboratory based methods are not able to accurately detect ammonium ($NH_4^+$) or ammonia ($NH_3$) levels from a sample of a complex body fluid that contains highly variable quantities of other dissolved components (i.e., urine).

Additionally, semi-continuous measurement of ammonium ($NH_4^+$)/ammonia ($NH_3$) performed in water quality monitoring applications with commercial technologies based on amperometric or colorimetric sensors are not adaptable for medical settings. For example, the ANALYTICAL TECHNOLOGY Q45N device weighs 15 pounds and converts ammonium ($NH_4^+$)/ammonia ($NH_3$) in solution to a stable monochloramine that is measured with an amperometric sensor. It requires a minimum flow rate of 200 mL/min (Note: Minimum or obligate urine volume for humans is 0.5 mL/Kg/hr. For adult humans, typical urine output is 800-2000 mL/day (0.6-1.4 mL/min).) and is reliable in the range of 0-5 ppm $NH_3$ (0-270 micro-molar). The AZTEC 600 colorimetric analyzer (ABB) is designed for semi-continuous use in wastewater. It can only measure four samples per hour using indophenol blue chemistry, and it requires continuous flow rates of 200-500 mL/min. It measures up to 3 ppm ammonia ($NH_3$). The AWA INSTRUMENTS CX4000 also operates on a colorimetric principle. These large-commercial semi-continuous measurement devices from the water treatment industry are not readily adaptable for use in a medical setting, and the sensors those devices utilize must regularly be calibrated for different concentration ranges. Batch-measurement of ammonium ($NH_4^+$)/ammonia ($NH_3$) in aqueous solutions is commonly done in water treatment applications through either an ammonium ion probe or a colorimeter coupled with a spectrophotometer.

Ammonium ($NH_4^+$) ion selective electrodes (either solid state or membrane-based) operate based on the principle of a membrane with an ammonium ($NH_4^+$) selective ion exchanger which results in different potentials across the membrane comparing an unknown solution to a reference solution. Most ammonium ($NH_4^+$) colorimetric methods involve adding reagents to a water sample and evaluating the color of the liquid solutions with a specialized instrument. A few ammonium ($NH_4^+$) colorimetric tests involve strips (similar to pH measurement strips) in which a reagent is added to a solution, the strip is dipped into the solution, and a color change is visually observed. Commercially available batch-measurement products require use of reagents, enzymes, and or large analytical equipment. The Roche enzymatic method requires a minimum sample volume of 20 μL and is not designed for urine. The ammonium ($NH_4^+$) selective electrodes for aqueous solutions require minimum sample volumes of few milliliters and the electrode must be calibrated every 1-2 hours (in continuous measurement). To be accurate, the electrodes also must be calibrated with different solutions depending on the expected concentration range of ammonium ($NH_4^+$) in the solution being measured.

Most measurement techniques for ammonium ($NH_4^+$)/ammonia (NH3) detection in human samples rely on breath or blood (plasma). However, the conventional techniques are not appropriate for continuous monitoring as the ion selective electrodes require time-consuming calibration between analysis of each sample because of the limited stability of sensing membranes and drift in measurement output. For example, the ORION™ High-Performance Ammonium ($NH_4^+$) Electrode needs to be calibrated prior to each new measurement to minimize measurement drift because of the limited stability of sensing membranes.

Furthermore, given the complexity of biological samples, few methodologies have been approved by the United States Food and Drug Administration (FDA) for clinical research. For ammonium ($NH_4^+$) detection in blood and urine, enzymatic assays are the only technique that meets the FDA's standards. In general, enzymatic assays have limited storage lifetime, involve multiple incubation steps, require processing times greater than one hour, and involve significant operator labor.

Spectroscopic methods of ammonia gas ($NH_3$) measurement include pulsed quantum cascade laser spectroscopy and optical micro-ring resonators. While large (table-top) measurement systems exist, these lack the small size, low weight, and low cost desirable for portable individual monitoring (such as at a hospital bedside). For example, ammonia ($NH_3$) may be detected via absorption spectroscopy by instruments such as NEPHROLUX™, which uses a tunable laser and an acoustic detector to perform sub-parts per billion (ppb) zero background measurements of ammonia ($NH_3$) in the presence of interferents like carbon dioxide and water vapor (such as in breath). While spectroscopic techniques are extremely sensitive, they usually have bulky components making them inconvenient for personalized use. Moreover, optical components in absorption spectroscopy are prone to misalignments and unsuitable for personalized use.

Gas chromatography—mass spectrometry (GC—MS) and selective ion flow tube—mass spectrometry (SIFT—MS) may be accurate for ammonia ($NH_3$) measurement but are expensive, and instruments are difficult to maintain. GC-MS separates and identifies both ammonia ($NH_3$) and ammonium ($NH_4^+$) from complex mixtures, but requires expensive instrumentation (~$300,000) and pre-concentration steps that preclude high reproducibility and real-time implementation. SIFT-MS was developed for real-time detection of low molecular weight volatiles, including ammonia ($NH_3$), in different biological samples (skin and urine headspace, breath, etc.) but is also expensive (~$200,000) and rather difficult to maintain.

Nanomaterial based chemiresistors and electrochemical sensors exhibit detection limits matching the clinically relevant ammonia ($NH_3$) levels (breath-ammonia ($NH_3$) in ppb) under well-defined, near ideal laboratory conditions. However, detection of ammonia ($NH_3$) in complex samples using these sensors requires further improvement to obtain the selectivity and lifetime necessary for continuous monitoring conditions.

Additionally, conventional ammonia ($NH_3$) detectors may include a contactless conductivity based sensor. However, the acid solution used in a conventional contactless conductivity based ammonia ($NH_3$) sensor requires replacement after each measurement, making continuous measurement impractical.

Lastly, although urine reagent sticks are in wide clinical use to determine 10 different urine parameters (including pH, specific gravity, leukocyte esterase, nitrite, urobilinogen, protein, hemoglobin, glucose, ketones, bilirubin), commercial electronic readers of these urine dipsticks do not include measurements of ammonia ($NH_3$) or ammonium ($NH_4^+$). However, ammonium ($NH_4^+$) detection reagent sticks are commercialized for use in water samples. The operation of these ammonium ($NH_4^+$)—detection reagent sticks is based on irreversible chemical reactions, and therefore they are single-use devices. Although these reagent sticks are quick and easy to use, they only provide a semi-quantitative assessment of parameters, and do not demonstrate the accuracy and continuous real-time monitoring capability desired in critical applications.

Additionally, because ammonia ($NH_3$) and ammonium ($NH_4^+$) in biological solutions are in equilibrium with each other and because each species will spontaneously convert to the other depending on changes in local conditions (i.e., pH, temperature, pressure) within the biological sample being tested, there is a need for systems and methods to detect and quantify total ammonia (ammonia ($NH_3$) and ammonium ($NH_4^+$)) within a biological sample (e.g., bodily fluid, urine) in the medical field that also accounts for the presence of both ammonia ($NH_3$) and ammonium ($NH_4^+$) in the sample being tested.

Accordingly, there is a need for systems and methods that allow for the continuous, automated monitoring in changes in the concentration and/or quantity of ammonia ($NH_3$) in bodily fluids that also takes into account the presence of ammonium ($NH_4^+$) in the bodily fluid.

SUMMARY

This disclosure describes systems and methods related to the detection of total ammonia (ammonia ($NH_3$) and ammonium ($NH_4^+$)) in fluids.

In some embodiments, the systems and methods described herein may convert ammonium ($NH_4^+$) to ammonia ($NH_3$). Depending on the pH, bodily samples such as urine may contain variable amounts of ammonia ($NH_3$) and ammonium ($NH_4^+$). The systems and methods described herein are capable of extracting ammonia ($NH_3$) from the biological fluid (e.g., urine, sweat, blood, etc.) via an extraction membrane so that virtually the entire sum of ammonia ($NH_3$) and ammonium ($NH_4^+$) contained within the biological sample is measured as ammonia ($NH_3$). In some embodiments, this may allow sequential samples of a fluid (e.g., urine, as it is produced) to be sequentially and near continuously measured for total ammonia (ammonia ($NH_3$) and ammonium ($NH_4^+$)) concentration. The extraction membrane may convert virtually all of the fluid sample's ammonium ($NH_4^+$) to ammonia ($NH_3$) chemically or electrochemically.

In some embodiments, a system includes an analyzer device. The analyzer device may be in fluid communication with a sample of a bodily fluid. The analyzer device may include an intelligent-controlled sample conditioning and delivery system, an extraction membrane (which converts virtually all of the fluid sample's ammonium ($NH_4^+$) to ammonia ($NH_3$)), a sensing chamber, and an ammonia ($NH_3$) sensor. The intelligent-controlled sample conditioning and delivery system may control the amount of bodily fluid that becomes in contact with the extraction membrane so that the sensor performance remains unaltered for multiple continuous uses and long periods of time. The sample conditioning and delivery system may be operated by an intelligently programmable valve system based on an intelligent algorithm, including sample volume, time, and sensor signal change information.

In some embodiments, the sample conditioning and delivery system may include a signal saturation and drift avoidance mechanism that includes a micro-controlled actuated valve system. The micro-controlled actuated valve system may control the volume of bodily fluid that is in contact with the analyzer device. The micro-controlled actuated valve system may have a valve that is configured to control the delivery of bodily fluid, headspace gas, and gas from a zeroing channel. The sample conditioning and delivery system may be formed at least by two inlets: a sampling channel in contact with a bodily fluid, and a purging channel in contact with a zeroing material that allows the system to record a baseline. The baseline may be essential to correct drift of sensor signals. The extraction membrane may be located between an area in fluid communication with the bodily fluid and the sensing chamber, and it may be configured to 1) convert at least a portion of ammonium ($NH_4^+$) contained within the bodily fluid into ammonia ($NH_3$) and 2) dispel the converted ammonia ($NH_3$) into the sensing chamber. An ammonia ($NH_3$) sensor located within the sensing chamber may be pretreated with heat under specific conditions, and may include a pre-calibration algorithm to assure performance of the sensor under a broad range of temperature, relative humidity, and pressure conditions. The ammonia ($NH_3$) sensor processor may include non-transitory memory storing instructions that, when executed, cause the processor to quantify an amount of ammonia ($NH_3$) present in the sensing chamber. The analyzer device may detect, based on the quantified amount of ammonia ($NH_3$) present in the sensing chamber and how that amount may change over time, alterations in organ or tissue function, the occurrence of organ or tissue damage, changes in systemic biological total ammonia (ammonia ($NH_3$) and ammonium ($NH_4^+$)) physiology, or other bodily processes in which body fluid total ammonia (ammonia ($NH_3$) and ammonium ($NH_4^+$)) levels change. Optionally, the system may also include a user interface device. In some embodiments, the ammonia ($NH_3$) sensor may be further configured to transmit the quantified amount of ammonia ($NH_3$) present in the sensing chamber to the user interface device. In some embodiments, the user interface device may be configured to receive at least transmission from the analyzer device, and include a display with a graphical user interface that is configured to display the received transmission from the analyzer device.

In some embodiments, a method may receive, at an analyzer device, a sample of a bodily fluid; convert, via an extraction membrane located between an area in fluid communication with the sample of bodily fluid and a sensing chamber of the analyzer device, at least a portion of ammonium ($NH_4^+$) contained within the sample of bodily fluid into ammonia ($NH_3$); dispel, via the extraction membrane, the converted ammonia ($NH_3$) into the sensing chamber; determine, via an ammonia ($NH_3$) sensor located within the sensing chamber, an amount of ammonia ($NH_3$) present in the sensing chamber; and detect altered organ or tissue function, organ or tissue damage, changes in physiology affecting body fluid total ammonia concentration, or other bodily processes in which body fluid total ammonia levels change, if the determined amount of ammonia ($NH_3$) present in the sensing chamber changes or is interpreted to be outside the normal or expected concentration or range for the individual at the time of measurement. Optionally, the method may further include transmitting to a user interface device, the amount of ammonia ($NH_3$) present in the sensing chamber, where the user interface device further includes a display having a graphical user interface. Optionally, the method may also include receiving, at the user interface device, the amount of ammonia ($NH_3$) present in the sensing chamber; and displaying, via the graphical user interface, the amount of ammonia ($NH_3$) present in the sensing chamber.

In some embodiments, a method of determining kidney function includes the step of detecting a level of total ammonia (ammonia ($NH_3$) and ammonium ($NH_4^+$)) in a subject sample on a first analyzer device. The analyzer device may then transmit the detected level of total ammonia (ammonia ($NH_3$) and ammonium ($NH_4^+$)) to a second user interface device. The second user interface device may then correlate the detected level of total ammonia (ammonia ($NH_3$) and ammonium ($NH_4^+$)) in a subject sample with a diagnosis of altered kidney function. The correlation may take into account the detected level of total ammonia (ammonia ($NH_3$) and ammonium ($NH_4^+$)) in a subject sample as compared to the detected level of total ammonia (ammonia ($NH_3$) and ammonium ($NH_4^+$)) in a normal subject or the detected level of total ammonia (ammonia ($NH_3$) and ammonium ($NH_4^+$)) in a prior sample of the subject.

In some embodiments, a non-invasive device may semi-continuously detect a fluid's concentration of total ammonia (ammonia ($NH_3$) and ammonium ($NH_4^+$)). The non-invasive device may be miniaturized, be able to be conveniently positioned, and be able to transmit data automatically to provide near real-time and/or semi-continuous analysis. In some embodiments, the device may be used for the automated monitoring and rapid detection of acute kidney injury (AKI) in hospitalized patients with an indwelling urinary catheter. Alternatively, the device may be used for the detection of changes in renal ammoniagenesis and/or urine total ammonia (ammonia ($NH_3$) and ammonium ($NH_4^+$)) due to 1) changes in kidney function, 2) acute kidney injury or failure, 3) chronic kidney disease, 4) changes in liver function, 5) acute liver injury or failure, 6) chronic liver disease (e.g., cirrhosis), 7) acute gastrointestinal bleeding, 8) chronic gastrointestinal bleeding, 9) genetic or inherited metabolic diseases involving or impacting aspects of ammonia physiology including its generation, handling, and/or excretion (e.g., urea cycle disorders, organic acidurias, carnitine deficiency from defects in fatty acid oxidation, dibasic aminoaciduria, and defects in pyruvate metabolism), 10) variations of normal metabolic processes (e.g., increased ammonia generation and excretion following a protein meal), 11) acute or chronic systemic acid/base changes or imbalances due to metabolic processes or disease states, 12) acute or chronic systemic acid/base changes or imbalances due to respiratory processes or disease states, 13) altered effective circulating volume, 14) altered renal blood flow, or 15) renal plasma flow.

DETAILED DESCRIPTION

Figure 1:
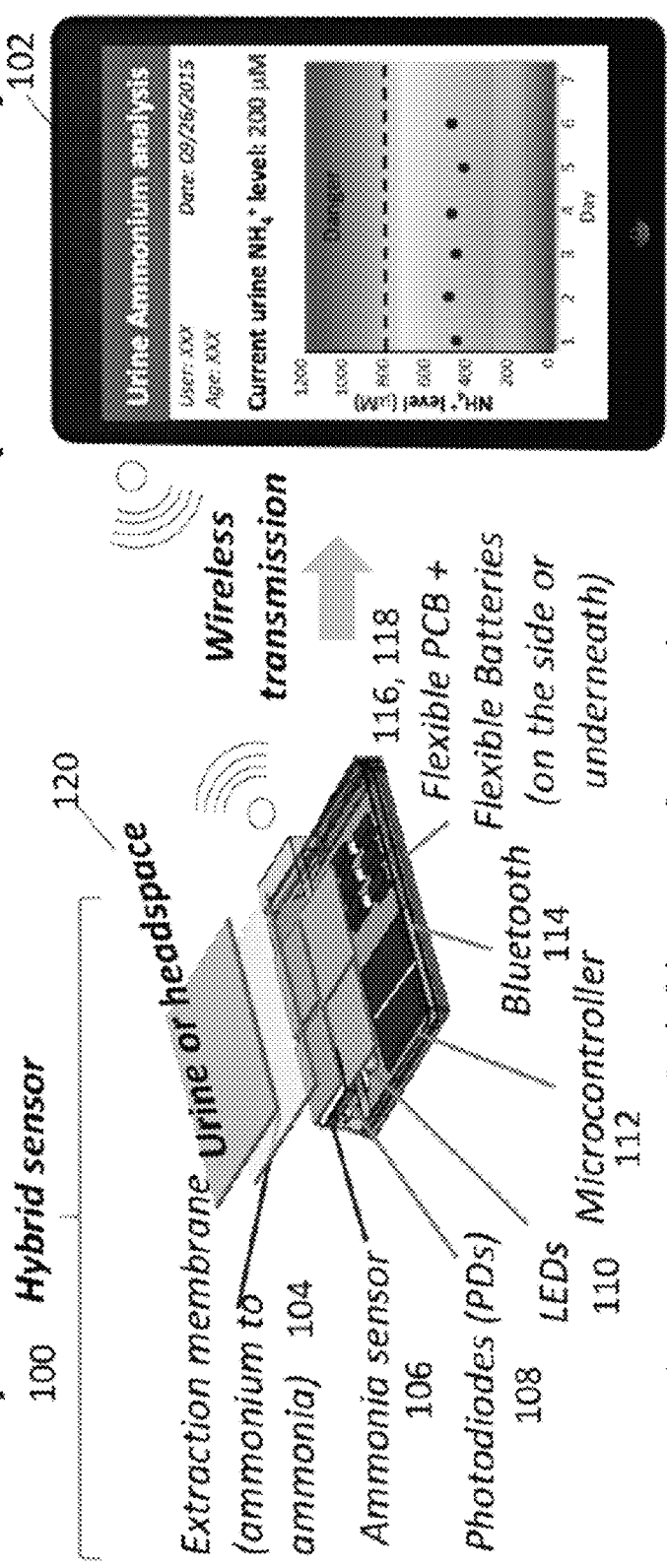
FIG. 1 illustrates a schematic diagram of an analyzer to determine a fluid's total ammonia according to an aspect of the present disclosure.
Figure 1:
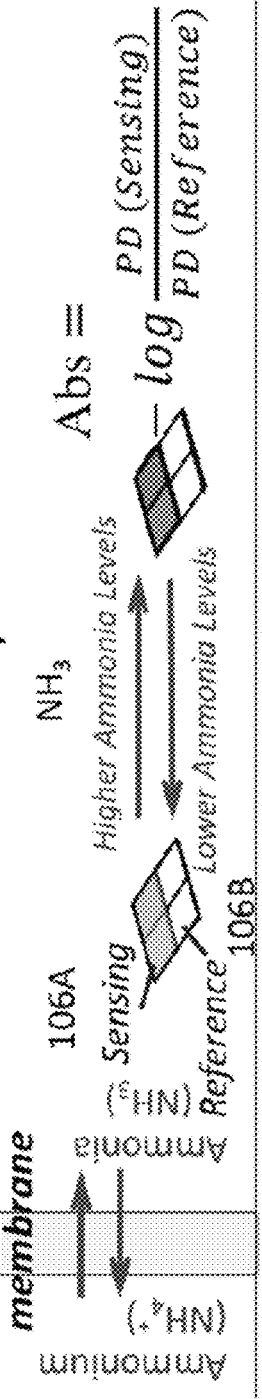
Figure 1:
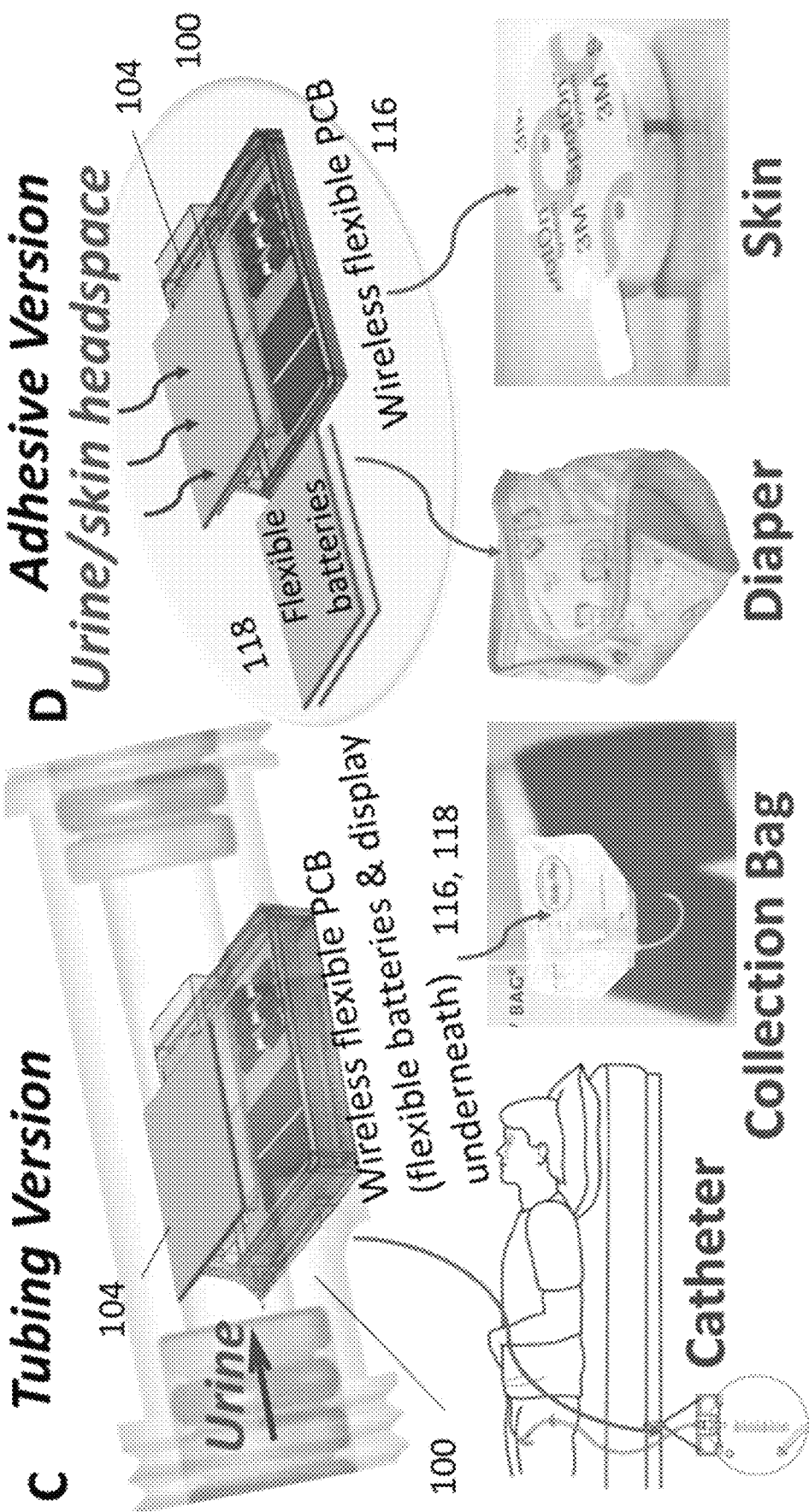

Some embodiments of the systems and methods described herein include a continuous total ammonia (ammonia ($NH_3$) and ammonium ($NH_4^+$)) sensing and quantification device that is wireless, solid-state, and portable. In addition to other potential applications, health care providers may be able to use the systems, methods, and apparatus described herein to reliably measure total ammonia (ammonia ($NH_3$) and ammonium ($NH_4^+$)) in biological samples faster and more accurately than previously possible with conventional systems. In some embodiments, the systems, methods, and apparatus described herein may be able to determine the precise concentration of total ammonia (ammonia ($NH_3$) and ammonium ($NH_4^+$)) contained in a biological sample within five seconds and to wirelessly transmit data to other devices. In some embodiments, the wireless transmission may be performed using Bluetooth®. In some embodiments, the systems, methods, and apparatus described herein may include an extraction membrane, an ammonia ($NH_3$) sensor comprised of a hydrophobic material such as polytetrafluoroethylene (PTFE) substrate impregnated with a pH indicator such as Bromophenol Blue, light emitting diodes (LEDs) at the maximum absorption wavelength of the indicator, and photodiodes configured to measure absorbance changes following ammonia ($NH_3$) exposure. In addition, LEDs at a different wavelength where the indicator does not absorb light may be configured with corresponding photodiodes to produce a second reading that allows further correction of sensor signal drifts. The photodiodes transduce the color change of the sensor to an electronic signal, which can be transmitted (by wire or wirelessly) to smart devices for readouts. The described systems, methods and apparatuses may exhibit high sensitivity, high specificity, fast reversibility, and rapid response time in comparison with conventional systems.

As discussed above, urine total ammonia (ammonia ($NH_3$) and ammonium ($NH_4^+$)) may be used as a biomarker for the early detection of acute kidney injury (AKI) and other physiological conditions and ailments. The systems and methods described herein may be used for the detection of total ammonia (ammonia ($NH_3$) and ammonium ($NH_4^+$)) in urine or other biological fluids and/or ammonia ($NH_3$) gas in the headspace of urine or the headspace of other biological fluids. Biological fluids may include one or more of whole blood, blood plasma, blood serum, intracellular fluid, intercellular fluid, interstitial fluid, lymphatic fluid (lymph), sweat, urine, pleural fluid, pericardial fluid, peritoneal fluid, biliary fluid (bile), feces, cerebrospinal fluid, synovial fluid, saliva, sputum, nasal fluid, or ocular fluid.

As will be discussed further below, the systems and methods described herein may include an analyzer device. The analyzer device, optionally referred to herein as a Colorimetric Optoelectronic Dynamics Analyzer (or simply "CODA"), may provide real-time and continuous urine total ammonia (ammonia ($NH_3$) and ammonium ($NH_4^+$)) detection and quantification using very small amounts of urine or bodily fluid. The analyzer device may use a sensor embedded with an ammonia ($NH_3$)-sensitive sensing probe based on a pH dye. Unlike conventional detection methods for human body bio-fluids, which directly measure dissolved ammonium ($NH_4^+$) in blood or urine, the sensing chamber of the analyzer device may detect and measure ammonia ($NH_3$) gas in the urine headspace by converting fluid ammonium ($NH_4^+$) to gaseous ammonia ($NH_3$) by alkaline exposure of the bio-fluid (or sample of bodily fluid) before measurement.

Turning now to FIG. 1, a schematic illustration of a system for detecting total ammonia (ammonia ($NH_3$) and ammonium ($NH_4^+$)) of a biological fluid (e.g., urine, etc.) is presented. As illustrated in FIG. 1, a wearable analyzer may include an analyzer device 100 that is in wireless communication to a user interface device 102. In some embodiments, the analyzer device 100 may include an extraction membrane 104, ammonia ($NH_3$) sensor 106, photodiodes 108, light emitting diodes 110, microcontroller 112, Bluetooth® transmitter/receiver 114, a flexible printed circuit board 116, and/or flexible batteries 118. The extraction membrane 104 may be configured to be in fluid communication with a biological fluid sample, such as urine, or the headspace of a biological fluid sample 120.

In some embodiments, the extraction membrane 104 may be located between an area in fluid communication with a bodily fluid and a sensing chamber (that contains the ammonia ($NH_3$) sensor 106). The extraction membrane 104 may be configured to convert at least a portion of the ammonium ($NH_4^+$) contained within the bodily fluid into ammonia ($NH_3$) and dispel the converted ammonia ($NH_3$) into the sensing chamber. As will be discussed further below, in some embodiments, the extraction membrane may include a distributor layer, an alkaline layer, a hydrophobic layer and an indicator layer. The distributor layer may be configured to distribute the sample of bodily fluid along the extraction membrane. The alkaline layer may be configured to convert at least a portion of the ammonium ($NH_4^+$) within the sample of bodily fluid into ammonia ($NH_3$). In some embodiments, the alkaline layer may include organic hydroxide and/or sodium hydroxide. The hydrophobic layer may be configured to filter the converted ammonia ($NH_3$) from the sample of bodily fluid and dispel the converted ammonia ($NH_3$) into the sensing chamber. In some embodiments, the hydrophobic layer may include polytetrafluoroetheylene and the like. The indicator layer may include bromophenol blue, a plant-based pH indicator (e.g. anthocyanin), or any other suitable material. The indicator layer may be configured to change in color, being responsive to a quantity and/or concentration of the ammonia ($NH_3$) gas of the bodily fluid and/or the ammonia ($NH_3$) gas extracted from the fluid ammonium ($NH_4^+$) exposure to and interaction with the alkaline layer.

In some embodiments, the ammonia ($NH_3$) sensor 106 may include a colorimetric nanocomposite sensor that uses composite sensing nanomaterials for detection of ammonia ($NH_3$) on a sensing area 106A and a reference area 106B (without a sensing probe) to assess absorbance color changes. In some embodiments, the absorbance is calculated as the negative log of the signal from the sensing area divided by the signal from the reference area. Together the light emitting diodes 110 and the photodiodes may form a detection unit (or hybrid sensor) as is discussed further below. The ammonia ($NH_3$) sensor 106 may also include a processor with non-transitory memory storing instructions that when executed, cause the processor to quantify an amount of ammonia ($NH_3$) present in the sensing chamber.

As will be discussed in further detail below, the ammonia ($NH_3$) sensor may include four photodiodes: two sensing photodiodes placed in the sensing area 106A, and two reference photodiodes placed in the reference area 106B. Two light emitting diodes may be configured to illuminate the indicator layer. In some embodiments, the light emitting diodes may emit red light. In some embodiments, the light source and light detector may be configured to use a CMOS chip (camera).

The ammonia ($NH_3$) sensor 106 may quantify the amount of ammonia ($NH_3$) present in the sensing chamber by calculating an absorbance metric of the indicator layer based on a signal from the first photodiode and a signal from the second photodiode, and converting the absorbance metric to the quantifiable amount of ammonia ($NH_3$) by comparing the calculated absorbance metric to one or more reference values indicating a relationship between absorbance and ammonia ($NH_3$) concentration. In addition, the absorbance signal may be further corrected from the LEDs and corresponding photodiodes designated to record a sensor signal at a wavelength where the indicator has no light absorption (minimum absorption wavelength), such as a wavelength higher than 675 nm.

In some embodiments, the user interface 102 is presented on a computing device. The computing device can be on-board with the detection system, or in an external device. The on-board computing device may be associated with a display. In the external device, the user interface 102 may include one or more software applications that may acquire data from the analyzer device 100, and generate one or more reports for display on a graphical user interface of the user interface 102. The generated reports may require the performance of one or more analytical computations on the data acquired from the analyzer device 100. The computing device may be a mobile device such as a tablet computer (e.g., Apple iPad, Samsung Galaxy Tab, etc.), smart phone (e.g., Apple iPhone, Blackberry Phone, Android Phone, etc.), smart watch (e.g., Apple Watch, etc.), Personal Digital Assistant (PDA), Personal Computer device (PCs; through web browser and installable software), and/or other similar device. The computing device may be wired or communicatively coupled to the analyzer device 100 over a network such as a Local Area Network (LAN), Wide Area Network (WAN), digital subscriber line (DSL), wireless networks (e.g., 3G or 4G networks), or other equivalent connection means. A Bluetooth® communication configuration is illustrated in FIG. 1.

The computing device may include a processing device, memory, data storage device, and communication interface. The components may communicate with each other via a data and control bus. The processing device may include, without being limited to, a microprocessor, a central processing unit, an application specific integrated circuit (ASIC), a field programmable gate array (FPGA), a digital signal processor (DSP) and/or a network processor. The processing device may be configured to execute processing logic for performing the operations described herein. In general, the processing device may include any suitable special-purpose processing device specially programmed with processing logic to perform the operations described herein.

Memory may include, for example, without being limited to, at least one of a read-only memory (ROM), a random access memory (RAM), a flash memory, a dynamic RAM (DRAM) and a static RAM (SRAM), storing computer-readable instructions executable by processing device. In general, memory may include any suitable non-transitory computer readable storage medium storing computer-readable instructions executable by the processing device for performing the operations described herein. In some examples, the computer device may include two or more memory devices (e.g., dynamic memory and static memory).

The computing device may include a communication interface device, for direct communication with other computers (including wired and/or wireless communication), and/or for communication with a network. In some examples, the computing device may include display device (e.g., a liquid crystal display (LCD), a touch sensitive display, etc.). In some examples, the computing device may include a user interface (e.g., an alphanumeric input device, a cursor control device, etc.).

In some examples, the computer device may include a data storage device storing instructions (e.g., software) for performing any one or more of the functions described herein. The data storage device may include any suitable As illustrated in FIG. 1, the analyzer device 100 may have various configurations. For example in Panel C of FIG. 1, a tubing version of the analyzer device 100 is illustrated. In the tubing version of the analyzer device 100, the wireless flexible printed circuit board 116 is configured to have flexible batteries 118 and flexible displays located beneath the wireless flexible printed circuit board 116. The tubing version of the analyzer device 100 is configured so that the extraction membrane is in fluid contact with urine in a tube. In Panel C of FIG. 1, the analyzer device 100 is placed in series with a patient's urine in catheter tubing or in a collection bag.

In some embodiments, in order to mitigate fouling of the analyzer device, the sensor surface may be located in a direction parallel to urine flow to avoid deposits of urine solids (see Panel C of FIG. 1).

In some embodiments, a hydrophilic modification to the connector wall is included to enhance easy wetting of the connector and membrane, to mitigate clogging of the sample into the membrane due to plugging the analyzer into a catheter. Additionally, one embodiment of the system described herein may use leak-safe standard tubing fittings from Jaco™ so that no urine leakage will be allowed.

Alternatively, as illustrated in Panel D of FIG. 1, an adhesive version of the analyzer device 100 may be used to adhere the device 100 to a diaper or skin such that the extraction membrane 104 is in contact with urine or sweat, respectively.

In some embodiments, the analyzer device 100 may provide specific, fast-response and accurate measurements for ammonia ($NH_3$) gas concentrations ranging from 2 ppm to 1000 ppm (corresponding to 0.1 mmol/L to 50 mmol/L of ammonium ($NH_4^+$) in liquid fluid). The ammonia ($NH_3$) sensor 106 may be very selective to ammonia ($NH_3$), especially considering the high amount of interferents in urine headspace. As will be discussed below, a sensor 106 built in accordance with the methods and systems described herein, may show good reusability in long sampling periods, enabling daily use for medical applications. Accordingly, the analyzer device 100 may be able to accurately monitor the total ammonia (ammonia ($NH_3$) and ammonium ($NH_4^+$)) level in urine and/or extracted ammonia ($NH_3$) gas from urine, as evidenced by comparison to measurements from a commercial reference method (ISE electrode), discussed further in the Experiments section below. In some embodiments, the ammonia ($NH_3$) sensor 106 may be durable and can last at least 10 weeks. As will be discussed below, the sensor 106 synthesis process may be simple and easily reproducible. Additionally, the analyzer device 100 may connect wirelessly to smart devices, thereby providing flexibility for measurements for inpatient, outpatient, or personal health monitoring.

In some embodiments, the analyzer device 100 may be especially well-suited for hospital or ambulatory settings. As discussed above in connection with FIG. 1, the analyzer device 100 may include a replaceable cartridge containing a combined extraction membrane/sensor and optoelectronic components for detection of ammonia ($NH_3$), signal conditioning, and wireless communication with a user interface device. Software for data acquisition, signal processing algorithms, display, transmission, and user interface may be included in the analyzer device 100 and/or the user interface 102.

In some embodiments, a sample of the bodily fluid (such as urine or sweat) may be diverted onto the extraction membrane/sensor cartridge (replaceable cartridge) where ammonia ($NH_3$) is extracted. The extracted ammonia ($NH_3$) may then interact with the cartridge's colorimetric sensor, thus changing its color relative to the ammonia ($NH_3$) concentration. Software including one or more signal processing algorithms may then determine the ammonia ($NH_3$) concentration. In some embodiments, the rate of urine or sweat total ammonia (ammonia ($NH_3$) and ammonium ($NH_4^+$)) excretion may be determined via knowledge of the extracted ammonia ($NH_3$) concentration and the fluid's pH, and/or the fluid's rate of flow. In some embodiments, the rate of urine, skin headspace or sweat total ammonia (ammonia ($NH_3$) and ammonium ($NH_4^+$)) excretion may also be estimated via knowledge of the extracted ammonia ($NH_3$) concentration and the fluid's density, specific gravity, osmolality, or osmolarity. In some embodiments, testing may be done in an automated and serial fashion, with tests occurring every few minutes. Data may then be transmitted automatically from the analyzer device 100 to the user interface 102 where the data may be processed and displayed graphically.

For example, the user interface 102 may display changes of urine total ammonia (ammonia ($NH_3$) and ammonium ($NH_4^+$)) or ammonia ($NH_3$) concentration or urine total ammonia (ammonia ($NH_3$) and ammonium ($NH_4^+$)) or ammonia ($NH_3$) rate of excretion over time. The user interface 102 may be configured to be periodically reviewed by health care providers, patients, and the like. In some embodiments, the analyzer device 100, or user interface 102 may be able to identify an abrupt or unexpected change in urine total ammonia (ammonia ($NH_3$) and ammonium ($NH_4^+$)) concentration and/or excretion rate and trigger an automated alert so that health care providers can be informed as soon as possible regarding relevant and associated health or metabolic status changes which culminated in the change urine total ammonia (ammonia ($NH_3$) and ammonium ($NH_4^+$)) parameters (e.g., either possible acute kidney distress or a possible acute kidney injury (AKI) event). Past measurements of total ammonia (ammonia ($NH_3$) and ammonium ($NH_4^+$)) concentration and/or excretion rate may be stored in a database and be available for comparison.

Figure 5:
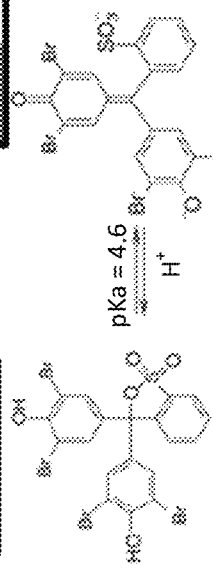
FIG. 5 illustrates a graph of absorbance change of a sensor for ammonia (panel A), an assembly diagram for a sensor for ammonia (panel B), a graph of absorbance change of a sensor before and after exposure to ammonia (panel C), and a diagram of a sensor assembly (named as hybrid sensor) (panel D) according to an aspect of the present disclosure.
Figure 5:
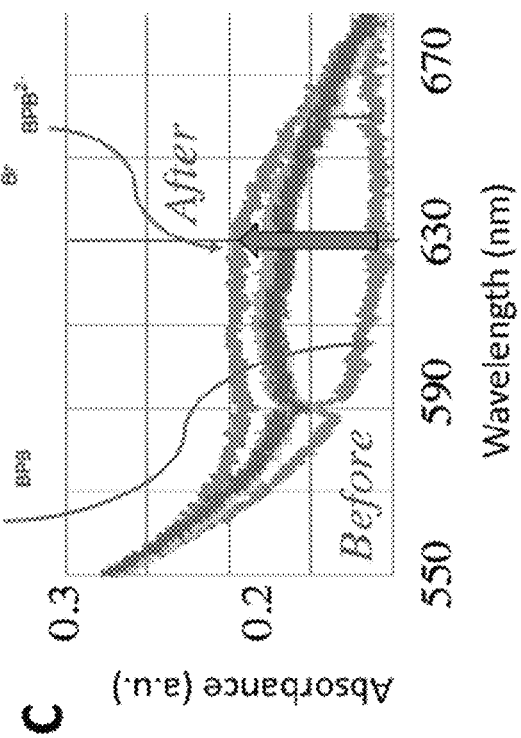

As discussed above, the combined extraction membrane/sensor is based on a colorimetric sensor to measure ammonia ($NH_3$) and the extraction membrane, which are both assembled on the same substrate/unit so that the detection principles are scalable and miniaturized (as illustrated in FIGS. 1 and 5). The extraction membrane with an alkaline buffered extractive capacity can be scaled down to centimeters to millimeters in dimensions. In some embodiments, the extraction membrane may be configured to extract ammonia ($NH_3$) from ammonium ($NH_4^+$) at pH equal or higher than 10 into the gas phase following Henry constant partitioning behavior. The colorimetry components may be configured to detect light absorption per unit area so that the sensitivity is determined by binding sites per unit area, independent of the total sensing area. In other words, the systems and methods described herein may allow the combined extraction membrane/sensor size to scale without sacrificing the extraction quality, sensitivity and detection limit. The sensor detection method is low cost with high performance flexible optoelectronics components such as LEDs and photodiodes (PDs) (see Panel D of FIG. 5).

Figure 2:
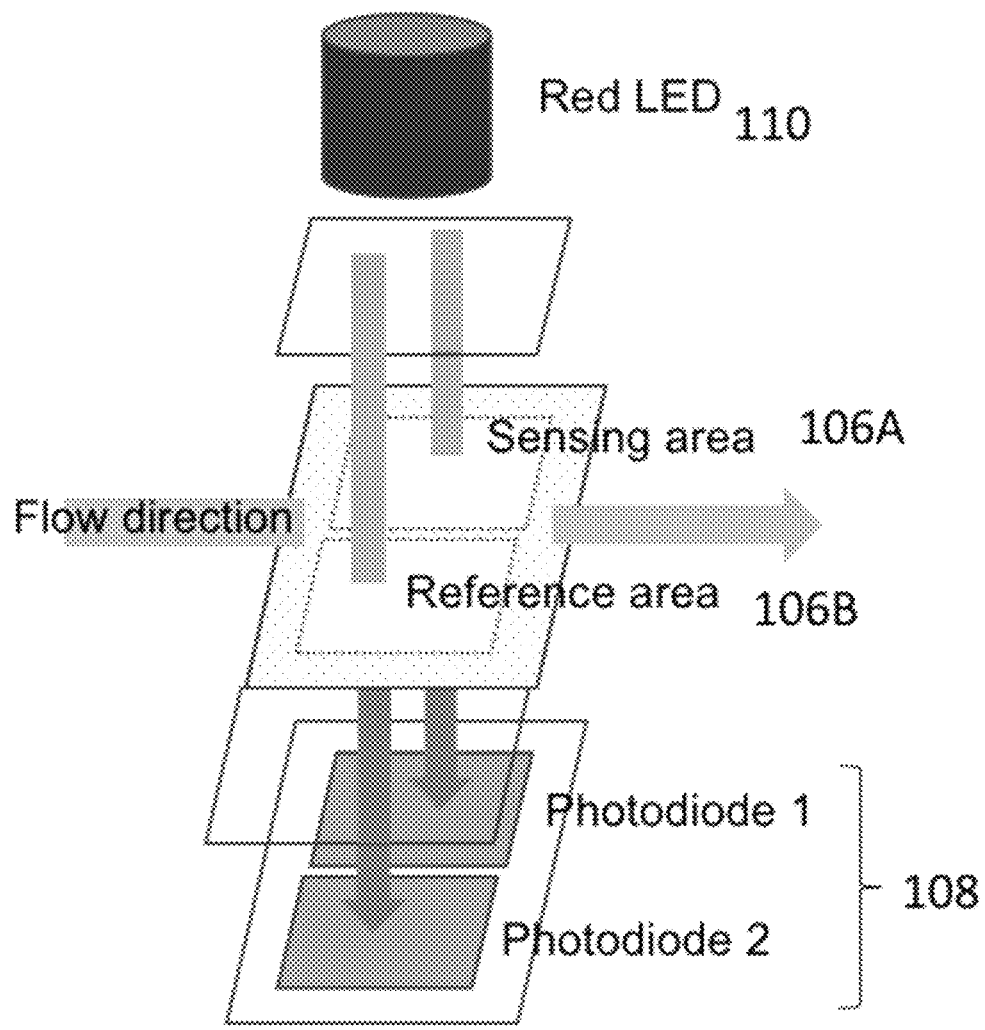
FIG. 2 illustrates a schematic diagram of an example of a sensing chamber for ammonia according to an aspect of the present disclosure.

We turn now to FIG. 2, which illustrates a schematic diagram for a sensor for ammonia ($NH_3$) according to an aspect of the present disclosure. As illustrated, the sensing chamber may include a red light emitting diode 110 that is positioned to illuminate sensing area 106A, and reference area 106B that are located parallel to the flow direction. Photodiodes 108 may be placed below the sensing 106A and reference areas 106B. A target gas can be directed into the sensing chamber, where it is exposed to the sensor which then exhibits a color change proportional to the concentration of ammonia ($NH_3$) in the target gas. The photodiodes 108 may be mounted on the printed circuit board with resistors to gain photodiode signal sensitivity. By using Beer's Law, the changes on the negative log of the signal ratio between the sensing and reference areas may be used to determine the concentration of ammonia ($NH_3$) gas via absorbance.

Figure 3:
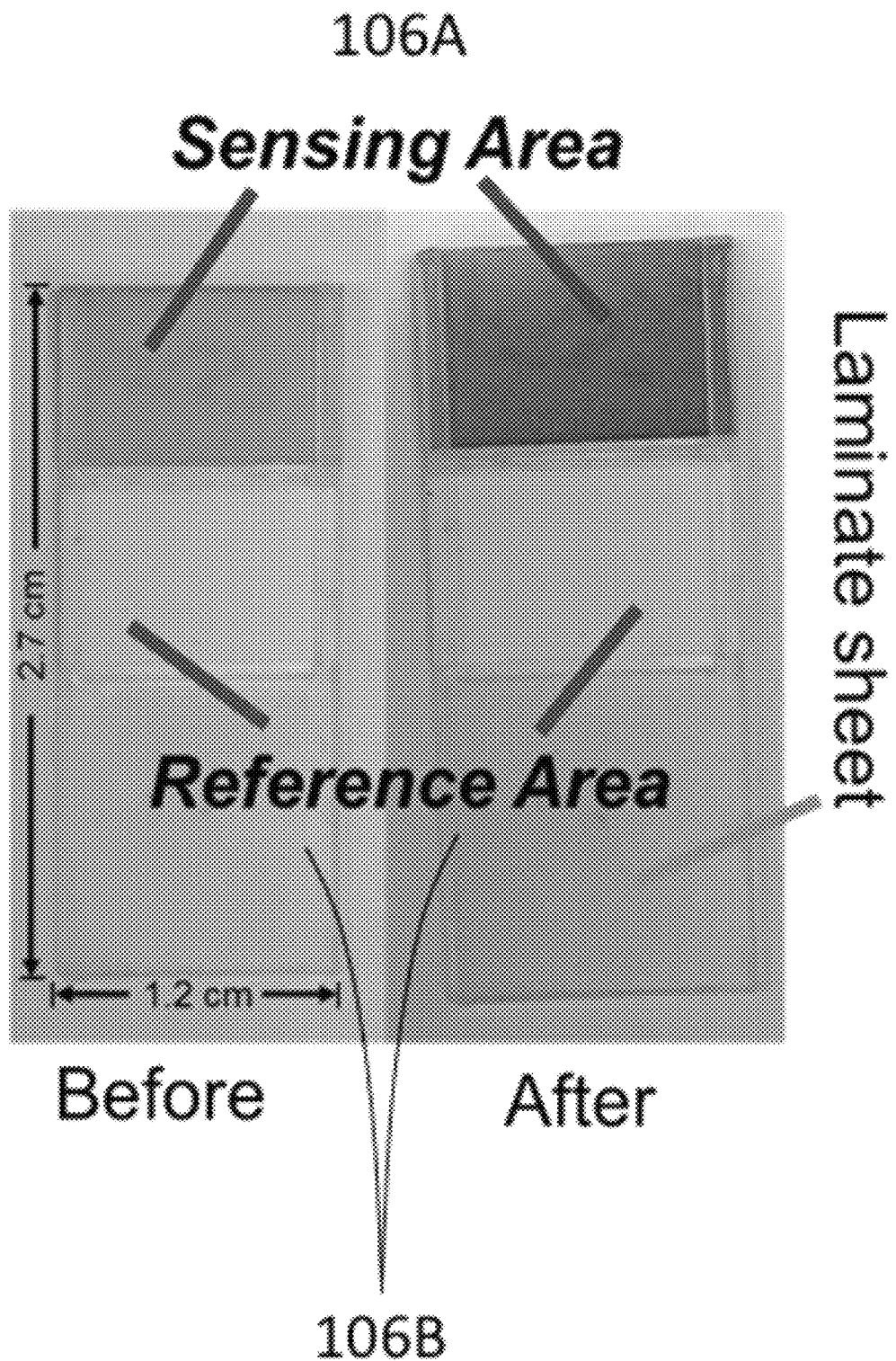
FIG. 3 illustrates a picture of a sensor for ammonia ($NH_3$) detection from body fluids according to an aspect of the present disclosure.

We turn now to FIG. 3, which illustrates an analyzer cartridge for a fluid's total ammonia (ammonia ($NH_3$) and ammonium ($NH_4^+$)) according to an aspect of the present disclosure. As illustrated in FIG. 1, the analyzer device 100 may be in wireless communication with a user interface 102. Alternatively, wired communication may be used. Additionally, as illustrated in FIG. 3, the sensing area may be sensitive to ammonia ($NH_3$) concentrations. In the before and after sections of FIG. 3, the color change in the sensing area 106A is illustrated after exposure to ammonia ($NH_3$).

Figure 4:
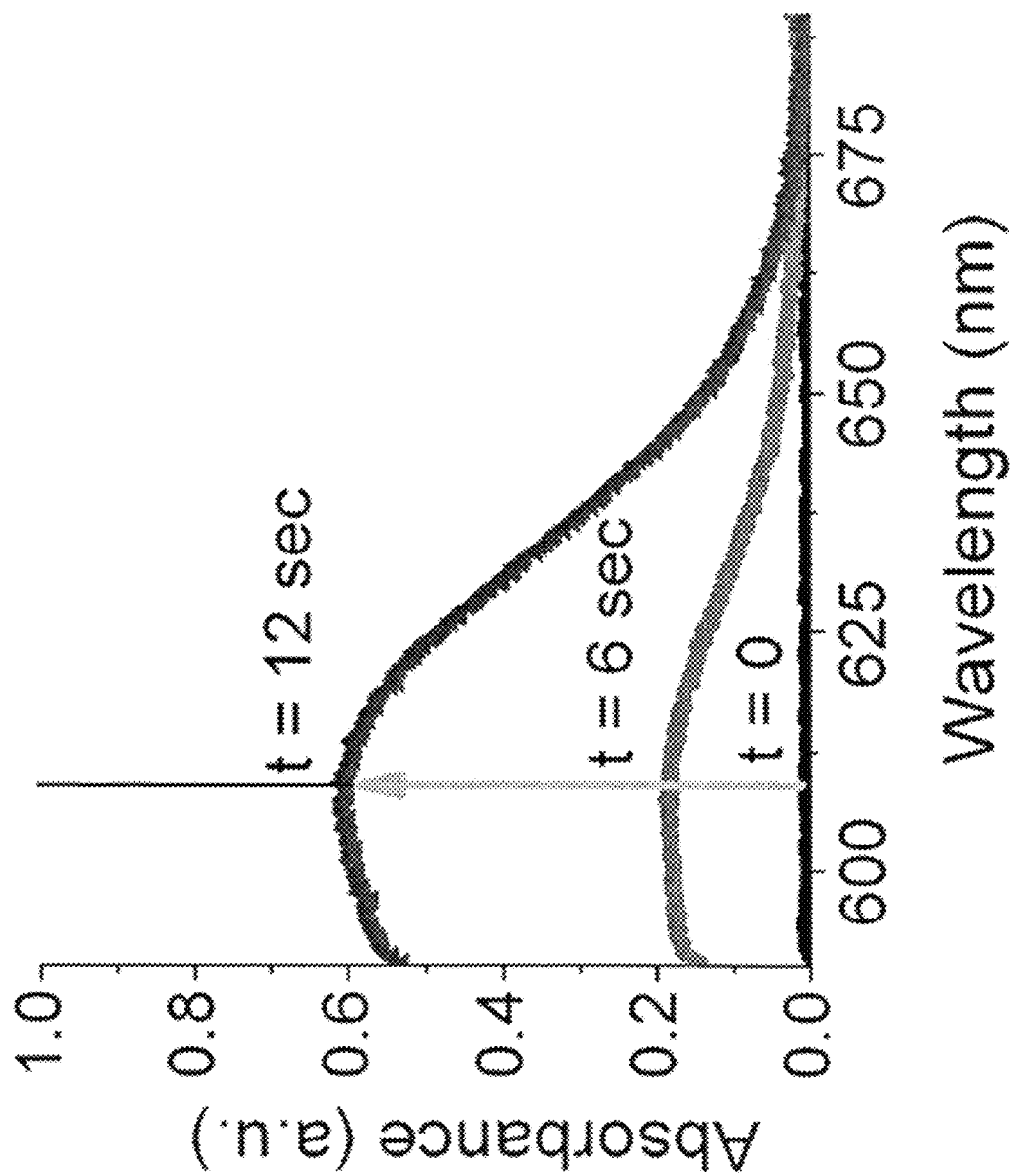
FIG. 4 illustrates a graph of absorbance change in accordance with an aspect of the present disclosure.

We turn now to FIG. 4, which illustrates a graph of absorbance change in accordance with an aspect of the present disclosure. The absorbance spectrum change of the sensor obtained with a JAZ Spetrophotometer's sensor chamber is illustrated before and after exposure to ammonia ($NH_3$). As illustrated, the sensor has a maximum absorbance range wavelength between 600 and 630 nm. Maximum absorbance of the sensor for ammonia ($NH_3$) occurs between 600-630 nm, and minimum absorbance occurs at wavelengths higher than 675 nm.

We turn now to FIG. 5, which illustrates a schematic diagram and assembly diagram for a sensor for a fluid's total ammonia (ammonia ($NH_3$) and ammonium ($NH_4^+$)) according to an aspect of the present disclosure. Panel A in FIG. 5 illustrates a nanocomposite sensor of bromophenol blue (BPB) as included in the indicator layer of the extraction membrane. As illustrated in Panel A of FIG. 5, the sensing elements may change in color after exposure to ammonia ($NH_3$). The sensing elements may be made of chemically selective nanocrystals of BPB that are deposited on a porous hydrophobic substrate that provides a fast, reversible response to ammonia ($NH_3$). The sensor preparation process is illustrated in Panel B of FIG. 5. As illustrated, the sensor fabrication process may include a laminating and laser cutting process. Panel C of FIG. 5 illustrates that absorbance spectrum of a sensor during exposure to ammonia ($NH_3$). A maximum absorbance wavelength of 630 nm is indicated. Panel D of FIG. 5 illustrates a sensor assembly (named as hybrid sensor) in accordance with the laminating process illustrated in Panel B of FIG. 5. The schematic of this sensor assembly illustrates the optoelectronic components for simultaneous detection at maximum and minimum absorbance wavelengths.

As illustrated in Panels A and C of FIG. 5, the nanocomposite for the ammonia ($NH_3$) sensor may be fabricated using a pH indicator (e.g., Bromophenol Blue, BPB) as the molecular probe. Any suitable alternative pH indicators may be used. In some embodiments, the colorimetric sensor substrate may be constructed from custom-made or commercial (e.g., polytetrafluoroethylene (PTFE)) membranes that are soaked in BPB (a colorimetric sensing agent) solution, which produces nanocrystals when deposited on the substrate. The substrate of modified PTFE may then be dried at 25° C. This process may cause the molecular probe (BPB) to create a nanocrystalline structure that is formed onto the PTFE. In some embodiments, this may allow for the crucial or fast reaction with the analyte ammonia ($NH_3$). In some embodiments, the molecular probes may be used for the fast and selective detection of ammonia ($NH_3$) from urine or skin headspace. Different combinations of chemicals and substrate preparation methods were screened and studied as will be discussed below in connection with the experiments. In some embodiments, the porous hydrophobic substrate for immobilization of BPB (PTFE) may promote not only fast ammonia ($NH_3$) reaction but also a reversible reaction since the substrate does not retain surrounding water, and thus avoids solubilizing ammonia ($NH_3$) permanently. As illustrated, the resulting nanocomposite demonstrated fast and highly responsive nanocrystals (<200 ms) (see Panels C in FIGS. 5 and 6) with high specificity in the presence of urine/sweat interferent molecules (see Panel A in FIG. 6).

In Panel D of FIG. 5, the sensor structured is depicted with its main components. Main components include a laminated membrane on top of a spacer, and the laminated membrane and spacer are located on top of the sensor. Alternatively, the extraction membrane may be physically separated from the sensor or sensor chamber. In addition, the assembly has a feed distributor that comes in direct contact with the biological fluid (i.e., urine, sweat). The illustrated components may be integrated into a sensor cartridge using a mask layer via the lamination process illustrated in Panel B of FIG. 5. The laminated components may form a single assembly that fits into the sensor chamber with the optoelectronic components as shown in Panel D of FIG. 5 and Panel A of FIG. 1. The signal produced by the optoelectronic components may be captured electronically and processed with calibration data. The data may then be transmitted wired or wirelessly to the user interface 102. Data may then be displayed graphically against time to show trends of body fluid total ammonia (ammonia ($NH_3$) and ammonium ($NH_4^+$)) concentration and/or excretion rate. In some embodiments, automatic warning signals for rapid changes in body fluid total ammonia (ammonia ($NH_3$) and ammonium ($NH_4^+$)) concentration and/or excretion may be sent to attending clinicians to alert them of changing metabolic status and/or potentially deleterious conditions.

The cartridge is designed with integrated flexible electronics to be adapted in a tubular system or an adhesive strip, so that it can "plug and play" easily by the user as illustrated in the two configurations of the analyzer device illustrated in Panels C and D of FIG. 1. In some embodiments, the LEDs and PDs may be placed on the flexible printed circuit board (PCB) as close to the sensor cartridge as possible in order to eliminate the need for focusing optics, thus resulting in reductions of size and cost (see Panels A and D of FIG. 5).

The LEDs and PDs may be used in reflection mode. In order to mitigate sensor drift signals, two LEDs may be used. The analyzer device 100 may form an integrated unit that is adapted to fit with tubing or an adhesive strip. In both versions (see Panels C and D of FIG. 1) of the wearable analyzer, electronics, including electro-optical components, microcontroller, power from a small thin film flexible batteries (e.g. Blue Spark Technologies Inc.), small display, power switch, and low energy Bluetooth® are mounted onto the flexible PCB. The flexible PCB may have one microcontroller for controlling and reading colorimetric sensor signals, general functions of data collection, minimal data processing for embedded display (if use as an option for instant total ammonia (ammonia ($NH_3$) and ammonium ($NH_4^+$)) concentration), and transmission via Bluetooth®. In some embodiments, the entire described assembly may be placed inside a sleek housing designed to be portable, functional, and ergonomic.

In some embodiments, in order to mitigate the baseline drift of the ammonia ($NH_3$) sensor with time of use due to changes in temperature, mechanical manipulation, stability of electrical components and the like, the sensor may be configured with two identical sensing areas and two identical reference areas. Each pair of the sensing and reference areas may be illuminated with an LED. The LEDs may have distinctive wavelengths. One LED may have a wavelength of 630 nm, and be used to capture the maximum absorbance change of the sensing probe (Abs max). The second LED may have a non-absorption wavelength (e.g. 700 nm), and be used to capture the baseline minimum absorbance of the sensing probe (Abs min). The difference in absorbance: Delta Absorbance=Absorbance max−Absorbance min may be used as sensor signal. The use of the two wavelengths correct for additional drift of the baseline in the sensor system (see Panel D of FIG. 5).

Furthermore, as also illustrated in Panel D of FIG. 5, in order to mitigate fluctuations of LED light intensity, In some embodiments, a single LED is used to illuminate the sensing and reference areas. The absorbance reading of the sensing probe may be calculated as follows: Absorbance=−log (Sensing area reading/Reference area reading).

Figure 6:
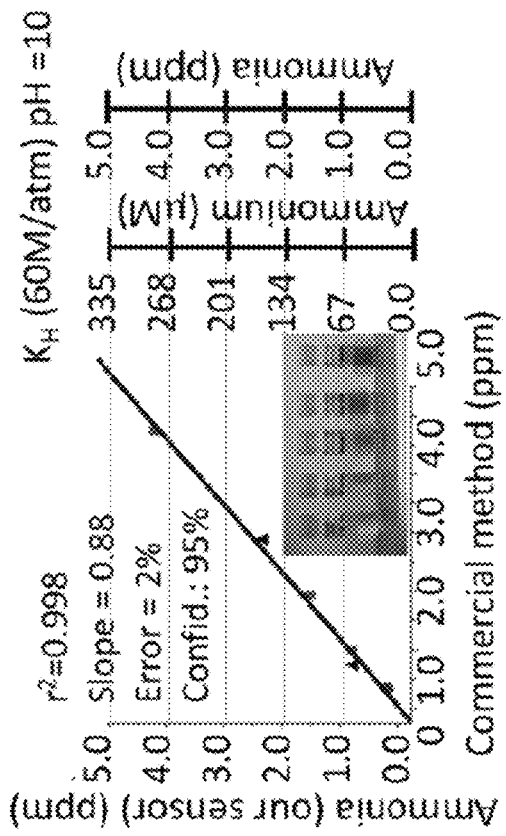
FIG. 6 illustrates graphs associated to the specificity (panel A), accuracy (panel B), reversibility and time response (panel C), and sensor lifetime and stability (panel D) of sensor for ammonia according to an aspect of the present disclosure.
Figure 6:
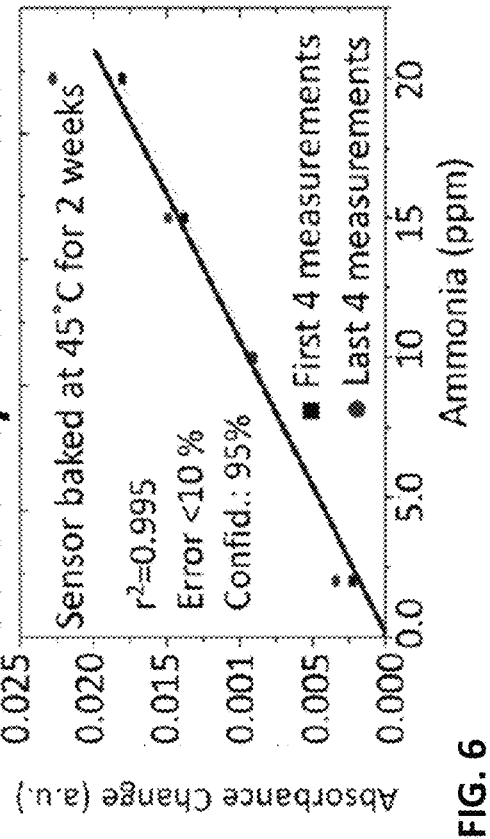
Figure 6:
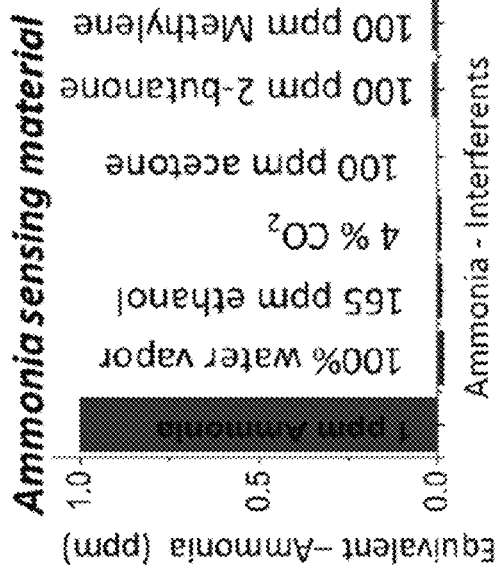
Figure 6:
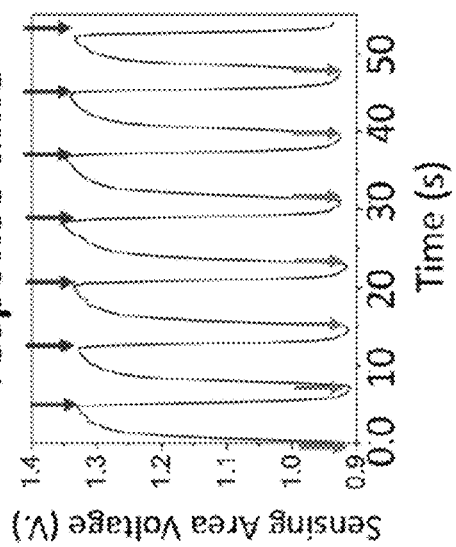

We turn now to FIG. 6, which illustrates a specificity analysis (Panel A), ammonia ($NH_3$) detection accuracy (Panel B), reversibility and response time (Panel C) and sensor lifetime (Panel D).

As illustrated in Panel A of FIG. 6, the sensor may be configured to be specific to ammonia ($NH_3$) and not reactive to other materials.

Furthermore, as illustrated in Panel B of FIG. 6, the assembly of the extraction membrane and ammonia ($NH_3$) sensor may demonstrate high sensitivity for detection of ammonia ($NH_3$), ranging from parts per billion (ppb) to several parts per million (ppm) ammonia ($NH_3$) detection, and a high level of accuracy when compared to an enzymatic reference method or the commercial method such as an ion selective electrode. For example, as illustrated in Panel B of FIG. 6 the correlation coefficient (r2)=0.998, 88% accuracy with 2% error (95% conf. interval).

Panel C of FIG. 6 illustrates the reversibility and time response of the sensor. The sensing area voltage response to cyclical exposure to high parts per million and low parts per million of ammonia ($NH_3$) is depicted over time.

Panel D of FIG. 6 illustrates sensor sensitivity (absorbance vs. concentration) after exposure to ammonia ($NH_3$) levels for 24 hours. As illustrated, the sensor demonstrates reusability after pre-conditioning. Pre-conditioning may include placing the analyzer device in 45 degrees Celsius for 2 weeks. This may allow for the robust immobilization of the components to the supporting substrates as well as harsh shipping and operational use conditions. In connection with this test, ammonia ($NH_3$) extraction was performed on a highly concentrated glycine buffered membrane of polystyrene/PTFE at pH=10, which was cured with organic hydroxides.

Figure 7:
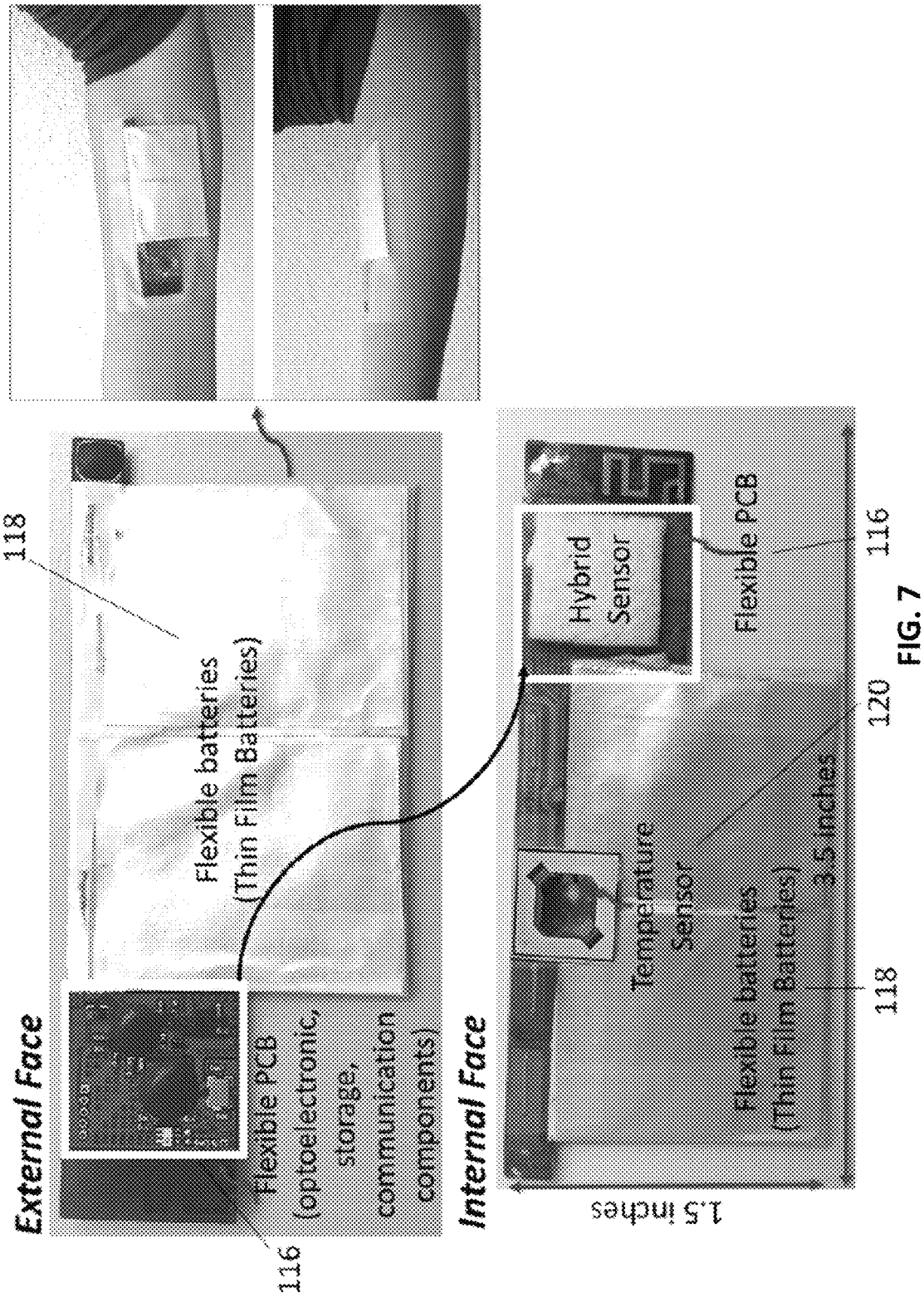
FIG. 7 illustrates a picture and schematic diagram for a sensor for ammonia according to an aspect of the present disclosure.

In some embodiments, as illustrated in FIG. 7, the analyzer device may further include a temperature sensor 120. The illustrated analyzer device is configured for contact with the skin in order to measure total ammonia (ammonia ($NH_3$) and ammonium ($NH_4^+$)) in sweat. In some embodiments, the temperature sensor 120 may be implemented next to the assembly sensor surface to determine the in-situ temperature of the assembly sensor, and provide corrections of ammonia ($NH_3$) level readings due to temperature changes. Furthermore, the embodiments of the analyzer device depicted in FIG. 7 and Panel D of FIG. 1, may include an adhesive layer that provides hermetic sealing of the skin headspace compartment.

In some embodiments, an analyzer device may include one or more sensors for at least one of fluid pH, fluid density, fluid specific gravity, fluid osmolality, fluid temperature, oxygen ($O_2$) partial pressure, carbon dioxide ($CO_2$) partial pressure, nitrogen ($N_2$) partial pressure, sodium ($Na^+$), potassium ($K^+$), chloride ($Cl^-$), bicarbonate ($HCO_3^-$), calcium ($Ca^{2+}$), magnesium ($Mg^{2+}$), phosphate ions (including $H_2PO_4^-$, $HPO_4^{2-}$, $PO_4^{3-}$), creatinine, urea, uric acid, cystatin C, amino acids, kidney tubular brush border enzymes, albumin, Tamm-Horsfall protein, insulin, cortisol, cortisone, creatinine, lactate, cyclic AMP, neutrophil gelatinase-associated lipocalin (NGAL), kidney injury molecule-1 (KIM-1), insulin like growth factor binding protein 7 (IGFBP7), and tissue inhibitor of metalloproteinases 2 (TIMP2). An analyzer device may include a flow sensor configured to determine a total volume of fluid and/or a rate of fluid production. In some embodiments, the rate of fluid production may be expressed in units of urine volume per units of time.

In some embodiments, the analyzer device 100 may also include one or more signal processing algorithms configured to process raw data from the sensor and calibrate for any memory effects within the sensor. In some embodiments, the signal processing algorithm may account for any memory effects within the sensor when the concentration of the feed solution is rapidly changed.

Measurement of total ammonia (ammonia ($NH_3$) and ammonium ($NH_4^+$)) in biological samples has traditionally presented technical challenges. Urine total ammonia (ammonia ($NH_3$) and ammonium ($NH_4^+$)) and/or ammonium ($NH_4^+$) concentration is not generally measured, and medical doctors have been trained to calculate and utilize a flawed indirect indicator (i.e., the "urine anion gap") to estimate the concentration of total ammonia (ammonia ($NH_3$) and ammonium ($NH_4^+$)) and/or ammonium ($NH_4^+$) in urine samples. However, a more reliable method for determining the total ammonia (ammonia ($NH_3$) and ammonium ($NH_4^+$)) levels in blood, urine, and other biological fluids (e.g., breath, sweat), can be of great benefit in certain clinical scenarios. For instance, blood total ammonia (ammonia ($NH_3$) and ammonium ($NH_4^+$)) is an important marker (albeit less convenient to sample than urine) used to inform treatment decisions for patients with urea cycle disorders, organic acidurias, carnitine deficiency from defects in fatty acid oxidation, dibasic aminoaciduria, defects in pyruvate metabolism, and liver disease (e.g., cirrhosis). Urine total ammonia (ammonia ($NH_3$) and ammonium ($NH_4^+$)) levels are known to change along with blood levels of total ammonia (ammonia ($NH_3$) and ammonium ($NH_4^+$)) in UCD patients; thus, serial measurement of urine total ammonia (ammonia ($NH_3$) and ammonium ($NH_4^+$)) levels will greatly aid in individualizing treatment for UCD patients without the need for very frequent blood sampling. Dynamic changes in kidney total ammonia (ammonia ($NH_3$) and ammonium ($NH_4^+$)) generation (i.e., renal ammoniagenesis) are stimulated by systemic conditions of acid-base balance, potassium balance, and others; thus, an enhanced moment by moment understanding of urine total ammonia (ammonia ($NH_3$) and ammonium ($NH_4^+$)) levels in patients prone to acid-base or potassium disturbances (i.e., critically ill, hospitalized patients) would augment immediate clinical knowledge and could be leveraged to serve as an early warning signal of rapidly changing (and otherwise under-recognized or unrecognized) systemic conditions. Given the complex interactions of kidney and liver adaptations for total ammonia (ammonia ($NH_3$) and ammonium ($NH_4^+$)) homeostasis, disorders of either of these organs may produce rapid changes in total ammonia (ammonia ($NH_3$) and ammonium ($NH_4^+$)) levels of bodily fluids. For instance, acute hepatic dysfunction or decompensation is associated with a rise in blood plasma total ammonia (ammonia ($NH_3$) and ammonium ($NH_4^+$)) levels while acute kidney dysfunction is associated with a rapid decrease in urine total ammonia (ammonia ($NH_3$) and ammonium ($NH_4^+$)). In the outpatient setting, serial monitoring of total ammonia (ammonia ($NH_3$) and ammonium ($NH_4^+$)) levels of biologic samples (including breath, sweat, blood, and urine) could provide a baseline level of total ammonia (ammonia ($NH_3$) and ammonium ($NH_4^+$)), departures from which would be a strong predictive signal of pending liver decompensation in patients with advanced liver disease or a predictive signal of pending kidney dysfunction. In the inpatient setting, patients with indwelling urinary catheters at high risk of acute kidney injury could be monitored for rapid changes in urine total ammonia (ammonia ($NH_3$) and ammonium ($NH_4^+$)) concentration or rate of excretion as the first sign of kidney tissue distress or acute kidney injury. Utilizing that technique could lead to rapid identification of acute kidney injury (compare minutes to hours or days with the lagging, traditional markers including serum creatinine). In either of these scenarios, specific treatments to ameliorate the underlying organ distress or dysfunction could be employed in a much more rapid and more individualized manner than occurs today in modern medical practice. Accordingly, the systems and methods described herein for the detection of total ammonia (ammonia ($NH_3$) and ammonium ($NH_4^+$)) may be adapted for use in the clinical setting.

In some embodiments, the systems and methods described herein may improve the health outcomes of and reduce associated health care costs for hospitalized patients who experience an acute kidney injury (AKI) event. In hospitalized patients with indwelling urinary catheters, the systems and method described herein may continuously monitor for AKI and automatically signal to health care team members if and when a suspected AKI event has begun. Previous studies have shown that when an AKI event is recognized more quickly, the patient's outcome is improved.

In some embodiments, the systems and methods described herein may assist clinical researchers in testing novel therapeutics for AKI in humans. The lack of an ability to diagnose AKI quickly (outside of the controlled laboratory setting in animal models) has greatly impeded most, if not all, past attempts at AKI therapeutic research in human subjects and continues to terribly stunt AKI care in the clinical setting. This is at least in part because novel treatments being tested in human study populations are almost universally given outside of the ideal treatment window, some in reported studies being administered days after the AKI event was known to have begun. Interestingly, many novel therapeutics have shown great promise in animal experiments in which the timing of AKI was precisely known and in which the drug was administered quickly after the AKI event occurred (i.e., within 90 minutes). In the clinical setting, the timing of AKI is not known because: 1) symptoms and signs are almost always absent, 2) present markers lag greatly (i.e., several hours or days) and 3) a detection system to identify the earliest moments of acute kidney distress and/or nascent AKI has never been developed. With proper testing, it is possible that one of the novel therapeutics which has shown significant promise in animal models of AKI will find a place in an easily envisioned future clinical practice in which human AKI can be detected quickly, such as with the systems and methods described herein.

The systems and methods described herein for detection of a fluid's total ammonia (ammonia ($NH_3$) and ammonium ($NH_4^+$)) may also be used in connection with physiology studies in which renal ammoniagenesis and/or renal total ammonia (ammonia ($NH_3$) and ammonium ($NH_4^+$)) excretion rapidly changes. Additionally, the systems and methods described herein may be used for the detection of medical conditions in which current diagnostic tools are limited and in which urine total ammonia (ammonia ($NH_3$) and ammonium ($NH_4^+$)) changes may correlate with disease onset or activity. These conditions include, but are not limited to: 1) changes in kidney function, 2) acute kidney injury or failure, 3) chronic kidney disease, 4) changes in liver function, 5) acute liver injury or failure, 6) chronic liver disease (e.g., cirrhosis), 7) acute gastrointestinal bleeding, 8) chronic gastrointestinal bleeding, 9) genetic or inherited metabolic diseases involving or impacting aspects of ammonia ($NH_3$) and/or ammonium ($NH_4^+$) physiology including its generation, handling, and/or excretion (e.g., urea cycle disorders, organic acidurias, carnitine deficiency from defects in fatty acid oxidation, dibasic aminoaciduria, and defects in pyruvate metabolism), 10) variations of normal metabolic processes (e.g., increased ammonia ($NH_3$) and/or ammonium ($NH_4^+$) generation and excretion following a protein meal), 11) acute or chronic systemic acid/base changes or imbalances due to metabolic processes or disease states, and 12) acute or chronic systemic acid/base changes or imbalances due to respiratory processes or disease states.

In some embodiments, the systems and methods described herein may include a "plug and play," reversible, continuous use and fast response assembly sensor cartridge with specific composition of the extraction membrane and colorimetric sensor.

In some embodiments, the systems and methods described herein may also include signal processing algorithms based on a specific optoelectronic system design with two wavelengths, and built-in mechanisms to combat drifts (built-in sensing and reference areas, as well as temperature sensor).

Moreover, the systems and methods described herein may be adapted for industrial applications such as for the measurement of total ammonia (ammonia ($NH_3$) and ammonium ($NH_4^+$)) in wastewater, such as groundwater discharge, reclaimed water, industrial wastewater, sanitary wastewater, and produced water from oil and gas wells.

EXAMPLES

The following examples are given to illustrate exemplary embodiments of the present disclosure. It should be understood, however, that the present disclosure is not to be limited to the specific conditions or details described in these examples.

Example 1: Field Performance of Analyzer Device

Figure 8:
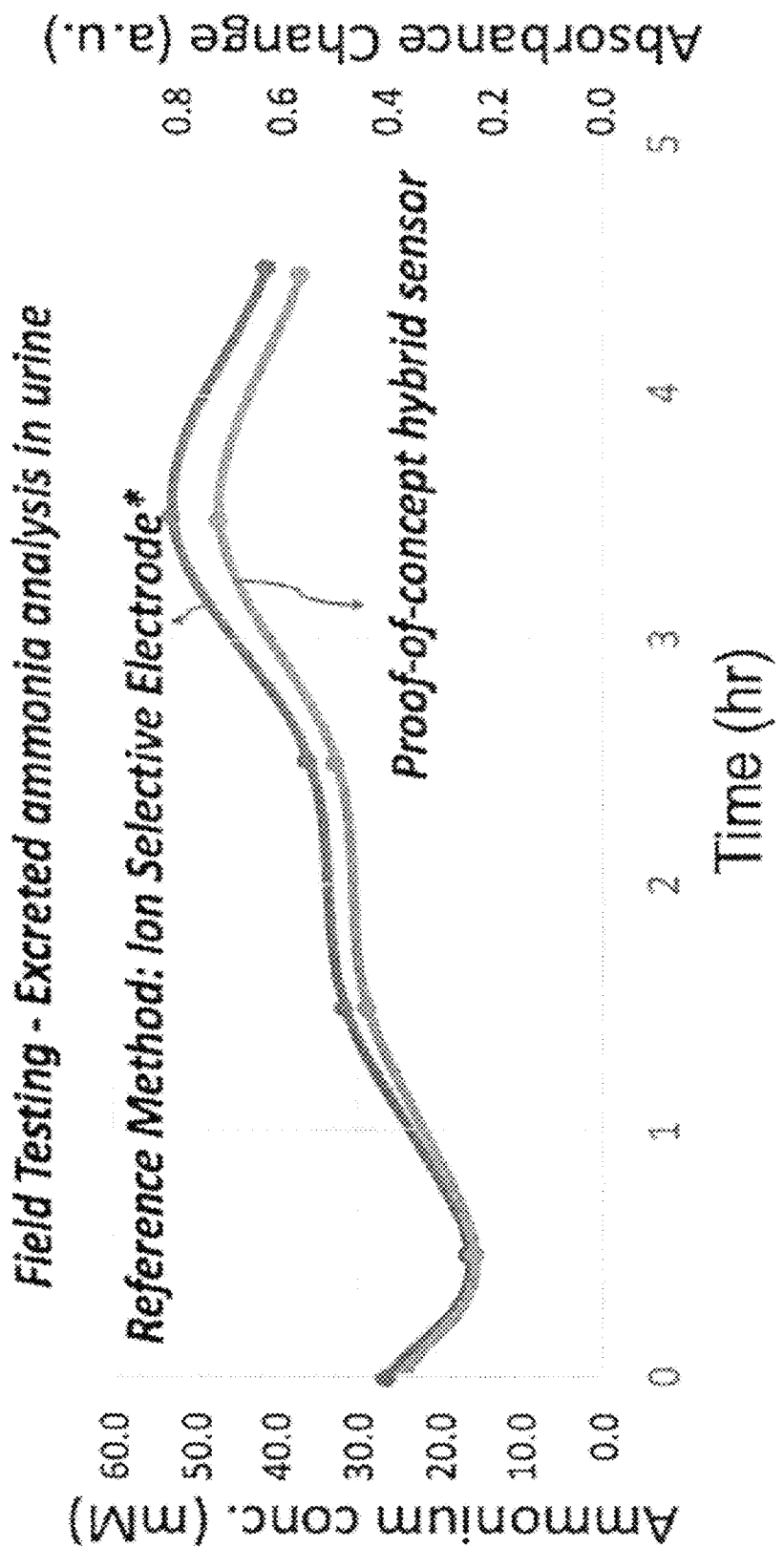
FIG. 8 illustrates a graph of analysis of urine performed with a sensor for ammonia related to an aspect of the present disclosure (named as hybrid sensor), and a reference method: Ion selective electrode.

The response of an analyzer device built in accordance with the systems and methods described herein was tested with real human urine samples in comparison with an ion selective electrode method. The urine samples were assessed from subjects that ate 1 g protein/Kg of weight in a single meal (shake). After the meal, the samples were analyzed after every hour for several hours. The ion selective method required two-point calibration before the analysis of each sample. For the analyzer device, a single assembly sensor was used for analysis of the complete experiment. Both the reference method and the analyzer device's assembly sensor rendered results with correlation close to 1 as is illustrated in FIG. 8. The example illustrates that the analyzer device using a single sensor can perform similarly to a reference method using real samples of human urine, and the example reassured the successful performance of the sensor with re-use several times in a single day.

Example 2: Sensor Preparation

In one example, an ammonia ($NH_3$) sensor in accordance with the systems and methods described herein was constructed based on Bromophenol Blue (BpB) from Sigma-Aldrich. The sensor was synthesized by submerging sensor substrates in a BpB solution. The sensor substrates in the solution were then vortexed using Scientific Industries Vortex Genie 2 for 10 minutes and left to dry for 5 minutes at room temperature. In order to test the effects of the substrate on the detection sensitivity, sensors were constructed on five different sensor substrates, including Polyvinylidene fluoride (PVDF) [Pore size: 0.1 μm and porosity: 80%] from Omnipore™, Polytetrafluoroethylene(PTFE)/Polyethylene (PE) [Pore size: 0.2 or 0.45 μm] from Sterlitech, hydrophobic PTFE [Pore size: 10 μm] from Interstate Specialty Products, hydrophilic PTFE [Pore size: 0.1 and porosity: 70%] from Omnipore™, and Whatman no.1 filter paper [Pore size: 11 μm]. The sensor substrates were cut into a rectangular shape (2.7 cm*1.2 cm) and laminated so that they fit the sensing chamber of the analyzer device, optionally named Colorimetric Optoelectronic Dynamics Analyzer (CODA). A portion of the constructed sensors were sealed in black Mylar™ bags and put in the oven at 45° C. for 2 days to test their performance stability.

Example 3: Analyzer Device Preparation

The analyzer device, or Colorimetric Optoelectronic Dynamics Analyzer (CODA), was constructed in accordance with the systems and methods described herein. The analyzer device includes a horizontal flow channel passing through a sensing chamber, which contains a red LED at the top of the sensor and four photodiodes (a sensing/reference pair and a sensing/reference backup pair) beneath the sensor. The target gas was directed into the sensing chamber, where it was exposed to the sensor which then exhibited a color change proportional to the concentration of ammonia ($NH_3$) in the target gas. The photodiodes (manufactured by Vishay Semiconductor Opto Division) were mounted on the PCB with a 5 M$\Psi$ resistor to gain photodiode (PD) signal sensitivity, which was integrated with a Bluetooth unit, allowing signal transmission to an Android phone. An application was created to provide a user interface to show the signal read by the PDs within the range from 0-3 V. The sensor contained a reference area and a sensing area. The background response from the reference and sensing areas when the sensor was in the chamber was measured to be around 1.2 V. A pair of PDs simultaneously and continuously read the response of the reference and the sensing areas every 0.2 seconds.

Figure 9:
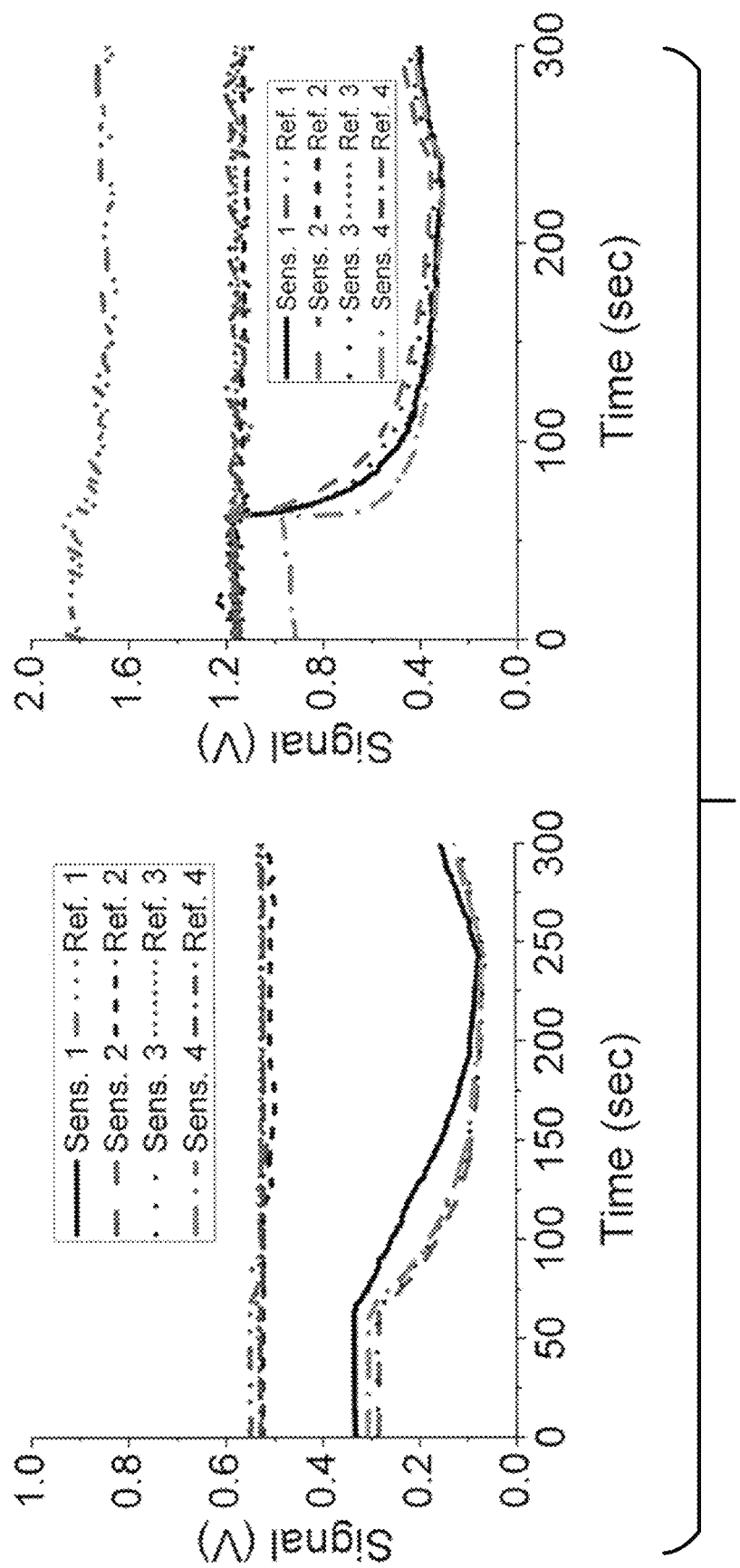
FIG. 9 illustrates graphs from a sensor for ammonia upon the exposure to ammonia. The graphs show the signal of the photodiodes related to an aspect of the present disclosure, operating as sensing photodiodes and reference photodiodes.

FIG. 9 illustrates the results of Example 3 and in particular the change in the sensor signal before and after exposure to ammonia ($NH_3$). The reproducibility of the sensors was determined using (a) four different PVDF sensors to detect 2 ppm ammonia ($NH_3$) and (b)4 different PTFE sensors to detect 40 ppm of ammonia ($NH_3$) using the analyzer device. The four different substrates show similar signal response. The PTFE response signal has a higher noise compared to PVDF substrate.

The absorbance was calculated based on Beer's Law by taking the negative logarithm of the signal response from the sensing area ($S_{sens.}$) divided by the signal response from the reference area ($S_{ref.}$) as follows in Equation 1:

$$\text{Absorbance} = -\log_{10}\left(\frac{S_{sens.}}{S_{ref.}}\right) \quad (1)$$

PTFE and PVDF sensors were cut into a rectangular shape using a laser cutter (Universal Laser Systems) and then laminated with Fellowes Jupiter 125 Laminator. Calibration curves for PTFE were built for a concentration range of 2-1000 ppm for ammonia ($NH_3$) by plotting measured absorbance change versus known concentration of the sample.

In order to ensure there was no interference between PD readings from the sensing and reference areas of the sensor, a cross-talking test was performed. In this test, either the reference area or the sensing area was individually masked with thick black ink to block light. The measurement was conducted for 30 seconds to check if the response was zero for the blocked area and unaffected for the unblocked sensor area. The cross-talking test results are shown in Table 1 and 2.

TABLE 1

Cross-talking measurement table of a PVDF sensor substrate

|  |  | Average (V) | Standard Deviation (V) | error (%) |
|---|---|---|---|---|
| Original | Sensing | 0.30 | 0.002 | 0.75 |
|  | Reference | 0.54 | 0.002 | 0.45 |
| black sensing | Sensing | 0 | 0 | N/A |
|  | Reference | 0.46 | 0.003 | 0.7 |
| black ref. | Sensing | 0.30 | 2.5*10^−4 | 0.08 |
|  | Reference | 0 | 0 | N/A |

TABLE 2

Cross-talking measurement table of a hydrophobic PTFE sensor substrate

|  |  | Average (V) | Standard Deviation (V) | error (%) |
|---|---|---|---|---|
| Original | Sensing | 1.654 | 0.004 | 0.75 |
|  | Reference | 1.571 | 0.004 | 0.45 |
| black sensing | Sensing | 0 | 0 | N/A |
|  | Reference | 1.761 | 0.002 | 0.7 |
| black ref. | Sensing | 1.651 | 0.015 | 0.08 |
|  | Reference | 0 | 0 | N/A |

For both masked substrates, the cross-talking test shows a minor signal change (<0.1% for sensing area and <15% for reference area), that was not significantly important under sensing conditions, and could be further improved by creating a thicker barrier between PDs or decreasing the distance from the sensor to the detector.

Example 4: Optoelectronic Instrument

Figure 10:
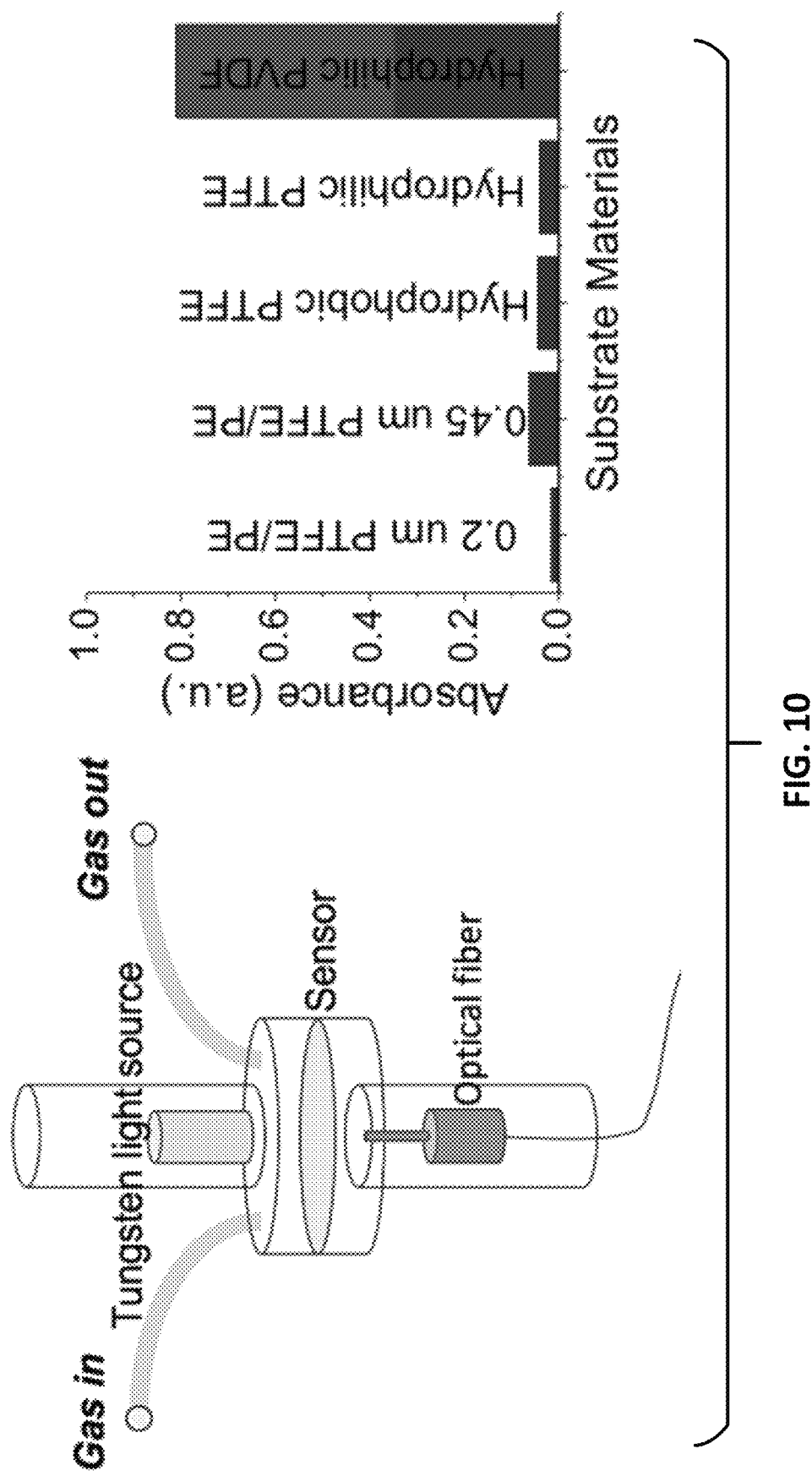
FIG. 10 illustrates a schematic diagram and a graph of experimental data related to the sensor substrate of the present disclosure.

A JAZ Spectrophotometer (JS) from Ocean Optics was used to conduct the sensitivity tests for the different sensor materials and spectrum measurement before and after exposure to ammonia ($NH_3$). FIG. 10 presents a schematic of the JS measurement device. The optical fiber is on the top of the chamber, while the tungsten light source is at the bottom of the chamber. The gas travels from the left tube and discharges into ambient environment from the right tube. The responses of the sensors synthesized with different materials after exposure to 10 ppm of ammonia ($NH_3$) for 180 seconds were measured by the JS. PVDF demonstrated a superior absorbance response compared to the other materials.

Figure 11:
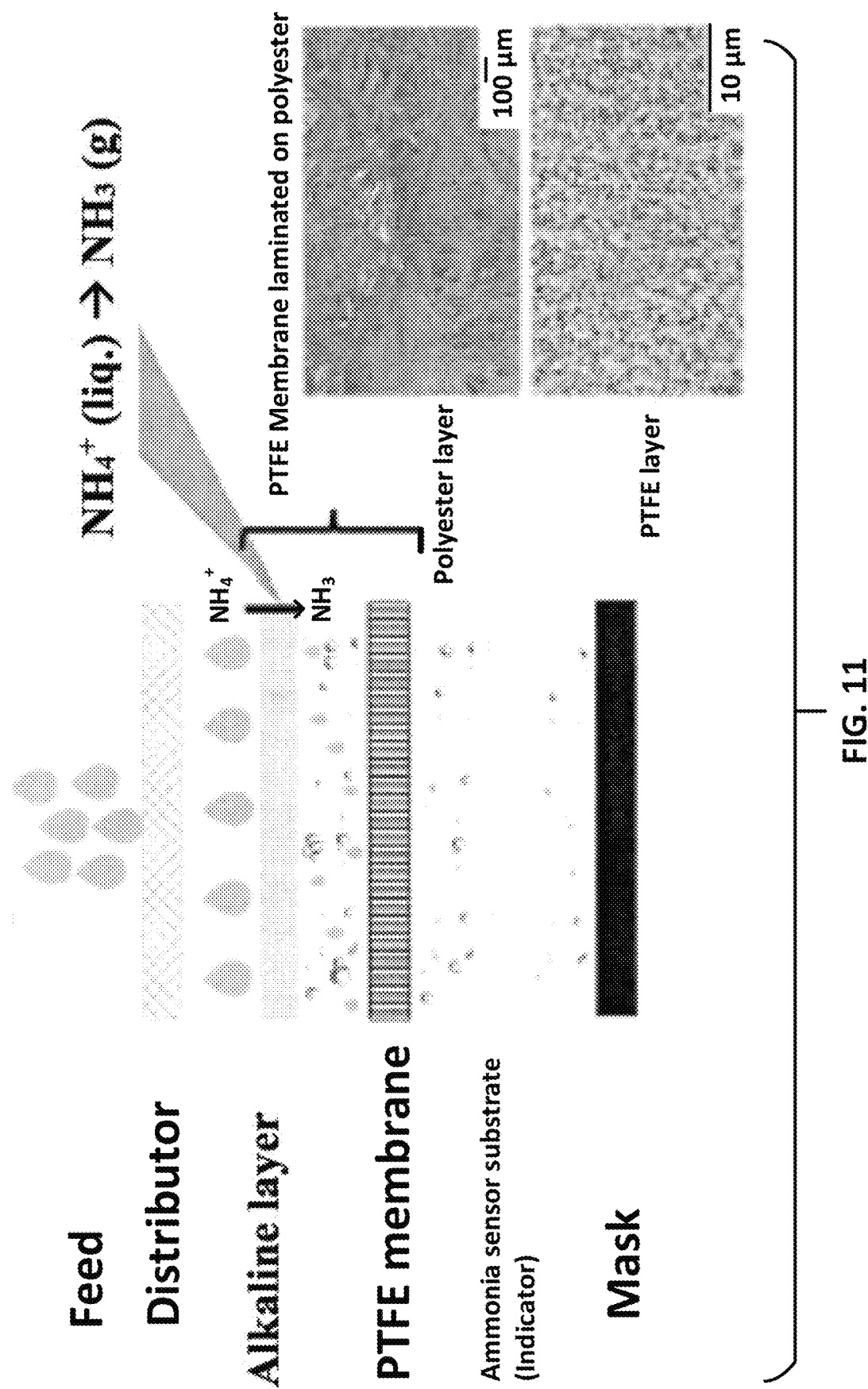
FIG. 11 illustrates a schematic diagram of an integrated analyzer for total ammonia (ammonium ($NH_4$) and ammonia ($NH_3$)) related to an aspect of the present disclosure. Note the optical color detector is not shown.

Filter paper was cut into a round shape to fit the JS sensing chamber. An ammonia ($NH_3$) sensor integrated with an ammonia ($NH_3$) extraction membrane was used for spectrum measurement. A schematic representation of the sensor and sample delivery from the liquid fluid to the gas that is measured is shown in FIG. 11. The extraction membrane/sensor assembly consisted of five parts: 1) the distribution layer (e.g., filter paper), which ensured the liquid fluid dispersed homogeneously, 2) the alkalinizing membrane layer (e.g., PE film impregnated with 40 μL of 2M NaOH solution), which extracted ammonia ($NH_3$) from the sample, 3) the polytetrafluoroethylene (PTFE) membrane, which precluded liquid fluid from reaching the indicator layer, 4) the indicator layer (filter paper impregnated with Bromothymol Blue), which reacted with the extracted ammonia ($NH_3$), and 5) the mask made of tape, which protected the sensing probe. A synthetic urine feed (ammonium ($NH_4^+$) solution with other ions simulating urine: NaCl, $KH_2PO_4$, $CaCl_2$, $MgSO_4$) was injected from the top of the integrated ammonia ($NH_3$) sensor membrane. The JS quantified the ammonia ($NH_3$) level in the sample. The ammonia ($NH_3$) sensing mechanism is further discussed below.

The distributor disperses the feed of the sample homogeneously. The alkaline layer converts the fluid's ammonium ($NH_4^+$) into its conjugate base, ammonia ($NH_3$). The PTFE membrane selectively filters the ammonia ($NH_3$) gas based on the hydrophobicity of the membrane. The ammonia ($NH_3$) sensor has an indicator that changes in color from yellow to blue based on how much ammonia ($NH_3$) gas it is exposed to.

Example 5: Optoelectronic Sensor Signal

As mentioned previously, Bromophenol Blue (BpB) was used as a colorimetric sensing probe for ammonia ($NH_3$) detection. A BpB solution has a yellow/orange color when it is exposed to a pH level below 3 and a blue color when exposed to a pH above 4.6. The acid/base equilibrium between ammonium ($NH_4^+$) (acid) and ammonia ($NH_3$) (conjugate base) is determined by the pH of the solution in the overall reaction $OH^- + NH_4^+ \leftrightarrow H_2O + NH_3$. Ammonia ($NH_3$) has a vapor pressure of 1062 kPa and a pKa of 9.25 at room temperature. Biologically relevant pH conditions are below the pKa of the $NH_4^+/NH_3$ equilibrium. For example, at a relatively high human urine pH of 8, only 6.6% of the total $NH_4^+/NH_3$ is present as $NH_3$ (gas). Because of the dynamic nature of biological fluid pH (e.g., urine) and the variable ratio of urine $NH_4^+$ to urine $NH_3$, an alkaline solution is needed to increase the fluid sample pH greater than ~10 to ensure 100% conversion of $NH_4^+$ (liquid) to $NH_3$ (gas). Ammonia ($NH_3$) causes the sensing surface to become more alkaline, shifting the pH value higher and causing a yellow to blue color transition. By quantifying the color change using the analyzer device (CODA), we can determine the corresponding ammonia ($NH_3$) concentration derived from the sample.

Example 6: Gas Sample Preparation—Ammonia Bags

The ammonia ($NH_3$) gas samples used in this work were diluted with 100 ppm and 1000 ppm calibration ammonia ($NH_3$) gas purchased from Calibration Technologies, Inc. Dilutions of gas samples in laboratory compressed air were prepared from 100 and 1000 ppm of ammonia ($NH_3$) calibration gas. These calibration gases were directed into a 40 L bag using a micro diaphragm gas pump from TOPSFLO (flow rate: 1.6 LPM) for a predetermined amount of time. Additional clean air was also directed into the bag for a controlled amount of time until the concentration of ammonia ($NH_3$) in the bag reached the desired level. The target ammonia ($NH_3$) gas concentration was prepared by manipulating the ratio of time of ammonia ($NH_3$) gas injection to air injection (between 0.02-0.8). An alternative ammonia ($NH_3$) bag was prepared by injecting 5 μL of ammonium hydroxide ($NH_4OH$) in a 1 L Tedlar™ bag and left in ambient room temperature for 30 minutes to validate the calibration curve for the sensors.

Example 7: Gas Sample Preparation—Urine Headspace Bags

A test sample of urine was preconditioned by adding 0.3 mL of 10 M NaOH to a 2.7 mL sample of urine, to ensure that the pH of the sample was greater than 12. The preconditioned urine sample was subsequently added to a 4 L Tedlar™ bag and purged with dry air until the bag was full. The Tedlar™ bag was left at ambient room temperature for 30 minutes to ensure that all of the ammonium ($NH_4^+$) in the urine reacted with the base and turned into its conjugated phase ammonia ($NH_3$) in urine headspace. Subjects of this part of the study were approved by the Institutional Review Board of Arizona State University (IRB protocol #1012005855). The test subjects participated voluntarily, providing written consent to participate in the study. All tests for this study were conducted from February 2016-July 2017. The subjects drank "ON High Protein Gainer protein shake" at 1 g of protein per Kg of body mass and urinated periodically after drinking. Urine samples were collected and stored immediately in a −80° C. freezer for later analysis.

Example 8: Sensor Detection Procedure

The sensitivity, reversibility, and reusability of the ammonia ($NH_3$) sensors were tested using an ammonia ($NH_3$) flow system, which contains a micro diaphragm gas pump (flow rate: 1.6 LPM), a three-way valve, one 40 L air bag, one 40 L sample bag, and the sensing chamber. Tests were conducted by placing one sensor in the sensing chamber each time. The three-way valve was first switched to connect with the air bag for a few seconds so that the sensor could be purged in air before it was exposed to the sample for a few seconds. In order to study the sensitivity of the sensor for different sample exposure times, sampling times varied, including 1, 5, 20 and 180 seconds. After exposure to ammonia ($NH_3$), the valve was switched to allow dry air to pass through the system for a few seconds to test sensor reversibility.

Example 9: Results and Discussion—Choice of Colorimetric Optoelectronic Dynamics Analyzer (CODA) Wavelength The color of the light source for the analyzer device, optionally named Colorimetric Optoelectronic Dynamics Analyzer (CODA), was selected based on the spectral changes ammonia (NH$_3$) exposure induced on the sensing probe (BpB). Round sensors made of filter paper impregnated with BpB were placed in the sensing chamber of the JS instrument, and the spectrum of each sensor was recorded before and after exposure to ammonia (NH$_3$). FIG. 4 shows visible spectrophotometric changes of a BpB-based sensor, and significant increases of absorbance in the range of 575-625 nm are clearly observed. Based on these results, the LED color was chosen to be red, wavelength: 610 nm. Once the detection wavelength and the first screening of sensor substrate were chosen, the analyzer device, CODA, was constructed and used to proceed with the rest of the study.

Example 10: Results and Discussion—Sensing Probe Sensitivity

Table 3 shows the properties of different sensing substrates embedded with BpB, and FIG. 10 summarizes the sensitivity of the sensing substrates tested in the JS instrument after 180 seconds of exposure to 10 ppm ammonia (NH$_3$) gas. The sensitivity of the sensor to ammonia (NH$_3$) is strongly dependent on the substrate nature. The graph in FIG. 10 shows that the PVDF substrate has the greatest measurement sensitivity, about ten times larger than all other substrates tested. The normal total ammonia (ammonia (NH$_3$) and ammonium (NH$_4^+$)) concentration range in urine is typically greater than 6 mmol/L, which yields (following a complete ammonium (NH$_4^+$) to ammonia (NH$_3$) conversion and ammonia (NH$_3$) gas extraction), an ammonia (NH$_3$) gas concentration in the urine headspace greater than 100 ppm at temperature 25° C. based on ideal gas law. The high sensitivity of PVDF precludes using the sensor multiple times because of a rapid saturation of the sensor in a single use. Therefore, the sensitivity, specificity, and reversibility features of another substrate, hydrophobic PTFE, were explored in comparison to PVDF for urine ammonia (NH$_3$) monitoring.

TABLE 3

Properties of different substrate materials for the ammonia sensor

|  | *PTFE | PTFE/PE-1 | PTFE/PE-2 | *PTFE | *PVDF |
|---|---|---|---|---|---|
| Pore size (um) | 10 | 0.2 | 0.45 | 0.1 80% | 0.1 70% |
| Thickness (um) | 177.8 | 152.4–254 | 152.4–254 | 30 | 30 |

*These materials are relatively more hydrophilic

Example 11: Results and Discussion—Reproducibility of Sensor Response

Figure 12:
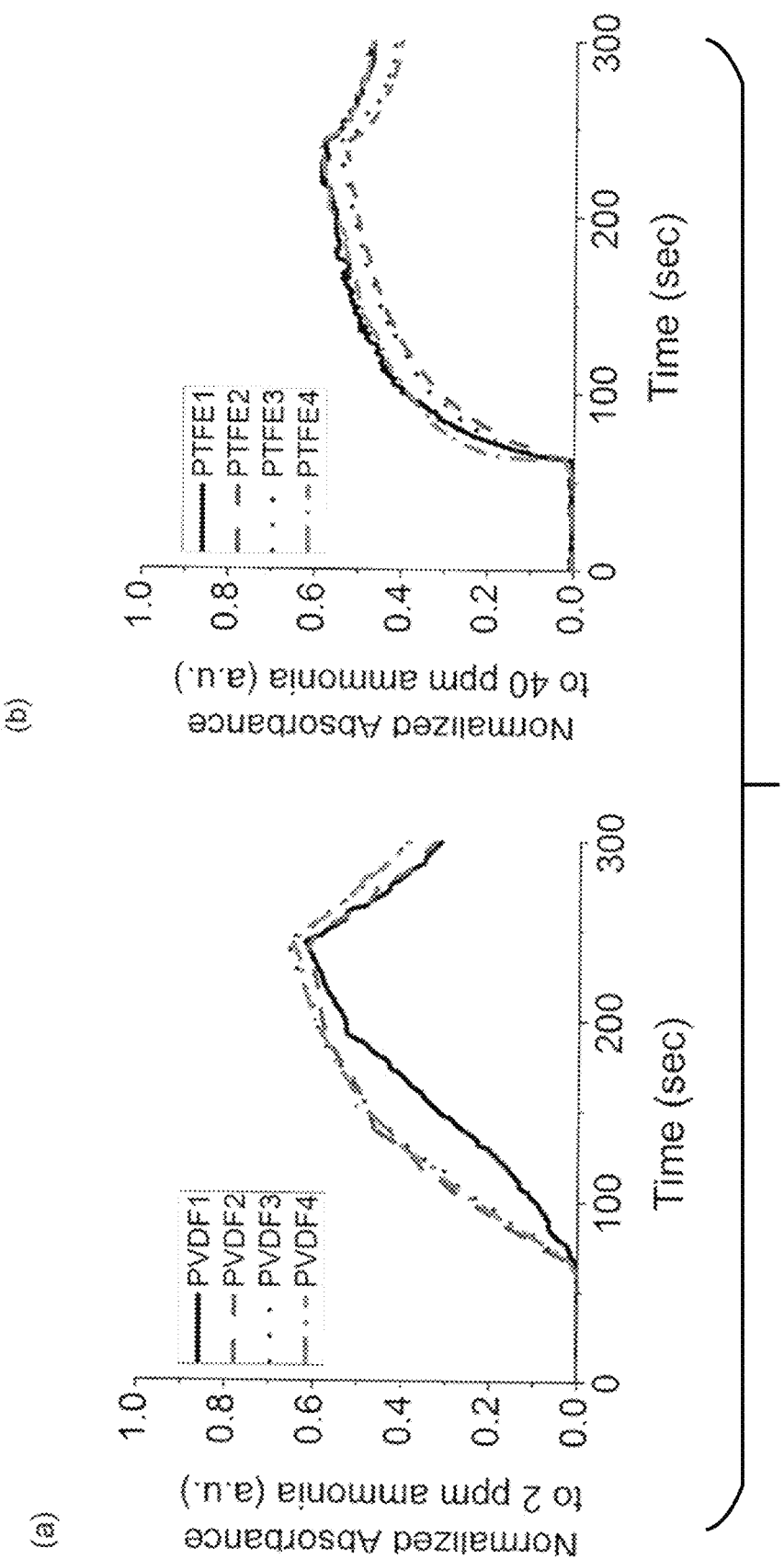
FIG. 12 illustrates graphs of ammonia sensor signals related to an aspect of the present disclosure.

FIG. 12 compares the absorbance response of sensors based on PTFE and PVDF support materials as used in the CODA. Four replicate sensors were made with each material and placed in the CODA. Next, the sensors were exposed to ammonia (NH$_3$) for 180 seconds followed by dry air for additional 60 seconds to determine recovery. The sensors show similar response characteristics with rising absorbance upon the injection of ammonia (NH$_3$) and decreasing absorbance upon purging with dry air. The absorbance noise for the PTFE substrates was higher in comparison to the PVDF substrate.

Table 4 summarizes the sensor responses and percentage of sensor recovery after purging, which is the ratio of the absorbance change during the recovery period to the absorbance change during the exposure period. The sensor responses included 0.64 a.u. with a standard deviation of 0.02 for PVDF, and 0.58 a.u. with a standard deviation of 0.03 a.u. for PTFE, and a response dispersion across sensor substrates of 5% or less. It is important to note that even though PVDF had similar reproducibility as PTFE, the smaller ammonia (NH$_3$) concentration required for comparison (20-times less concentrated ammonia (NH$_3$)) produced similar recovery percentages to PTFE. The recovery properties of the sensor response using PTFE at concentration ranges within a realistic urine-derived ammonia (NH$_3$) concentration range made PTFE a more attractive candidate for further study of the analytical performance of this sensor substrate. As a consequence, in the rest of this work, PTFE sensors were investigated.

TABLE 4

Reproducibility and Reversibility analysis

|  | PVDF | | PTFE | |
|---|---|---|---|---|
| Parameters N = 4 | Absorbance (a.u.)[1] | Recovery (%)[1] | Absorbance (a.u.)[2] | Recovery (%)[1] |
| Average | 0.64 | 45.5% | 0.58 | 36.2% |
| SD | 0.02 | 3.4% | 0.03 | 4.2% |
| Error (%) | 3.1% | 7.5% | 5.1% | 11.6% |

[1]The result is for 2 ppm ammonia (NH$_3$) detection in 3 minutes.
[2]The result is for 40 ppm ammonia (NH$_3$) detection in 3 minutes.

Example 12: Results and Discussion—Sensor Calibration to Ammonia (NH$_3$)

Figure 13:
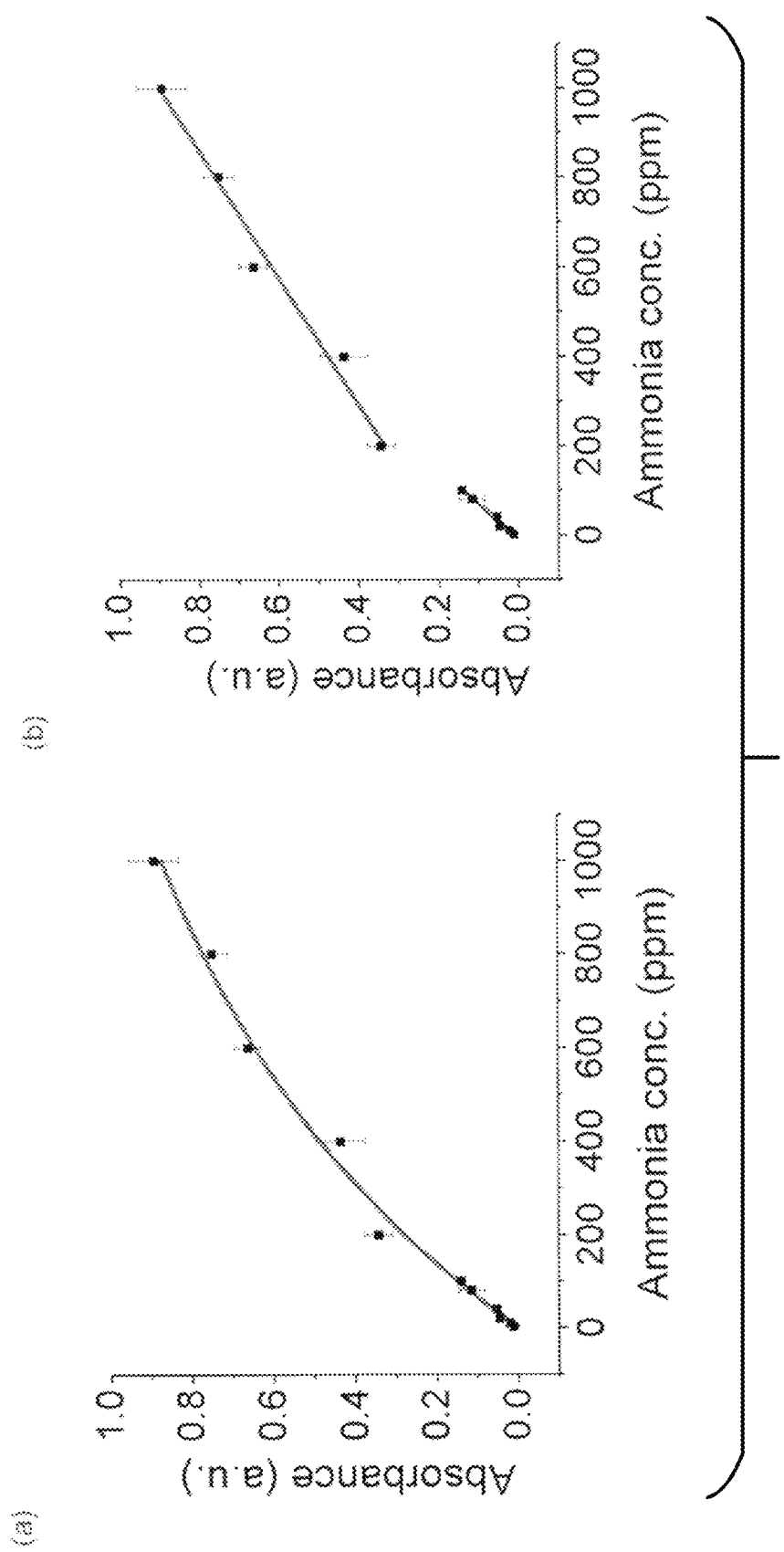
FIG. 13 illustrates calibration plots of the sensor for ammonia related to an aspect of the present disclosure.

As illustrated in FIG. 13, two calibration curves were developed for the PTFE sensors with the CODA, using 5 second sampling times with ammonia (NH$_3$) gas levels ranging from 2 ppm to 1000 ppm. In the first, top calibration curve, a Langmuir model was applied, and exhibited a $R^2$ value greater than 0.99. For the 5 second sampling times, the calibration equation is as follows, where $A^L$ represents the absorbance derived from Langmuir model and C represents the corresponding concentration:

$$(\text{Mod}) \frac{1.85\ C}{1 + 1122.28\ C} \qquad (2)$$

In the other, bottom calibration curve, the calibration curve was divided into two ranges for fitting linear regressions: 2-150 ppm and 150-1000 ppm. Both measurement ranges showed $R^2$ values greater than 0.98. The calibration equations are as follows, where $A^1$ represents the absorbance derived from linear model from 0-150 ppm, $A^2$ represents the absorbance derived from linear model from 150-1000 ppm, and C represents the corresponding concentration:

$$(\text{Mod}))\ .00131\ C + 0.01027\ \text{for}\ 0\ \text{ppm} < C \leq 150\ \text{ppm} \qquad (3)$$

$$(\text{Mod}))\ .0007\ C + 0.19445\ \text{for}\ 150\ \text{ppm} \leq C \leq 1000\ \text{ppm} \qquad (4)$$

In a different set of fittings, linear regressions for absorbance changes assessed at 1 second exposure of ammonia (NH$_3$) were also obtained, and compared to those obtained at 5 second exposure of ammonia (NH$_3$). These regressions were used to test an unknown sample concentration, resulting from a mixture of ammonium hydroxide (NH$_4$OH) and air inside a bag. Table 5 shows the results assessed for the unknown concentration sample by the sensor, using a 1- and 5-second sample exposure, and the corresponding calibration curves. Both calibration curves (from the 1-second and 5-second exposure data), yielded the same concentration of the prepared ammonia ($NH_3$) bag of unknown concentration, indicating self-consistency of the calibrations. Additionally, these results indicate consistency between each pair of photodiodes (PD1 (sensing)/PD3 (reference) shown as PD1 and PD2 (sensing)/PD4 (reference) shown as PD2) in the system, as both pairs of photodiodes yielded the same response.

TABLE 5

Ammonia ($NH_3$) concentration (ppm) output from calibrations performed with 1-sec and 5-sec sampling times in PTFE-based sensors

|  | 1 sec PD1[1] | 1 sec PD2[2] | 5 sec PD1[3] | 5 sec PD2[4] |
| --- | --- | --- | --- | --- |
| Run 1 | 868 | 875 | 956 | 932 |
| Run 2 | 980 | 1035 | 919 | 914 |
| Run 3 | 1018 | 998 | 1021 | 968 |
| Mean | 955 | 970 | 966 | 938 |
| Std. Dev. | 64 | 68 | 42 | 23 |

[1-2]Recovered with 1-second calibration curve from Photodiode 1, and Photodiode 2, respectively
[3-4]Recovered with 5-second calibration curve from Photodiode 1, and Photodiode 2, respectively Example 13: Results and Discussion—Sensor Selectivity to Ammonia ($NH_3$)

Figure 14:
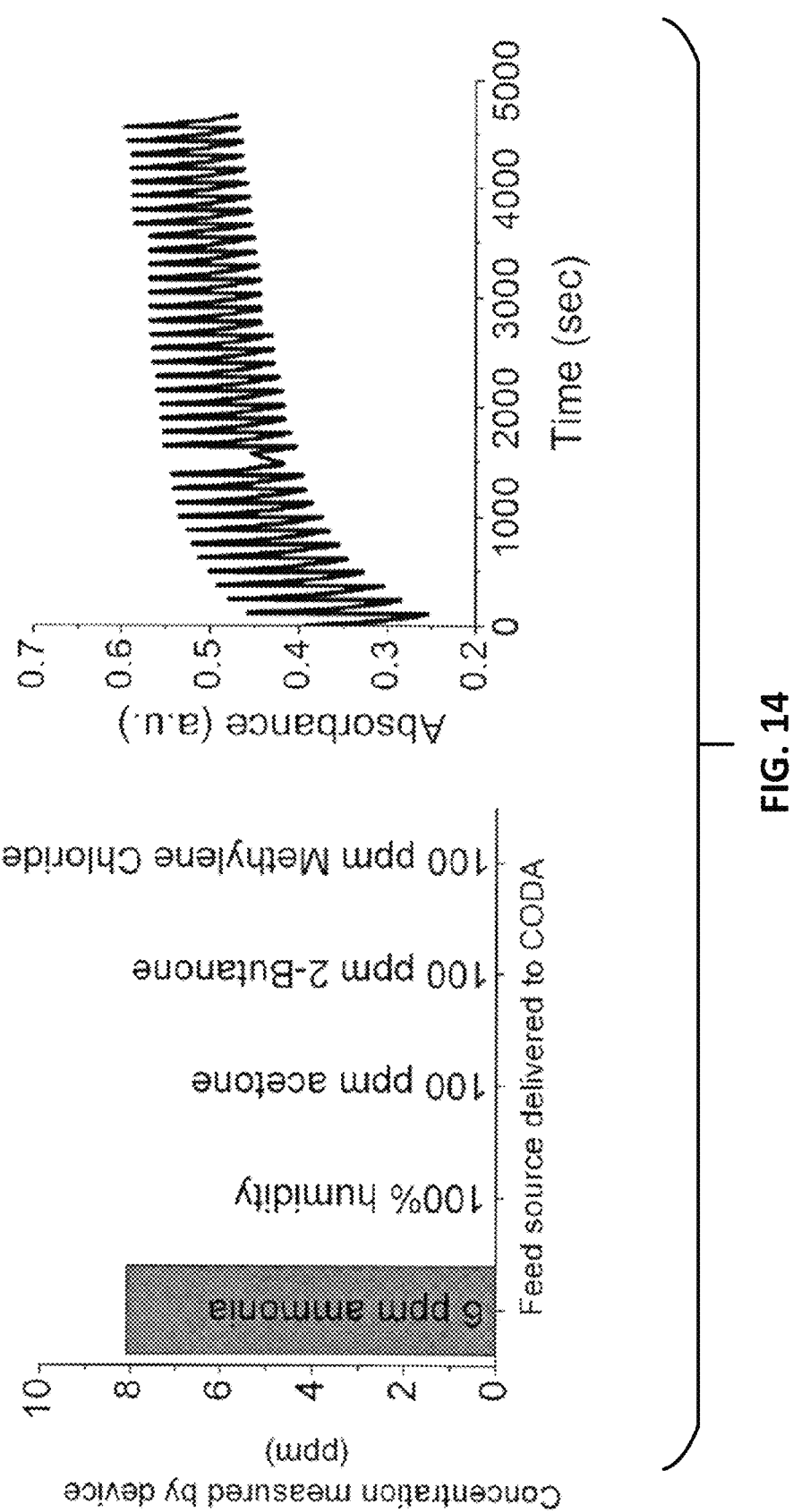
FIG. 14 illustrates graphs of experimental data assessed by total ammonia analyzer device (CODA) related to an aspect of the present disclosure, showing selectivity and response to consecutive sample analysis.

To confirm the sensor is only selective to ammonia ($NH_3$), the sensor was exposed to several interferents (e.g., acetone, 2-butanone, and methylene chloride) reported to exist in urine headspace. FIG. 14 shows the selectivity of the sensor to ammonia ($NH_3$). Even with relatively high concentrations of interferents (e.g. 100 ppm acetone), the sensor only showed a significant response to ammonia ($NH_3$). This test confirmed the selectivity of the sensor in the harsh environment of the urine headspace sample.

Example 14: Results and Discussion—Sensor Reversibility and Reusability

Figure 15:
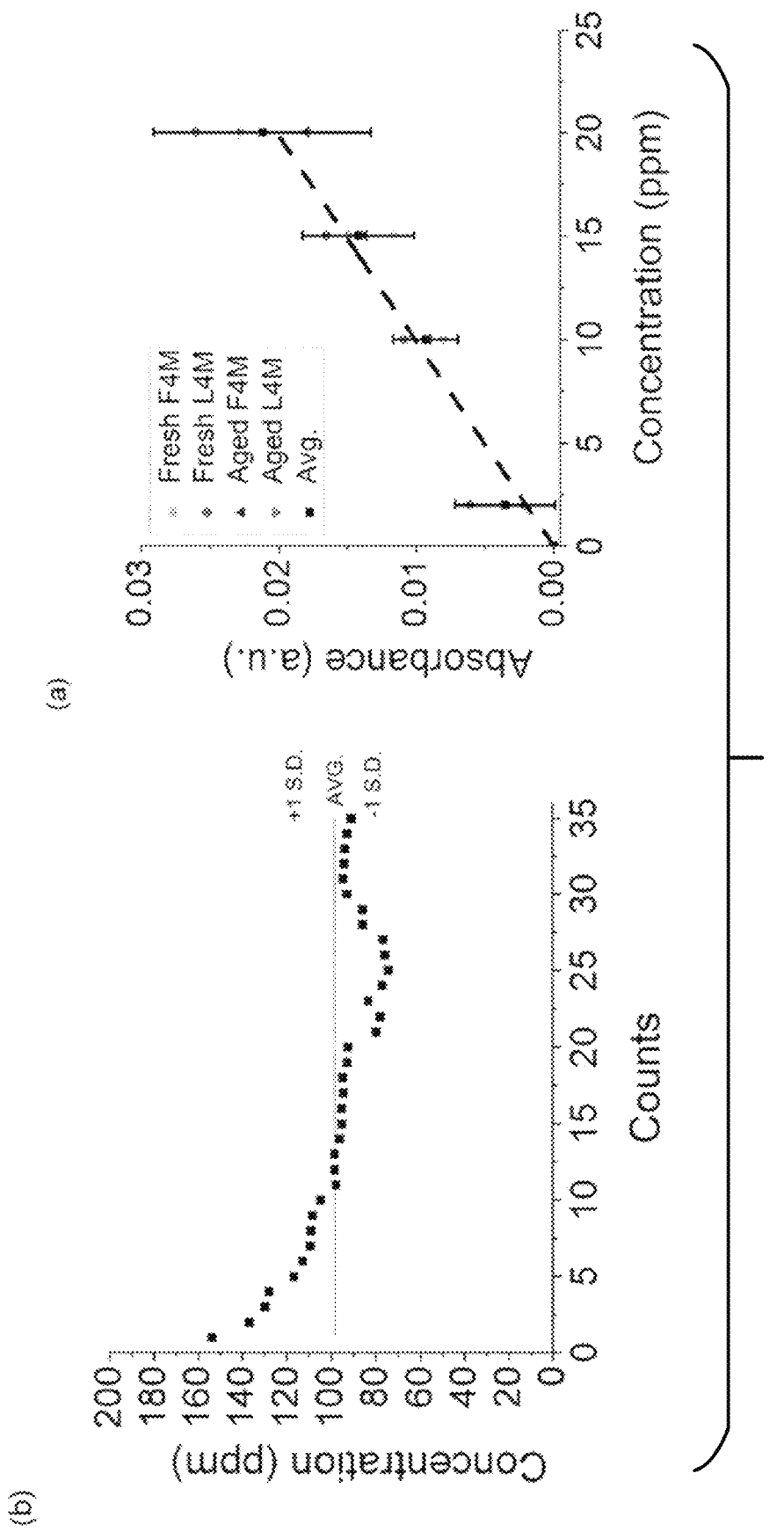
FIG. 15 illustrates graphs of experimental data assessed by total ammonia analyzer (CODA) related to an aspect of the present disclosure, showing total ammonia (as ammonia, $NH_3$) output, and accuracy of the device.

A healthy adult human may urinate every 2-3 hours (8-9 times per day). Current methods to quantify ammonium ($NH_4+$) in urine for clinical medicine include requiring a patient to collect all excreted urine for 24 hours. There is no clinically used method for instantaneous urine ammonia ($NH_3$) or urine total ammonia (ammonia ($NH_3$) and ammonium ($NH_4^+$)) measurement. The top panel of FIG. 15 shows the absorbance response of the PTFE-based sensor to alternating exposure to 100 ppm of ammonia ($NH_3$) and dry air repeatedly over 1.2 hours. The sensor was continuously exposed to a repeating cycle of ammonia ($NH_3$) for 5 seconds followed by dry air for 120 seconds. The sensor was re-used for over 60 detection cycles without degradation in performance. For practical, clinical application one 5-second ammonia measurement could be taken every 24 minutes to cover 24 hours of monitoring, although much more frequent testing is also possible.

The bottom panel of FIG. 15 shows the measured concentrations from the continuous test after signal analysis, and use of calibration equations. It is important to note that the sensor required a conditioning period of 5-7 exposures. After this conditioning period, the concentration output remained fairly constant throughout the multiple exposures to ammonia ($NH_3$) and detection events of the same concentration. The detection concentration error was lower than 20%, and could be further improved with a better enclosure of the CODA, which will decrease ambient light interference.

Example 15: Results and Discussion—Sensor Stability

Figure 16:
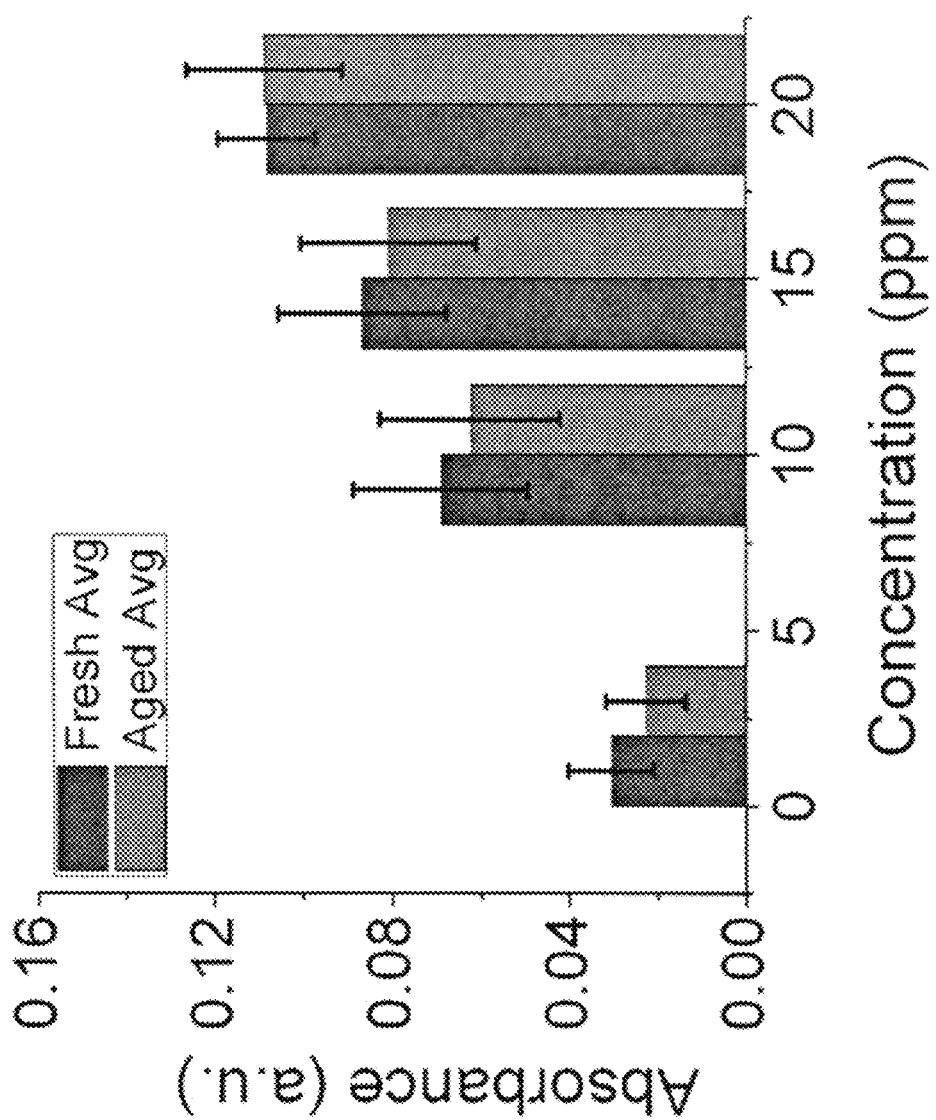
FIG. 16 illustrates a graph of experimental data related to an aspect of the present disclosure, showing the stability of the sensor for ammonia.

To test the stability of the PTFE sensor, a set of sensors was freshly prepared, and used in ammonia ($NH_3$) testing immediately after synthesis. An identical set of sensors was prepared, sealed in a black Mylar™ bag, and aged in a convection oven at 45° C. for 2 weeks. According to aging protocols (ASTM F1980), the 2 week aging at 45° C. is equivalent to 2 months aging at room temperature (25° C.). Both set of sensors were exposed to ammonia ($NH_3$) concentrations of 2, 10, 15, and 20 ppm. FIG. 16 shows the sensitivity comparison between the fresh and aged sensors. FIG. 16 shows all data and a linear regression of the averaged data. A slope of 0.001 a.u./ppm and a $R^2$ greater than 0.99 was obtained for the averaged data. FIG. 16 also shows another set of fresh and aged sensors from a different synthesis batch. A t-test between these responses from the membranes from each batch for the fresh and aged sensors yielded a p-value equal to 0.87, which indicated no significant difference. These tests confirmed the stability of the sensing probe (BpB) on the PTFE substrate upon prolonged exposure to heat, which is relevant to sensor application and storage. For commercial products, the sensor sensitivity needs to be guaranteed after periods of heat exposure, which may happen under real-life shipping or storage conditions.

Example 16: Results and Discussion—Sensor Use with Urine Samples

Figure 17:
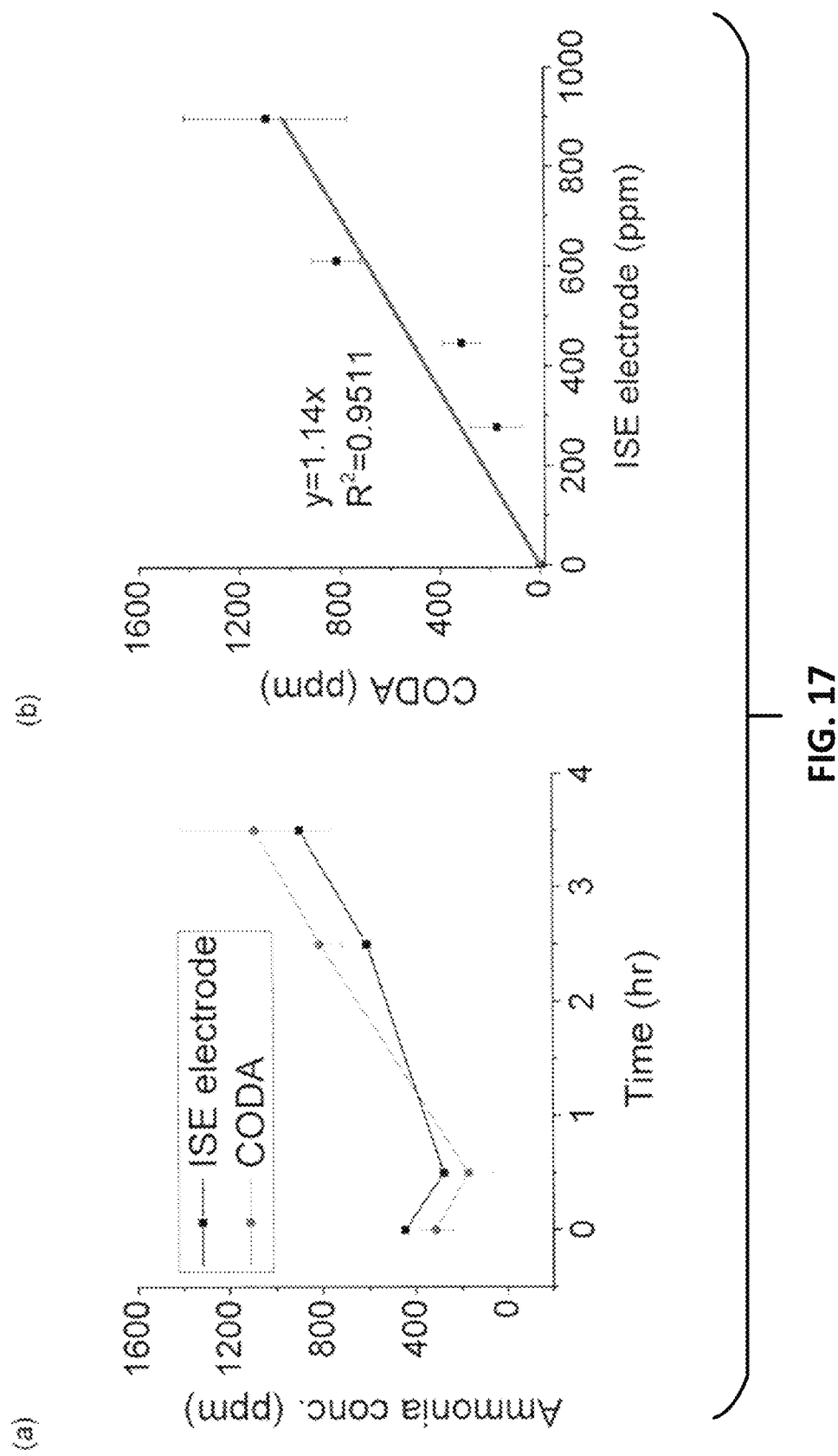
FIG. 17 illustrates graphs of experimental data related to an aspect of the present disclosure, showing a real body fluid analysis (urine) by the analyzer (CODA), and a reference method (Ion selective electrode (ISE)).

To confirm the feasibility of the CODA and its use of the sensor in real conditions, a urine sample analysis was performed and measurements were recorded from a calibrated batch of sensors. An ion selective electrode (ISE) [Ammonia High Performance Ion Selective Electrode (no. 9512HPBNWP) from Thermo Fisher Scientific] was used as a reference method for ammonia ($NH_3$) detection. Subjects were first asked to urinate and then to drink a protein shake. The subjects' urine samples were collected before and after drinking the shake at times of 0, 0.5, 2.5 and 3.5 hours. These samples were stored at −80° C. before measurement. Next, the samples were measured by the ISE electrode and afterwards measured with the CODA. The top panel of FIG. 17 presents an example of the measurements from one subject. A similar result can also be found in literature using SIFT-MS. The bottom panel of FIG. 17 shows a correlation plot of the results assessed from the CODA and ISE methods. A good agreement between the measurement with CODA and ISE electrode was found with accuracy close to 100%.

Figure 18:
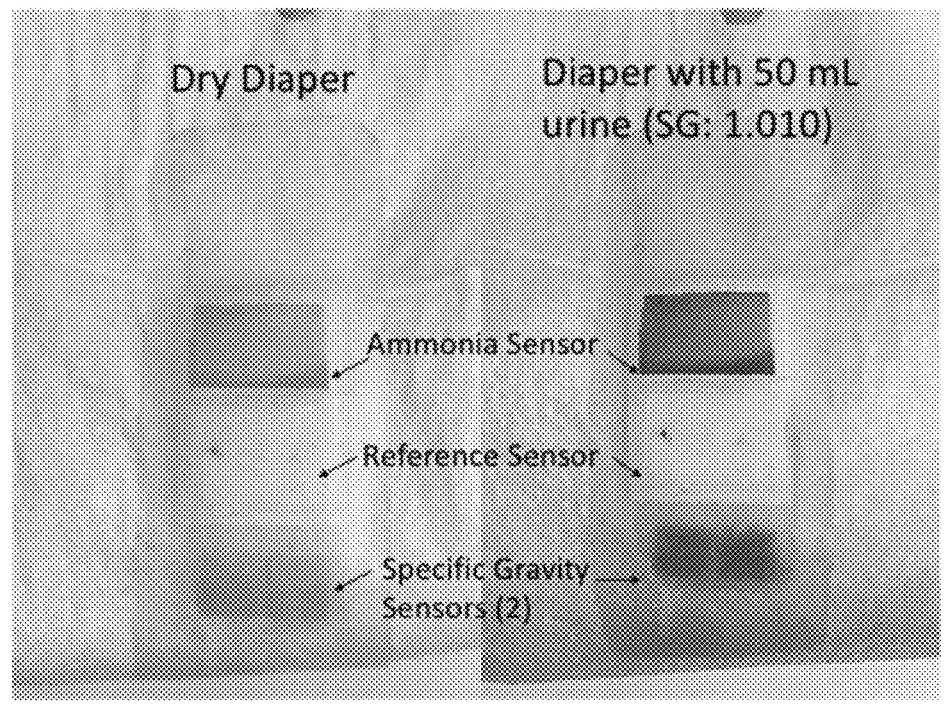
FIG. 18 illustrates sensor preparation in a diaper, and the detection of urine ammonia in the prepared diaper insert, related to an aspect of the present disclosure.
Figure 18:
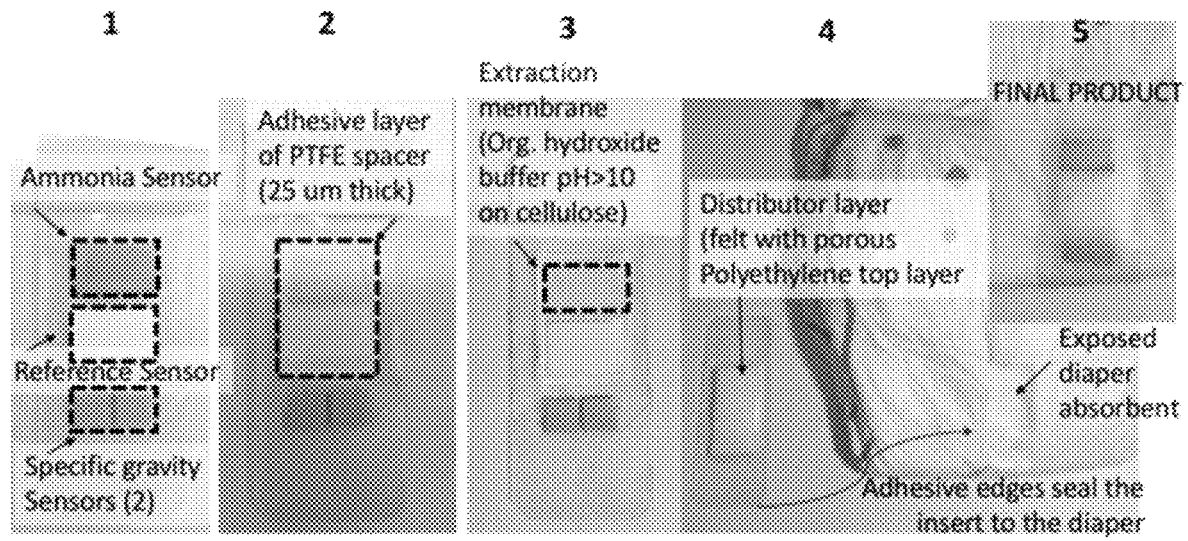

Example 17: Results and Discussion—Sensor Use with Urine Samples as Insert in a Diaper or Adhesive Patch or a Card As illustrated in FIG. 18, In some embodiments, the sensor described herein may be used in the shape of an insert for a diaper or wearable cloth. The use of the sensor with an extraction membrane may be implemented in the shape of an insert for a diaper or wearable cloth or device (e.g. bracelet) or an adhesive patch for the skin, or a card (e.g. badge) for in vitro testing. Under these conditions, the sensor reaction (i.e., change in color) quantitation due to the total ammonia (ammonia ($NH_3$) and ammonium ($NH_4^+$)) and/or ammonium ($NH_4^+$) in body fluid being detected as ammonia ($NH_3$) may be performed with any method capable of detecting small color changes, such as with RGB deconvolution software.

Example 18: Results and Discussion—Sensor Use with Continuous Samples

Figure 19:
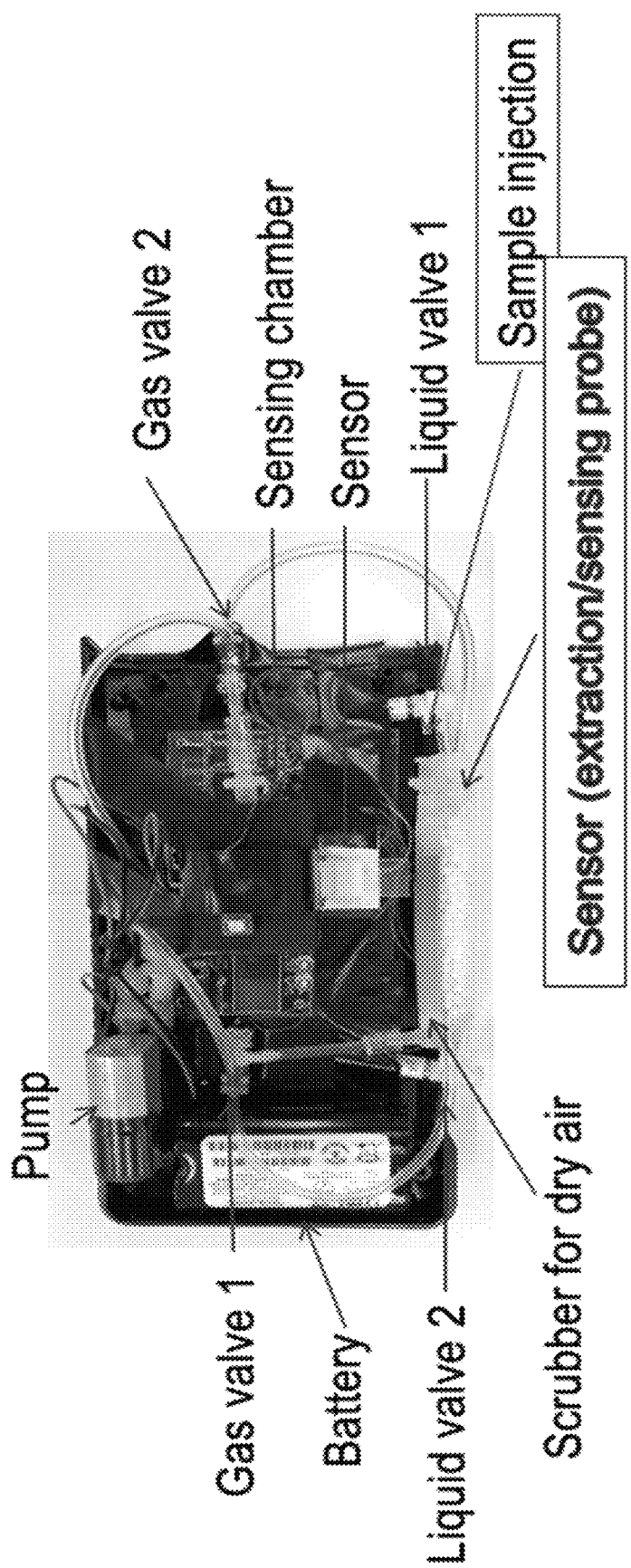
FIG. 19 shows the components of an example CODA for continuously monitoring ammonia in biological samples.

FIG. 19 shows the components of an example CODA device. In some embodiments, the sensor described here may be used for continuous ammonia monitoring from biological samples, while inserted into a device able to manage liquids from the sample and gases from the extraction process in the sensor, as well as to regenerate the sensor surface (sensing probe) with a clean source of air such as from a scrubber.

Figure 20A:
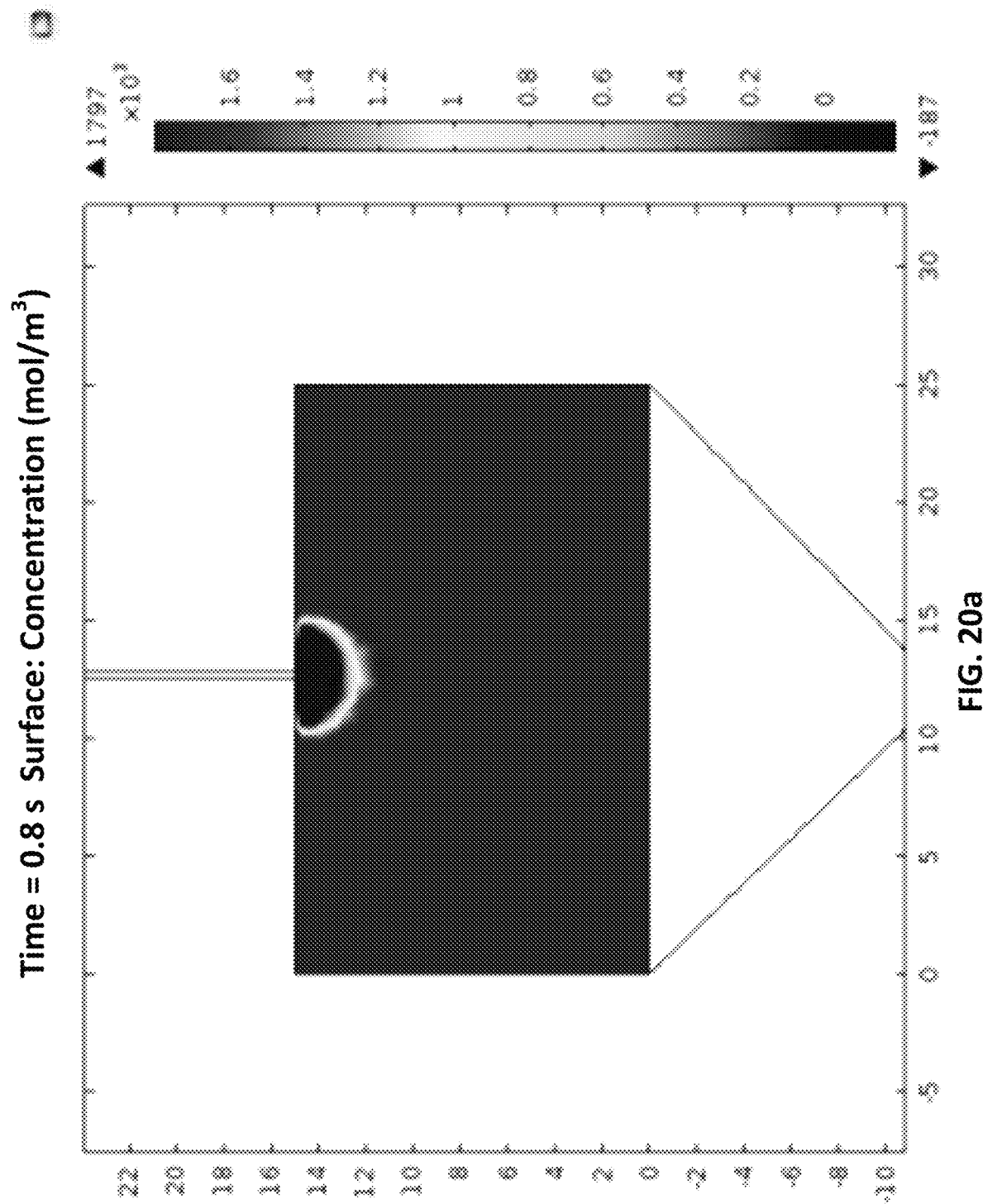
FIGS. 20a-20o show an example of a chemical extraction membrane and how different variables such as porosity, boundary conditions, initial $NH_4^+$ concentration in the sample, and geometry affect the concentration profile of the alkaline material in the extraction membrane.
Figure 20B:
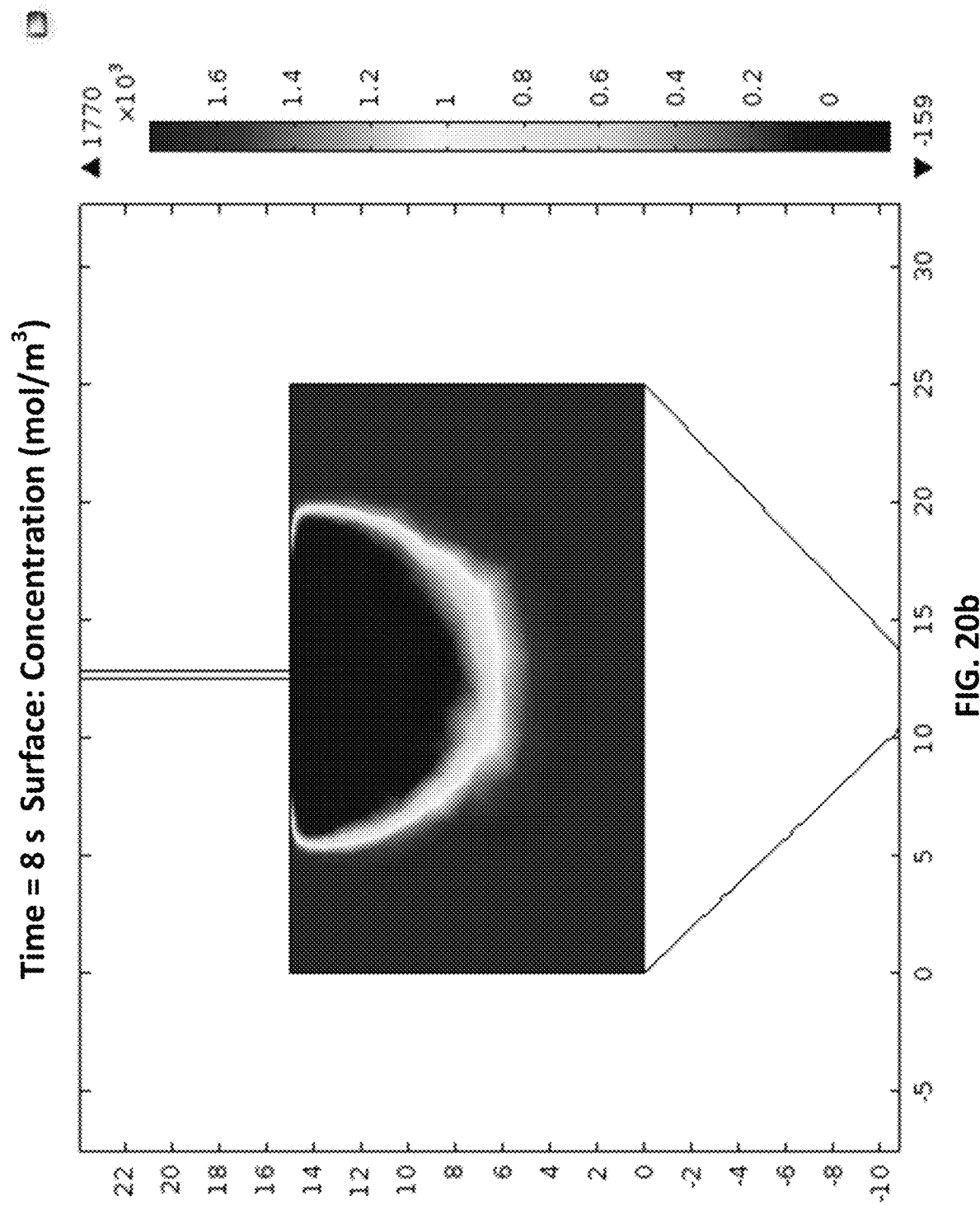
Figure 20C:
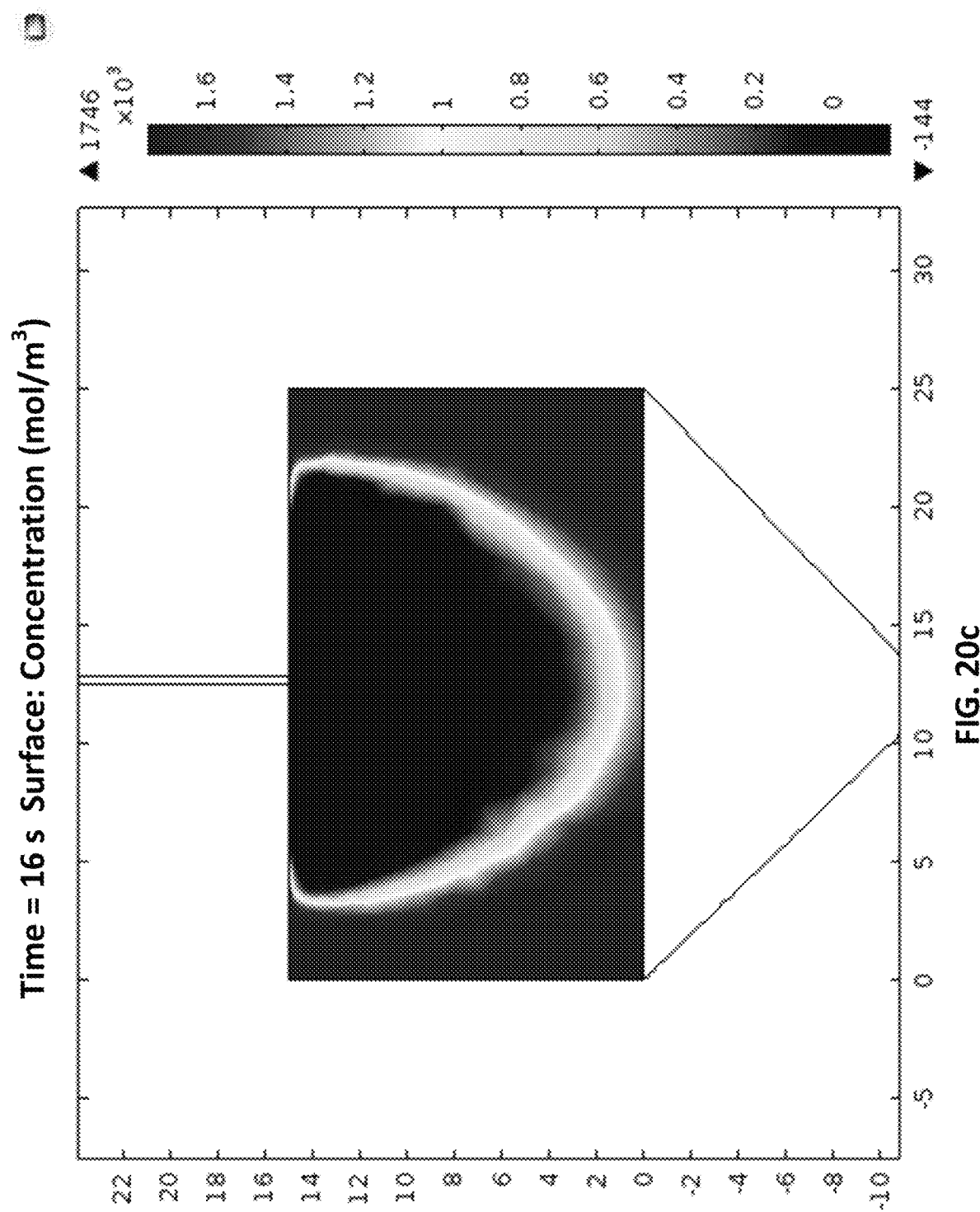
Figure 20D:
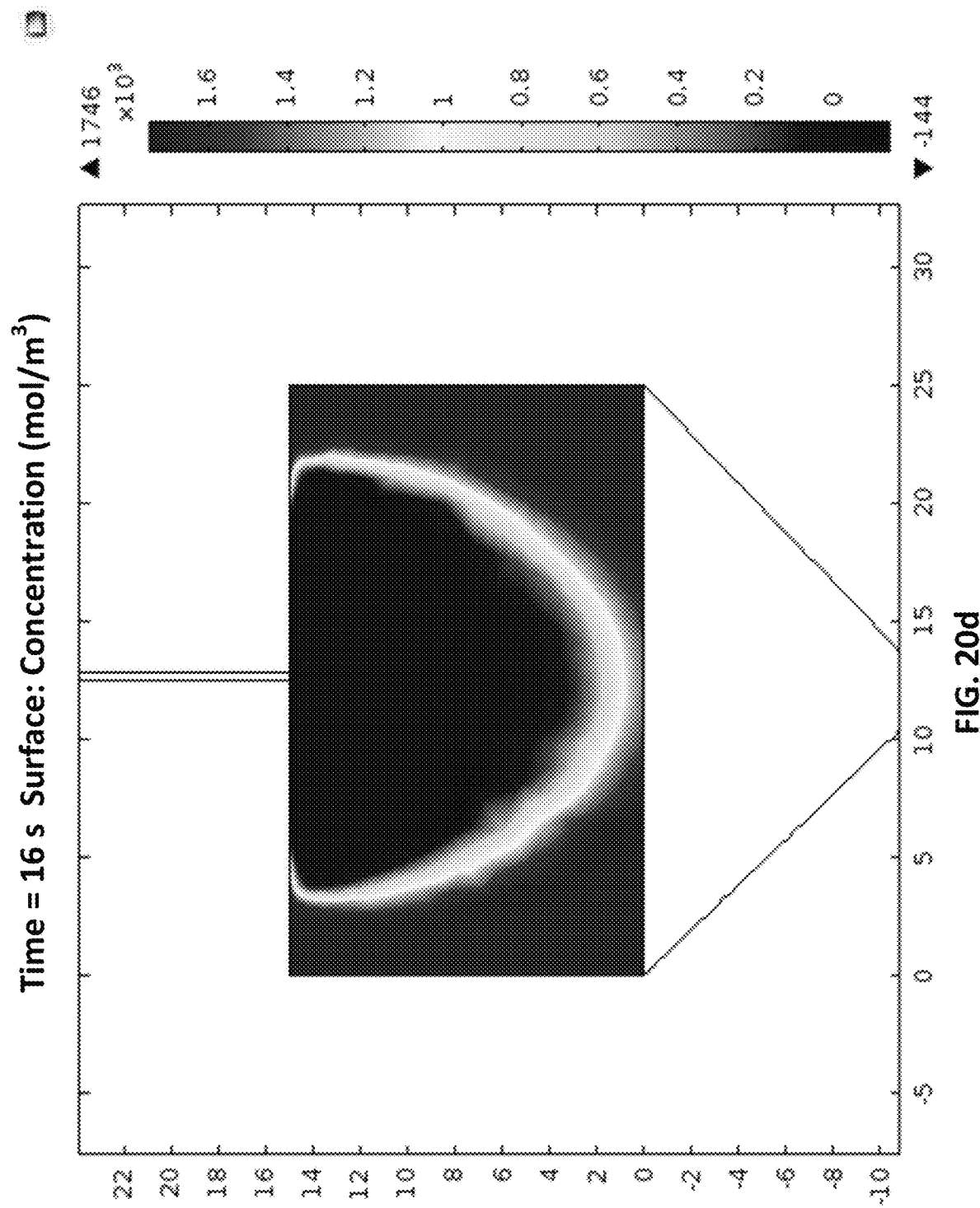
Figure 20E:
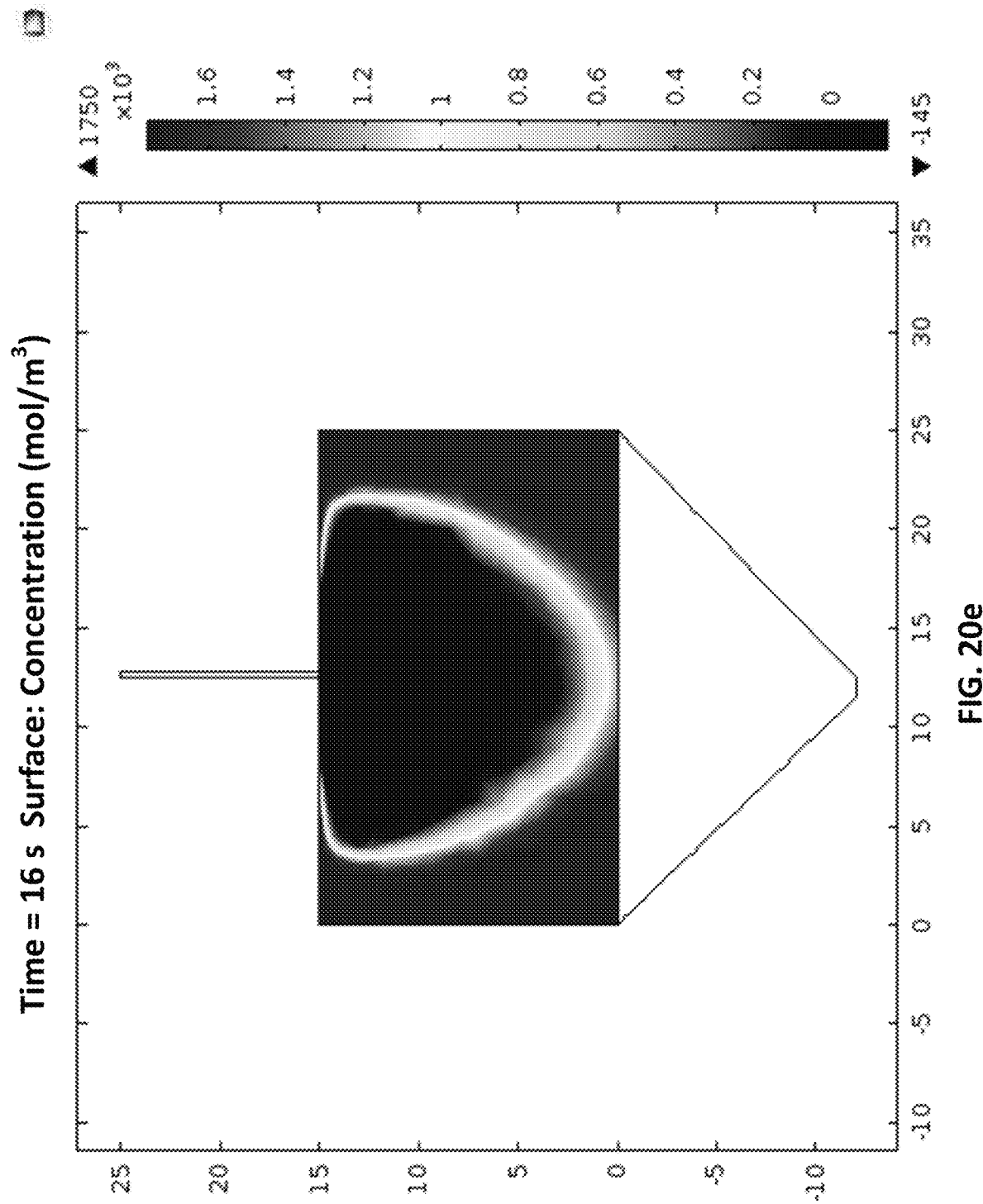
Figure 20F:
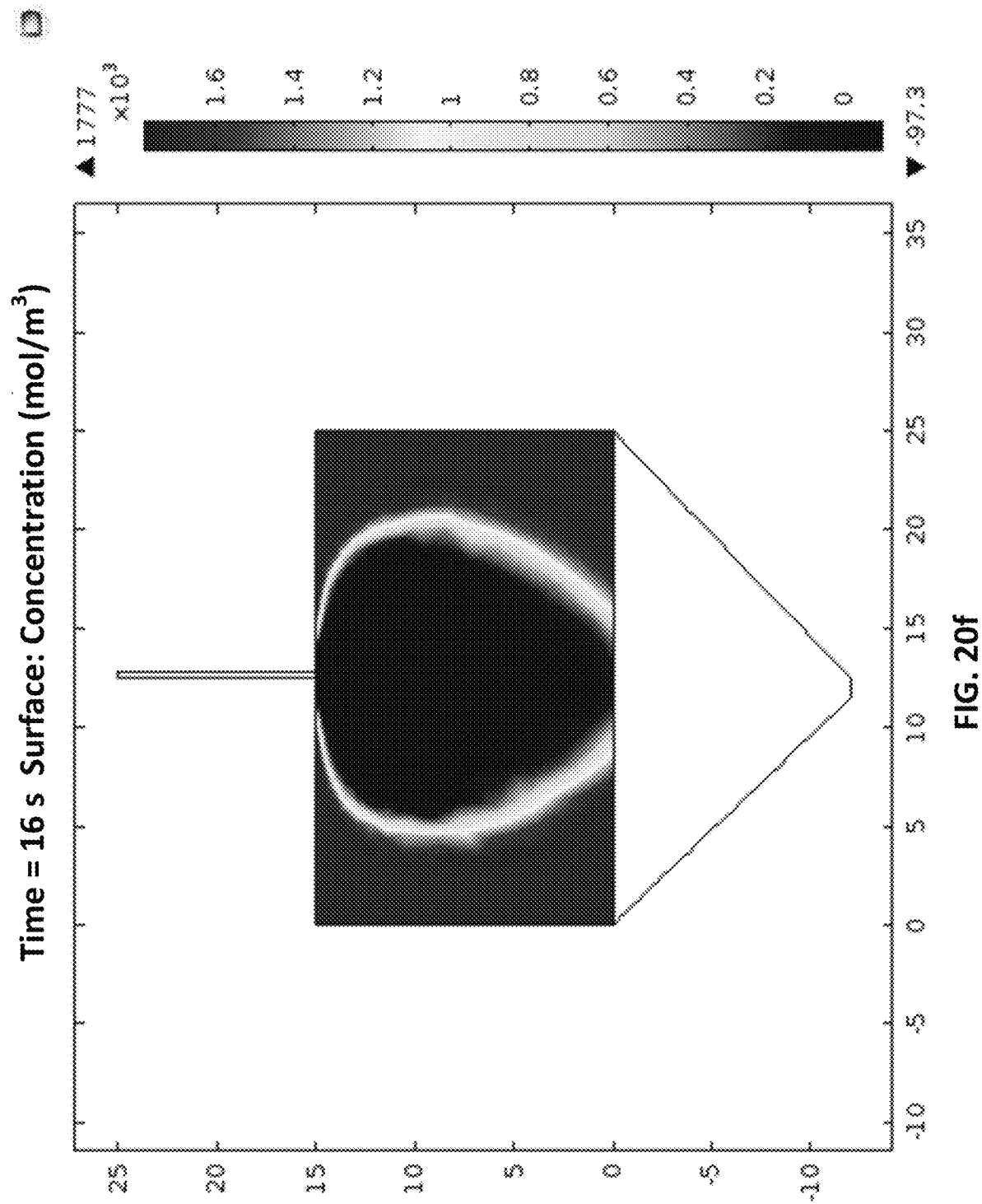
Figure 20G:
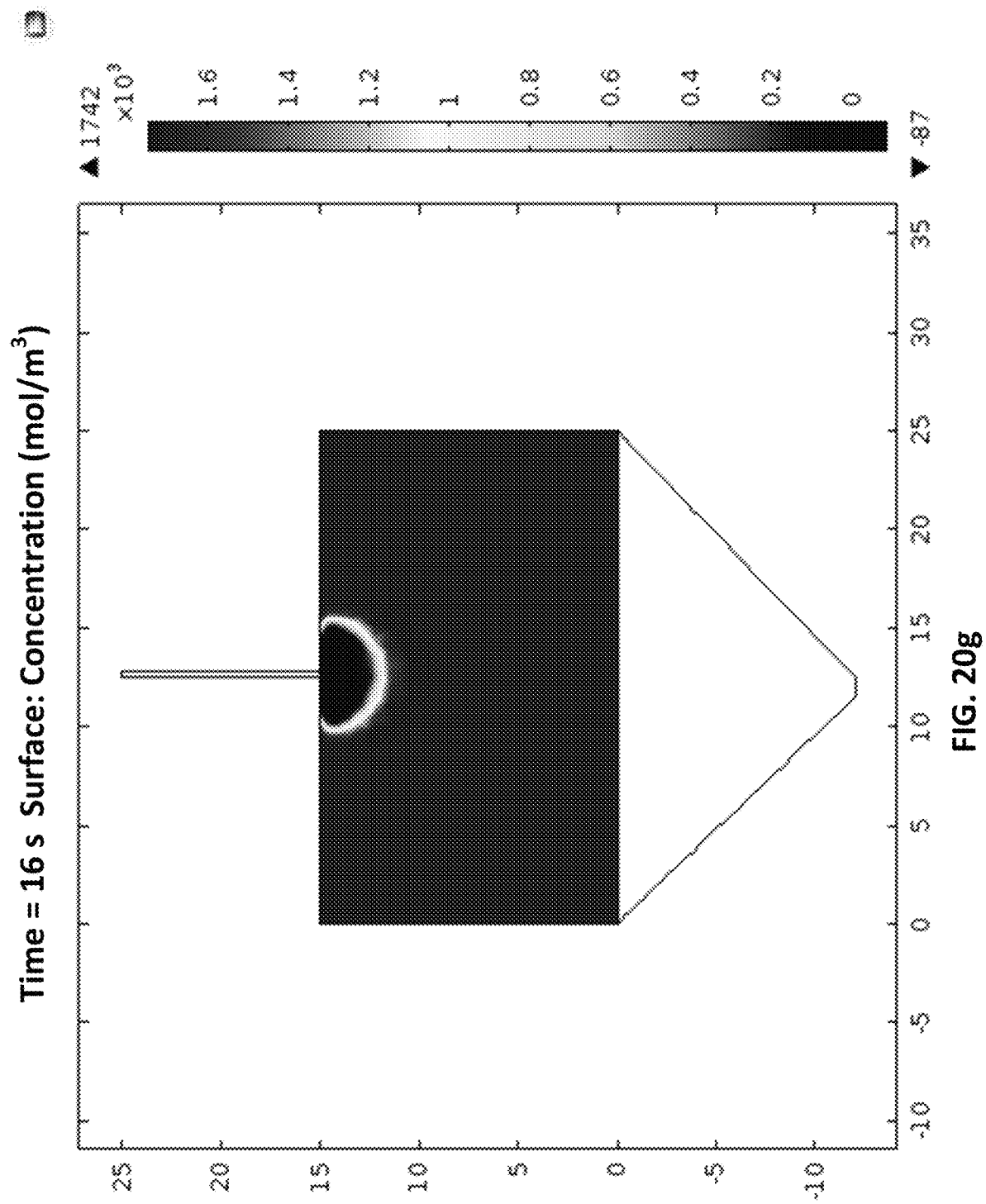
Figure 20H:
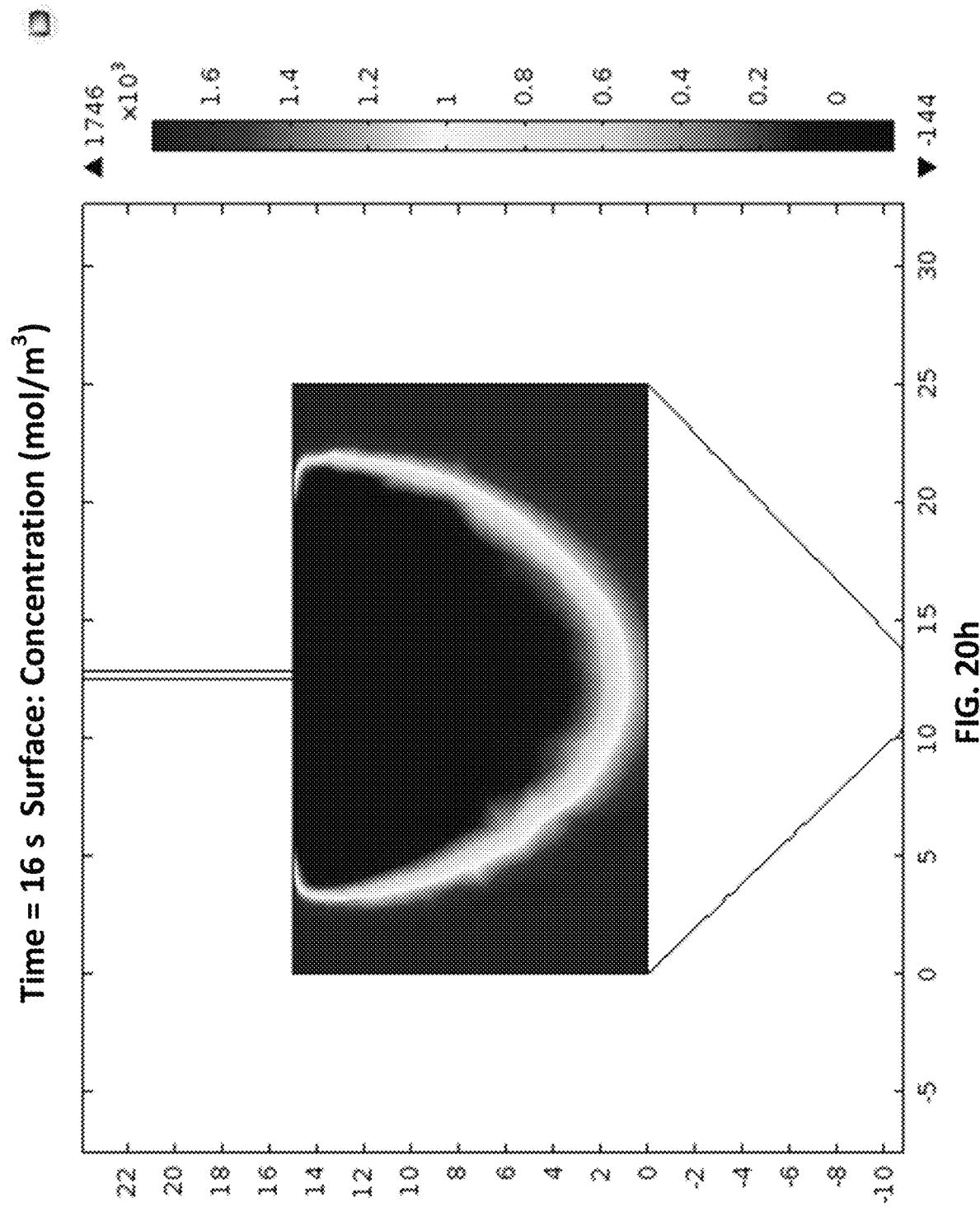
Figure 20I:
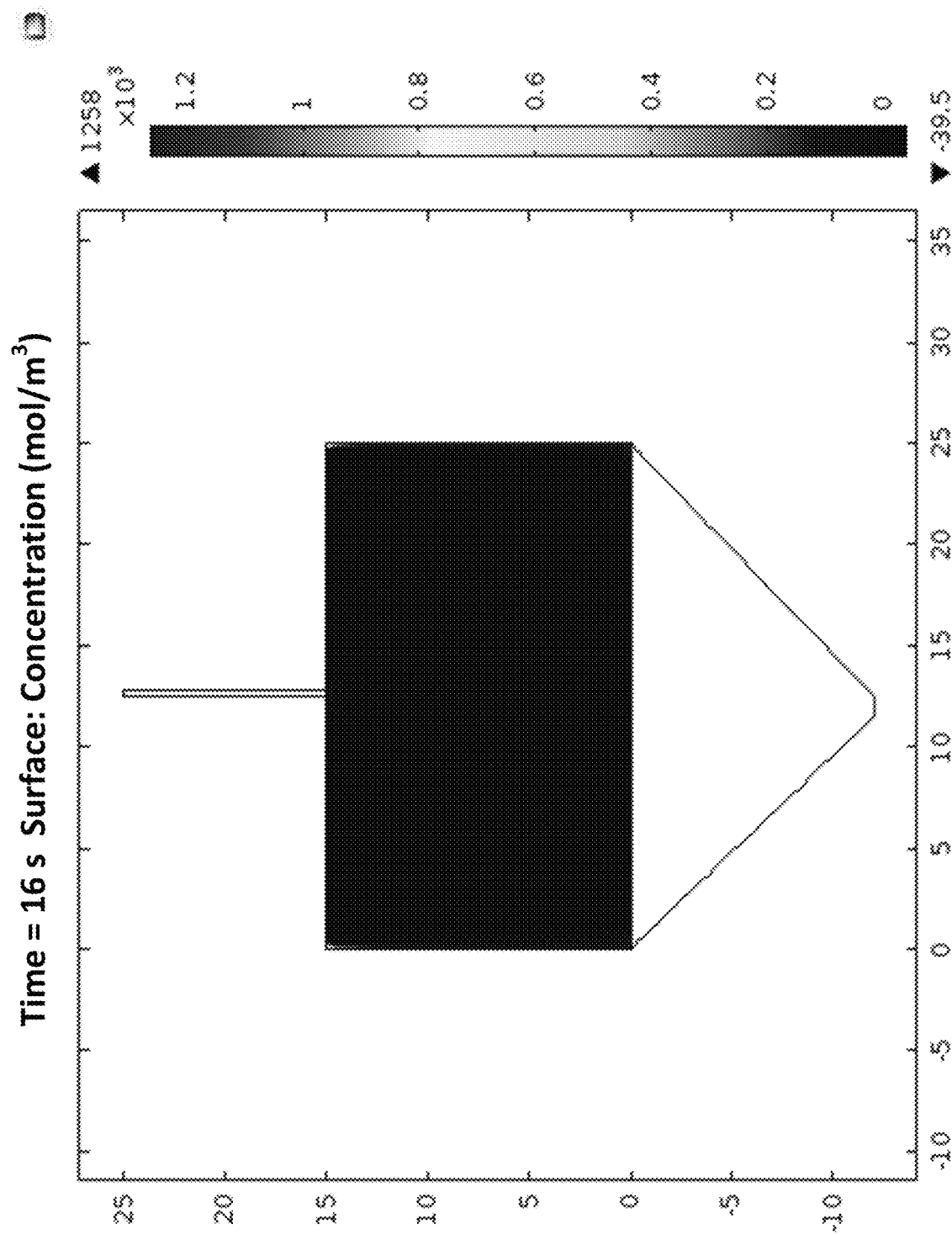
Figure 20J:
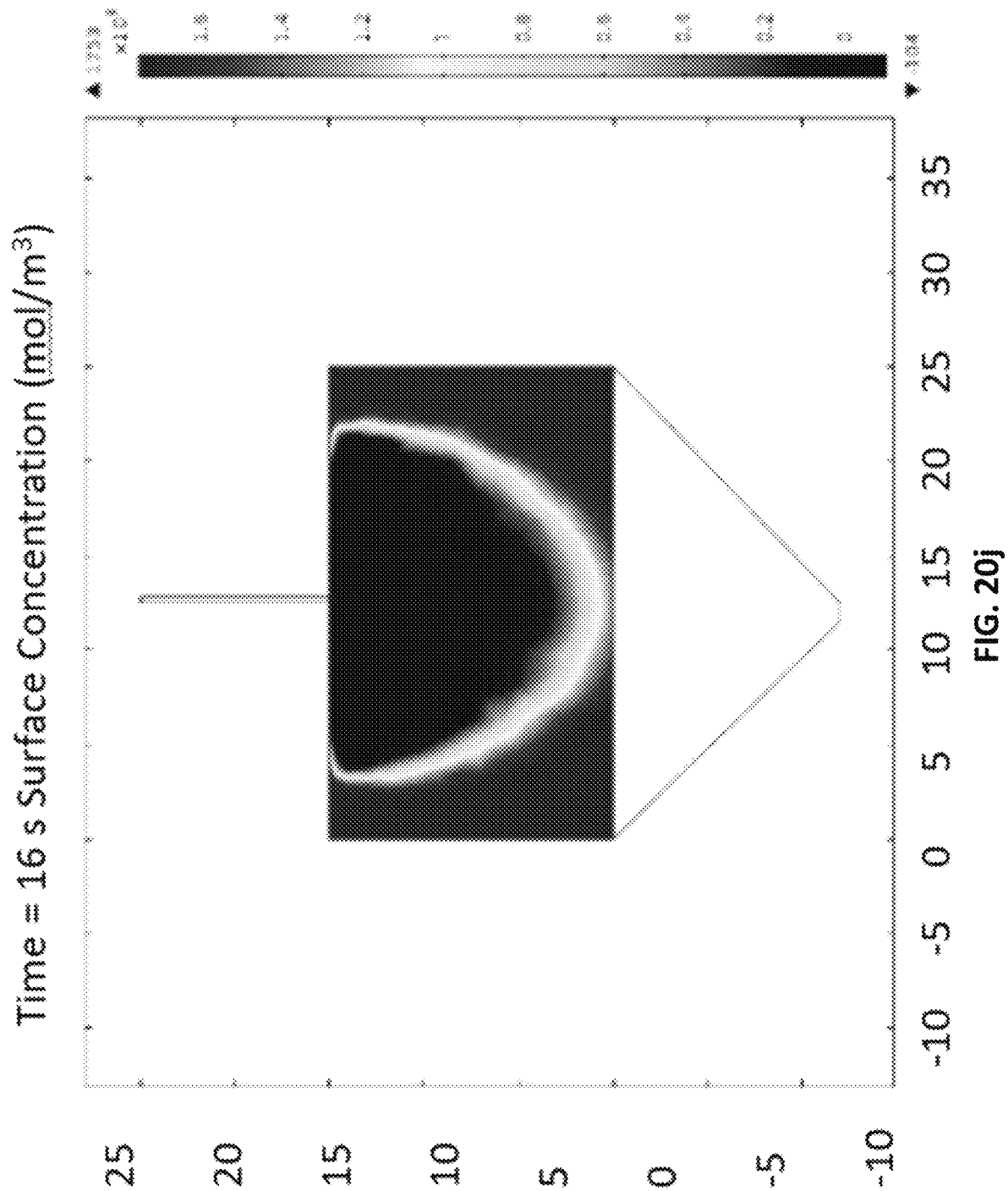
Figure 20K:
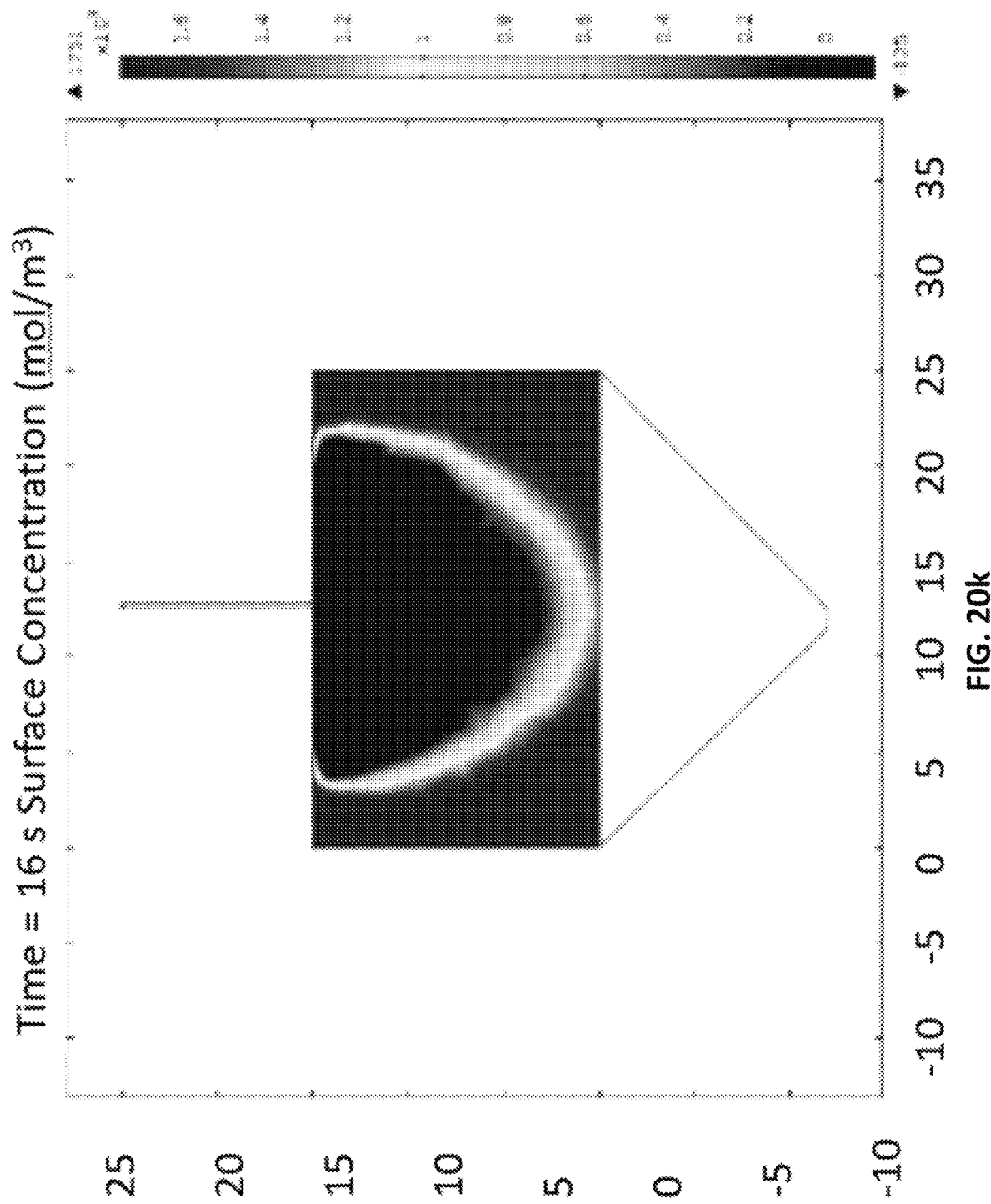
Figure 20I:
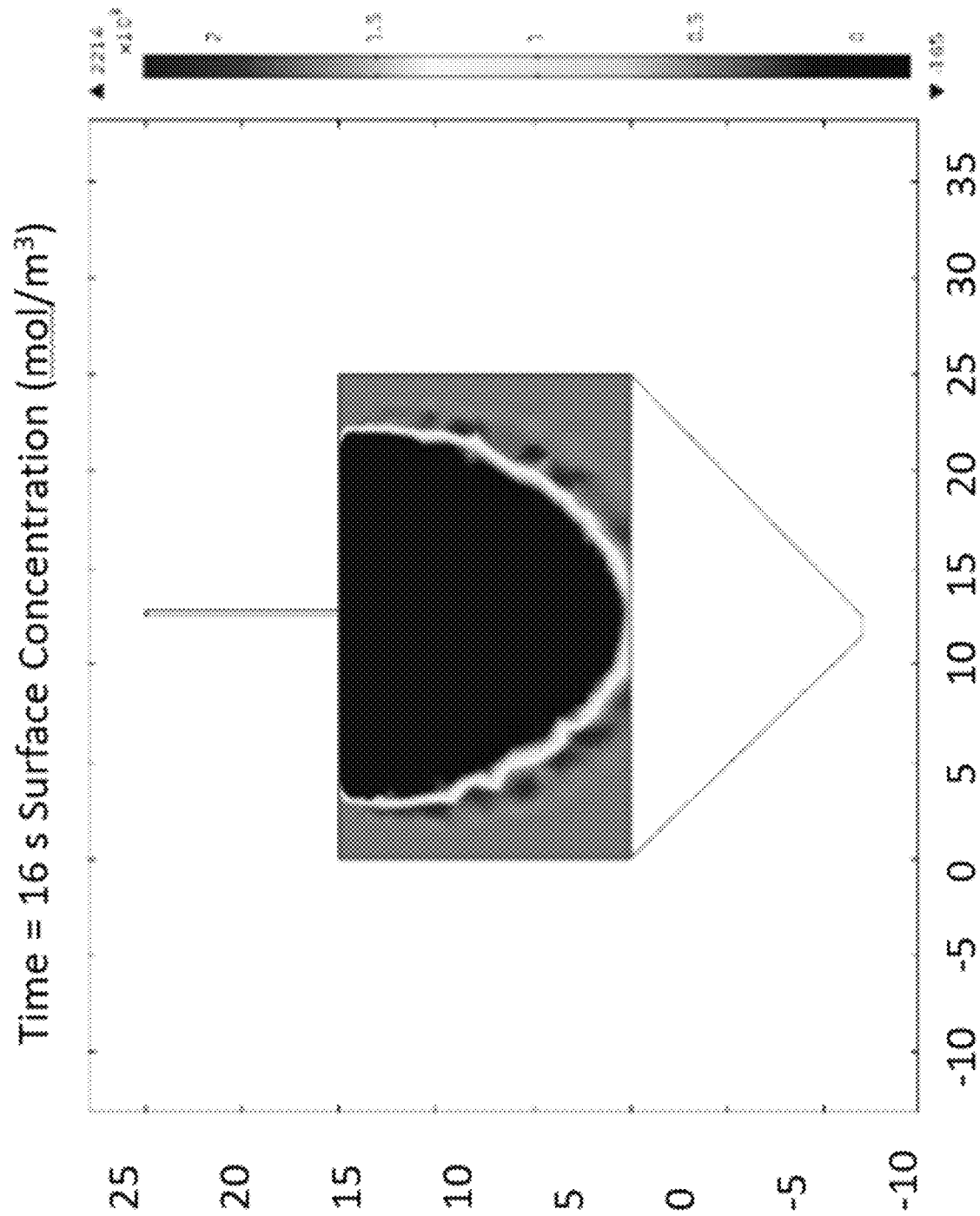
Figure 20M:
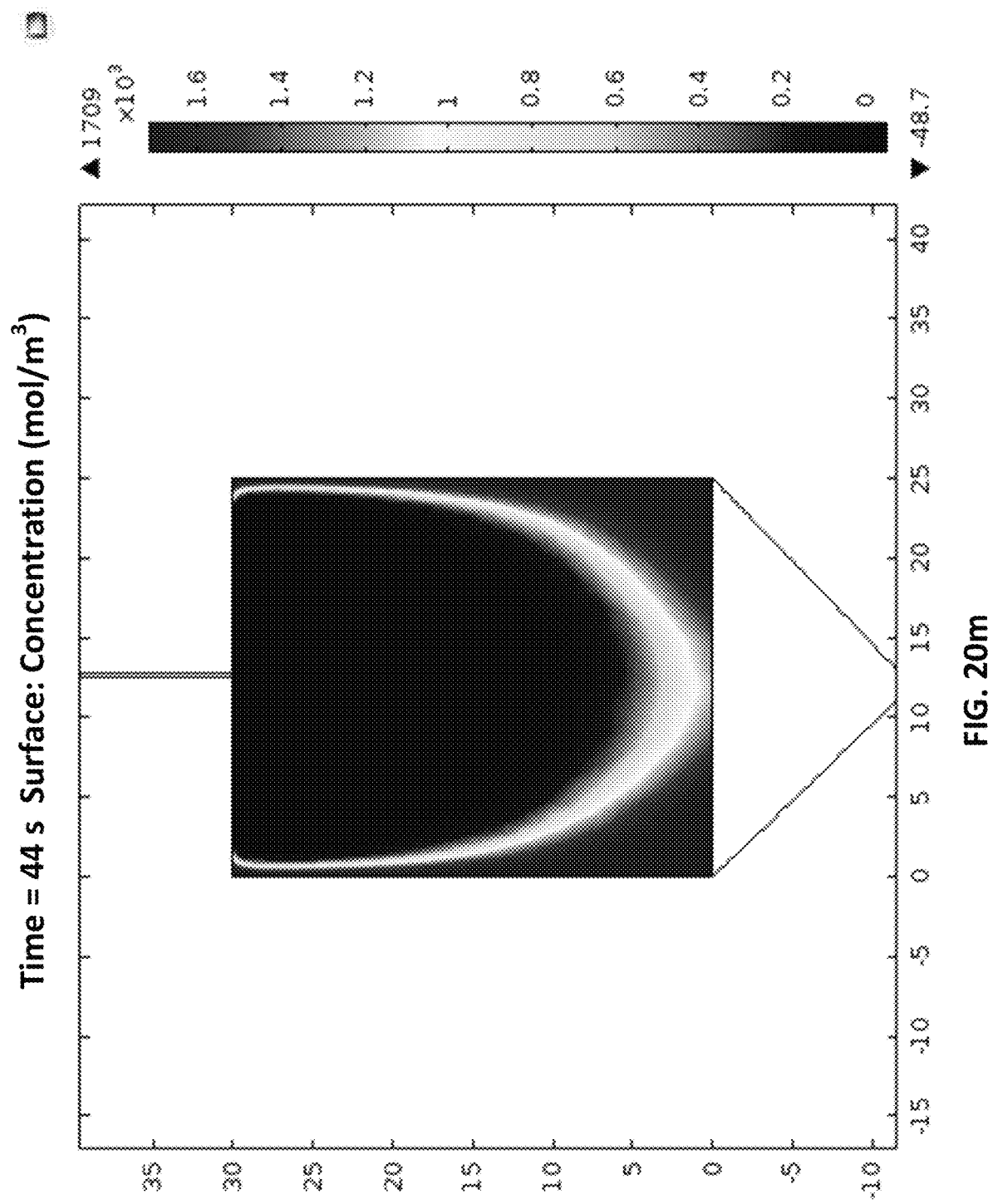
Figure 20N:
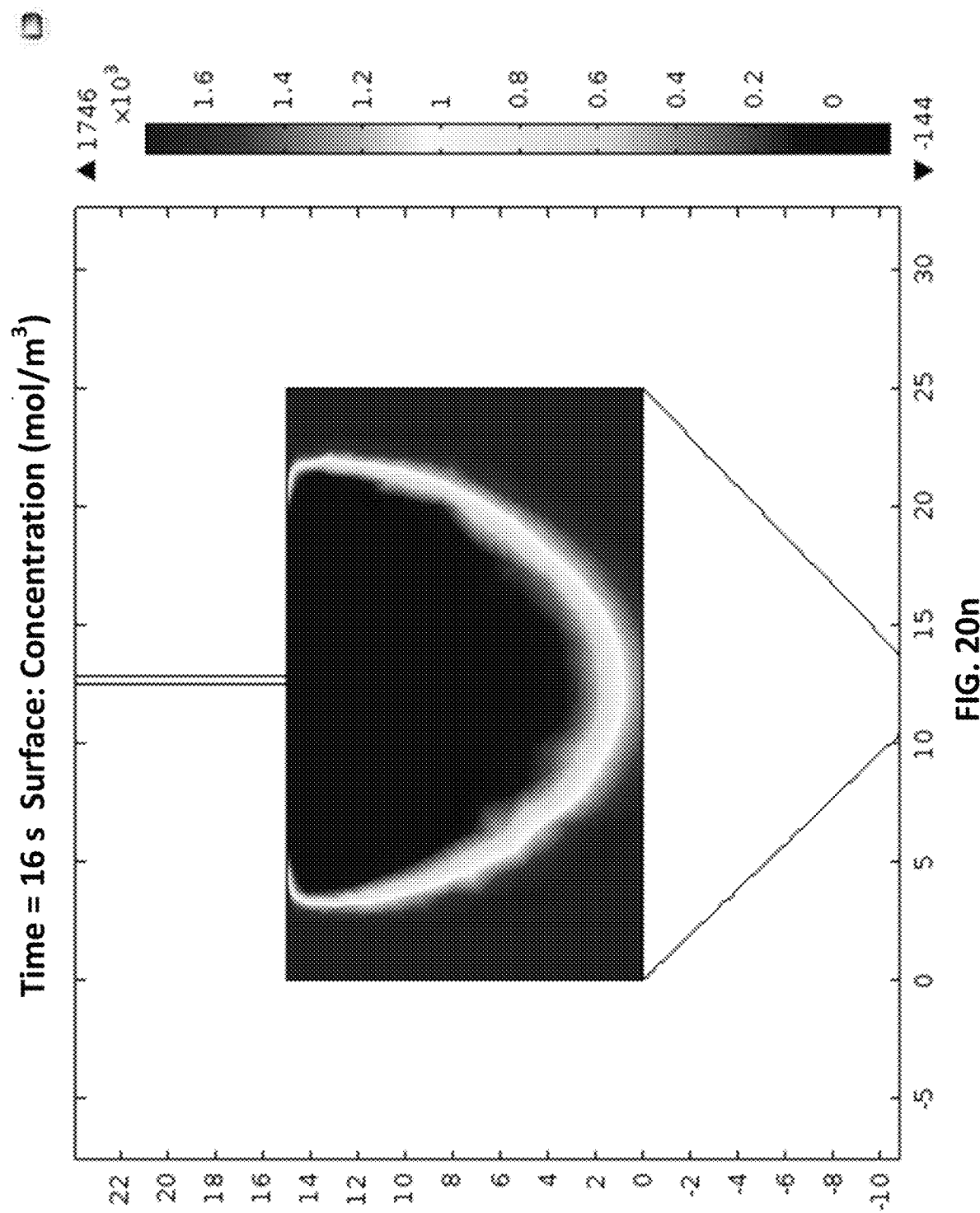
Figure 20O:
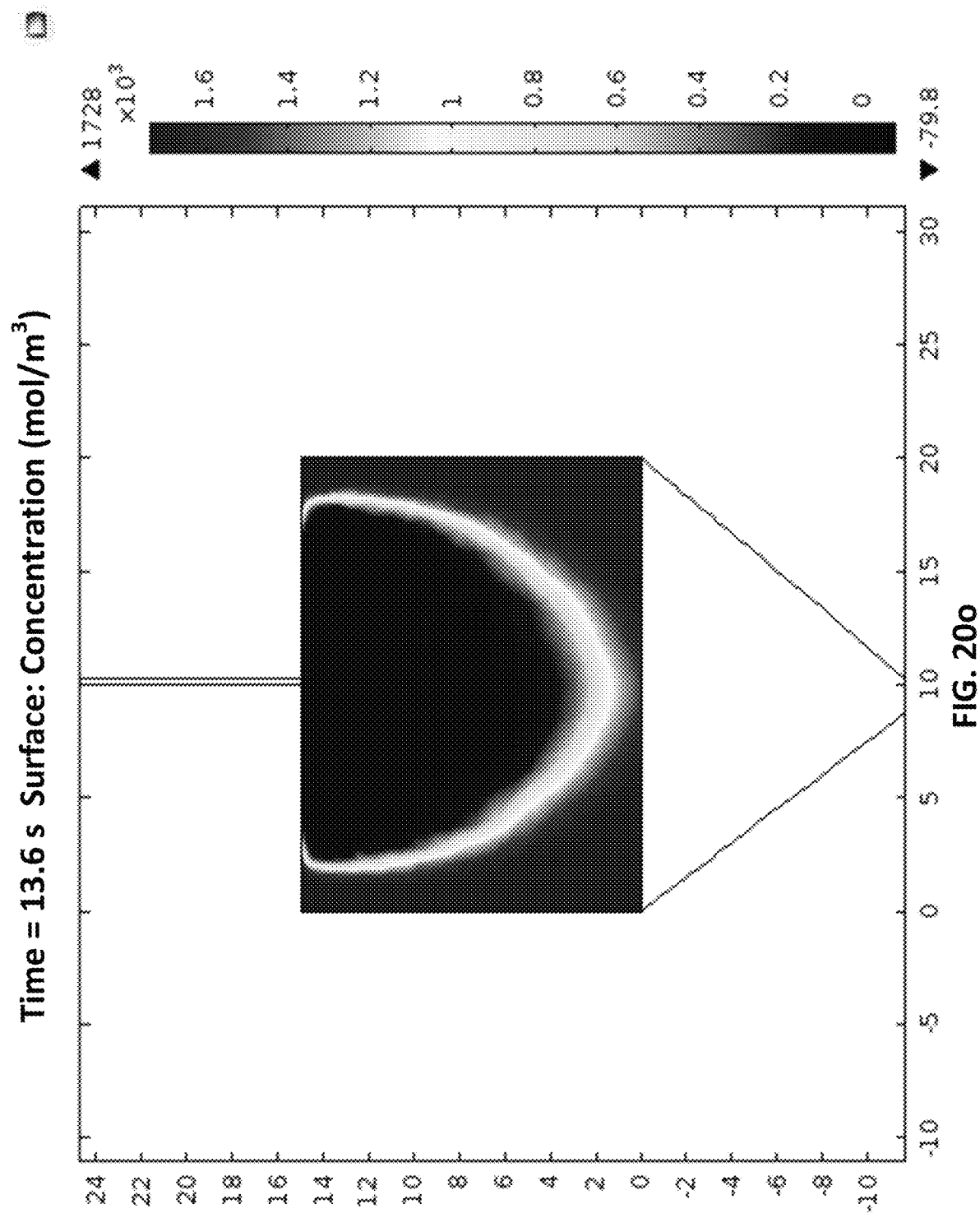

Example 19: Results and Discussion—Sensor's Extraction Membrane and Continuous Use for Quantification of Samples As illustrated in FIGS. 20a-20o, models of the extraction membrane from the sensor can be built up to optimize geometries, chemical/physical design, and lifetime. Along this line, models with an extraction membrane chemically converting $NH_4+$ to $NH_3$ via an alkaline material or electrochemically generating alkaline material to convert $NH_4+$ to $NH_3$, or directly electrochemically converting $NH_4+$ to $NH_3$ can be utilized. Based on the model, it is concluded that the concentration of the incoming $NH_4^+$ does not affect the concentration profile of the alkaline material source (e.g. stationary hydroxide ($OH^-$) sites) when the concentration range of $NH_4^+$ is 3.6-100.0 mM, which is typically the encountered concentration in urine samples. In other words, the concentration of alkaline material in the chemical extraction membrane is primarily affected by the inlet velocity, which is a parameter modeled as variable of boundary conditions (e.g. inlet velocity $u_0$). In addition, the model enables to know the number of times the chemical extraction membrane can be used consecutively before the chemical alkaline material ($OH^-$) is depleted. Embodiments such as the CODA device illustrated in FIG. 19 can be modeled assuming the sensor has a source of alkaline material that will be depleted after each use. FIGS. 20a-20o also show how different variables in the extraction membrane can be tested. These variables include porosity, boundary conditions, initial $NH_4^+$ concentration of the samples and geometry. All the variables can be analyzed, allowing a determination of how they affect the extraction membrane's alkaline material concentration profile.

Figure 21A:
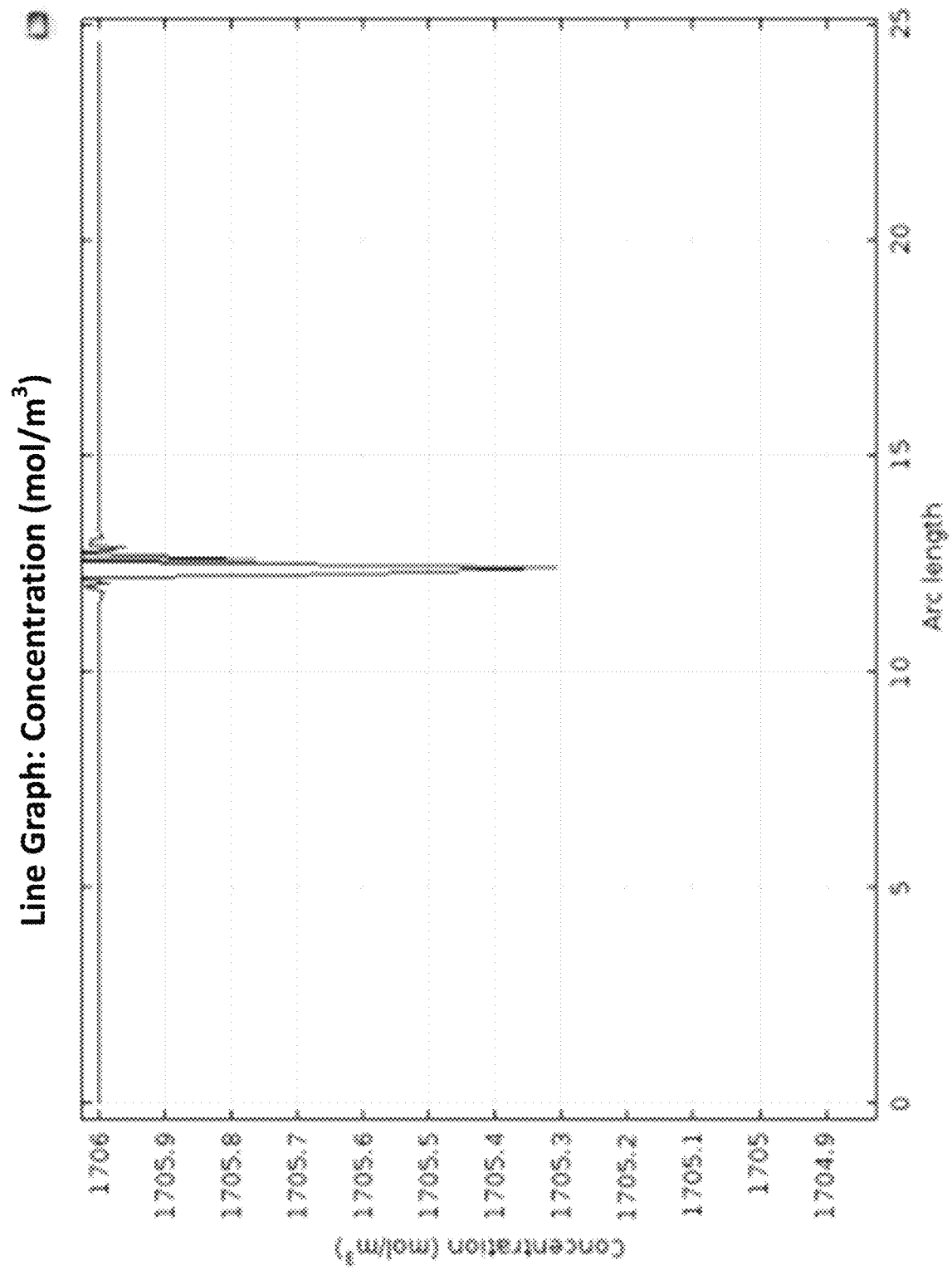
FIGS. 21a and 21b are model results of the cross-section concentration profile of the alkaline material in a chemical extraction membrane, after the first cycle (FIG. 21a) and after the $20^{th}$ cycle (FIG. 21b).
Figure 21B:
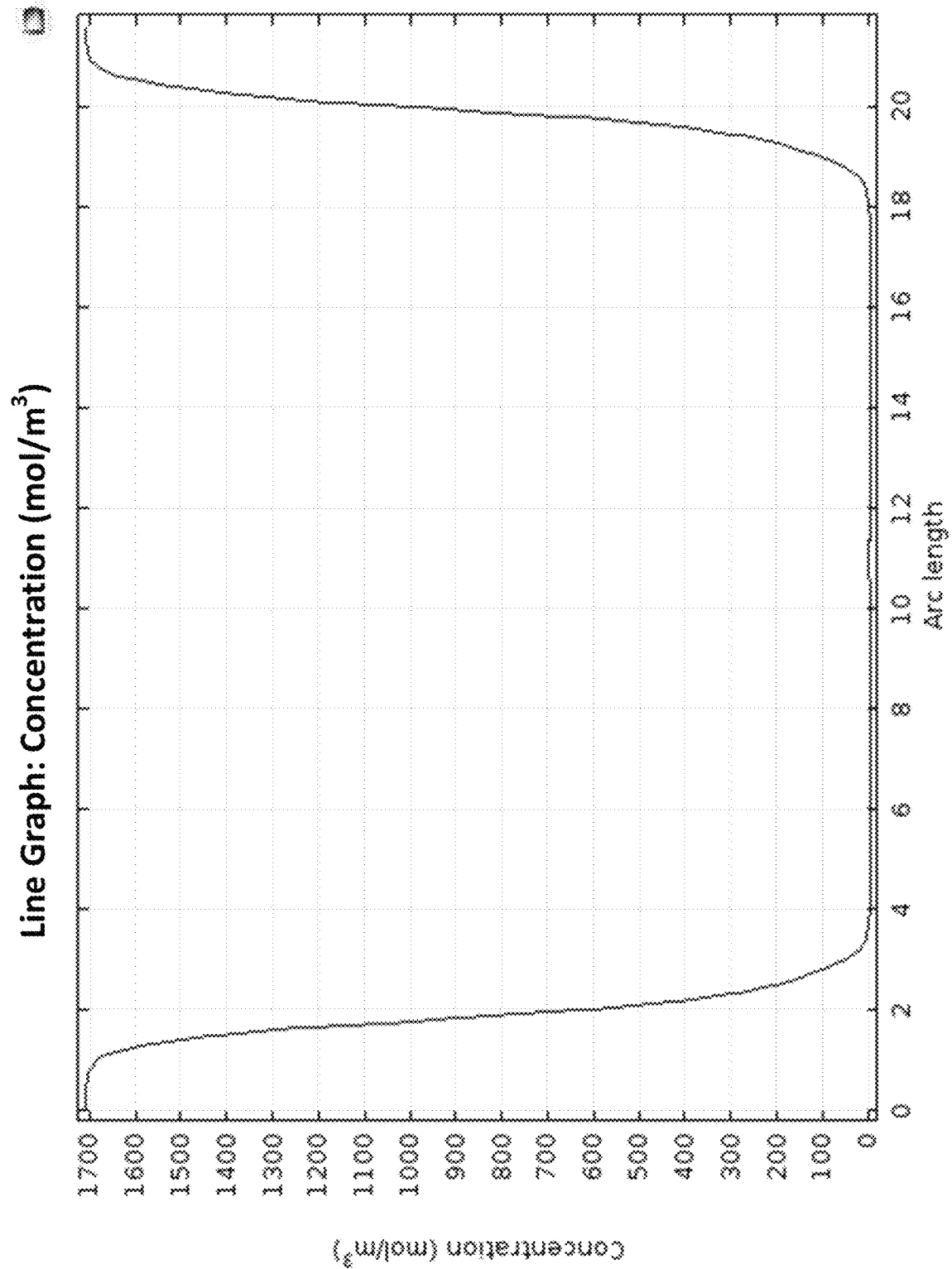

As example, FIGS. 21a and 21b show the model result of the cross section concentration profile of the alkaline material in a chemical extraction membrane, after the first cycle (shown in FIG. 21a) and after the $20^{th}$ cycle (shown in FIG. 21b).

In addition, other design aspects of the extraction membrane are important. One of them is the elimination of potential ammonia leaks. Based on practice and simulations, multiple but narrow liquid paths, and lower exposed area to liquid/air interfaces minimize the ammonia gas leakage from the membrane. Furthermore, additional modification of the extraction membrane with potential agents for chelating amine groups, eliminate interference from the non-enzymatic decomposition of primary amine group molecules that may render ammonia not originally present in the sample, and therefore, non-physiologically relevant. This modification eliminates problems of overestimation of ammonia (FIG. 22a) which is known to be a problem under state-of-the-art testing conditions (FIG. 23). In fact, the combinations of all above-mentioned factors, render an extraction membrane with high specificity, as shown in FIGS. 22a and 22b.

FIGS. 20a-20o show examples of how different variables: porosity, boundary conditions, initial $NH_4^+$ concentration in the sample and geometry affect the concentration profile of the alkaline material in the extraction membrane. The concentration of $NH_4^+$, the inlet velocity and the porosity were set to values of 37.8 mM, 0.05 m $s^{-1}$ and 0.34, respectively. The result shown here is concentration profile for the (FIG. 20a)$1^{th}$, (FIG. 20b) $10^{th}$, and (FIG. 20c)$20^{th}$ measurement. The concentration of $NH_4^+$ and the inlet velocity were set to values of 37.8 mM and 0.05 in $s^{-1}$, respectively. The result shown here is the $20^{th}$ measurement with porosity of: (FIG. 20d) 0.34, (FIG. 20e) 0.66, and (FIG. 20f) 0.90. The concentration of $NH_4^+$ and the porosity are set to values of 37.8 mM and 0.34. The result shown here is the $20^{th}$ measurement with inlet velocity of: (FIG. 20g) 0.0035 m $s^{-1}$, (FIG. 20h) 0.05 m $s^{-1}$, and (FIG. 20i) 0.5 m $s^{-1}$. The inlet velocity of the sample and the porosity was set to the values of 0.05 m $s^{-1}$ and 0.34, respectively. The result shown here is the $20^{th}$ measurement with $NH_4^+$ concentrations of: (FIG. 20j) 37.8 mM, (FIG. 20k) 100.0 mM, and (FIG. 20l) 3780.0 mM. The concentration of $NH_4^+$ and the porosity were set to the values of 37.8 mM and 0.34, respectively. The result shows the concentration profile how the hydroxide ($OH^-$) is depleted with the configuration of: (FIG. 20m) 3 cm in length and 2.5 cm in diameter, (FIG. 20n) 1.5 cm in length and 2.5 cm in diameter, and (FIG. 20o) 1.5 cm in length and 2.0 cm in diameter.

Figure 22A:
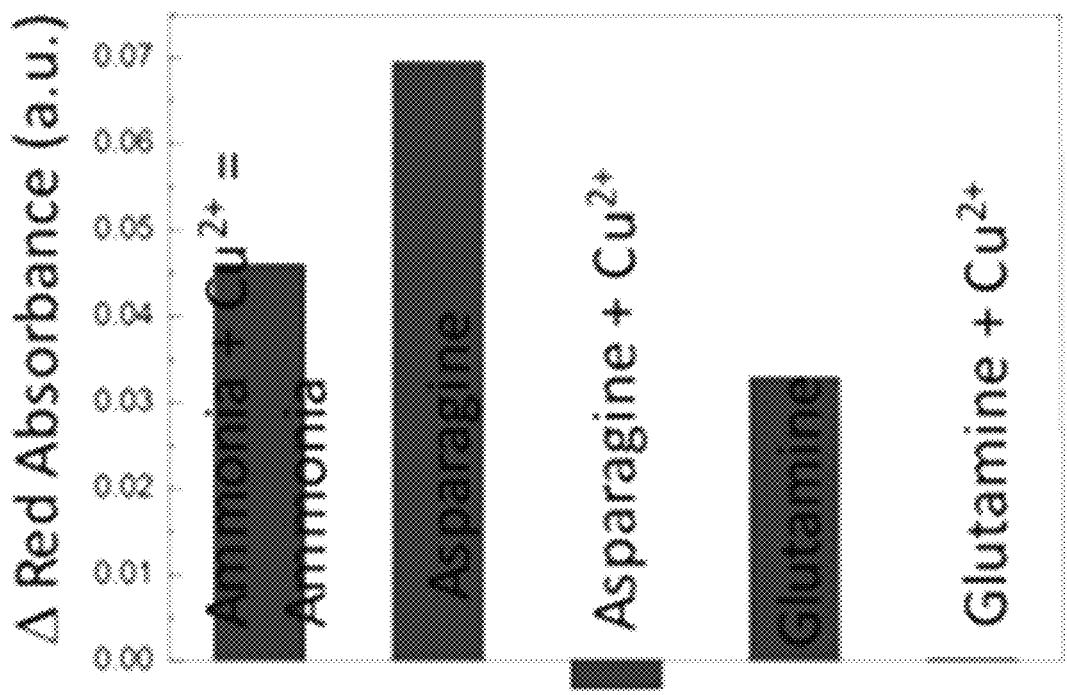
FIGS. 22a and 22b illustrate the analytical performance of the extraction membrane and overall sensor for complex body fluids.
Figure 22B:
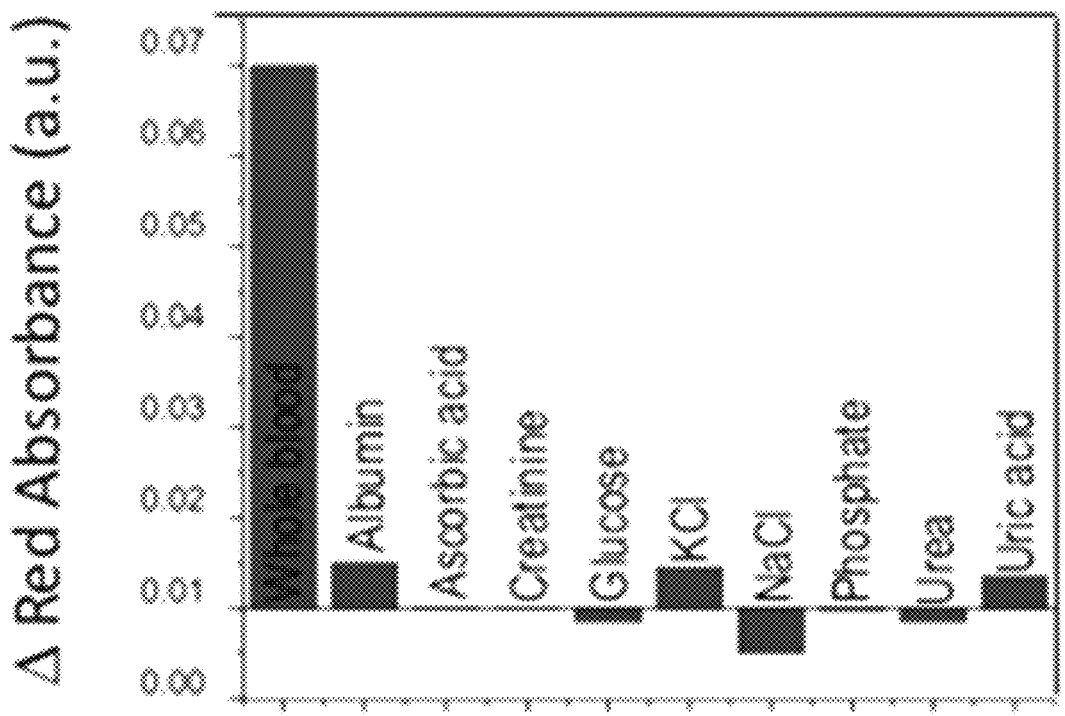
Figure 23:
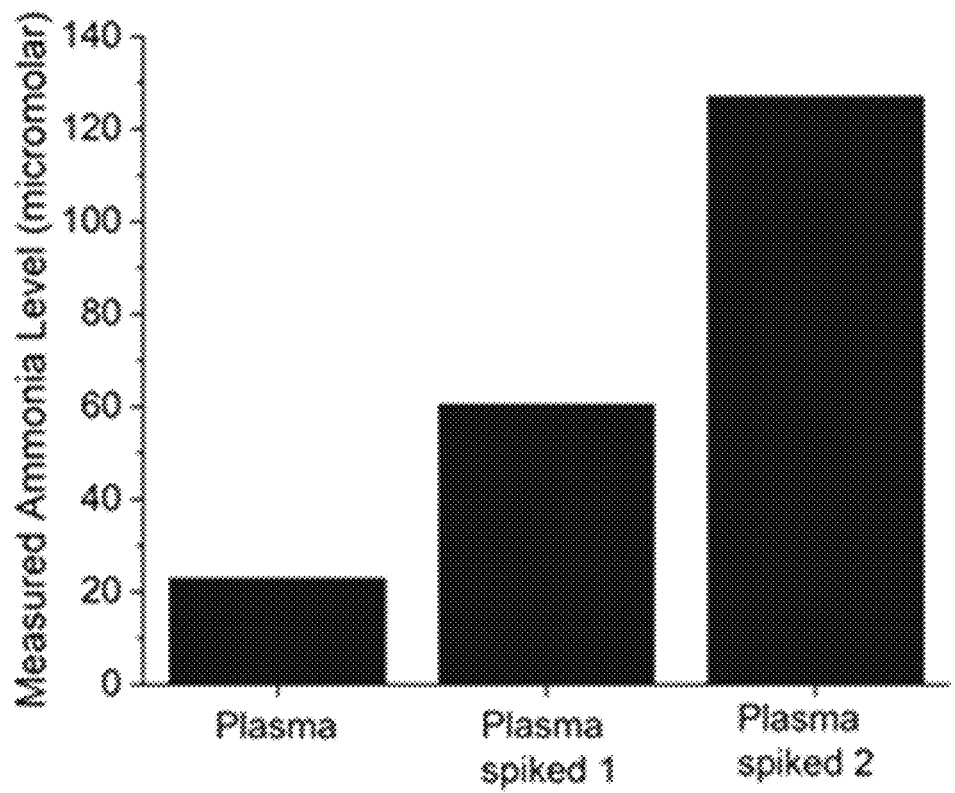
FIG. 23 shows the results of ammonia measured by a reference enzymatic method on three samples with interference from amino acids.

FIGS. 22a and 22b illustrate the analytical performance of the extraction membrane and overall sensor for complex body fluids. In FIG. 22a the fluid was treated with a copper ion chelating material; these copper ions chelate (bind) with the amine groups of amino acids and the primary amine residues in other molecules thus preventing them from enzymatic and non-enzymatic degradation which (degradation of these molecules produces falsely increased ammonia levels). FIG. 22b) shows the overall selectivity of the extraction membrane in the sensor to whole blood with 170 uM ammonia (as ammonium). FIG. 22b) shows that the extraction membrane and sensor has negligible response to maximum known concentrations of other blood components: 5,000 mg/dL albumin, 3 mg/dL ascorbic acid, 5 mg/dL creatinine, 2656 mg/dL glucose, 370 mg/dL, (5 mM) potassium ion, 228 mg/dL (3.9 mM) sodium ion, 1,000 mg/dL phosphate, 107 mg/dL urea, and 6.8 mg/dL uric acid.

FIG. 23 shows the response of an enzymatic reference method (Roche Cobas®) to plasma as taken from the body, plasma spiked 1 (spiked with glutamine), plasma spiked 2 (with added amino acids glutamine, L-arginine, L-asparagine and creatinine, urea—ammonia metabolism products). Concentrations of spiking agents range from 10-100s µM levels—simulating physiologically expected levels. This demonstrates that enzymatic methods are confounded by spontaneous, non-enzymatic deamination of the amino acids which results in excessively high ammonia reading.

Figure 24:
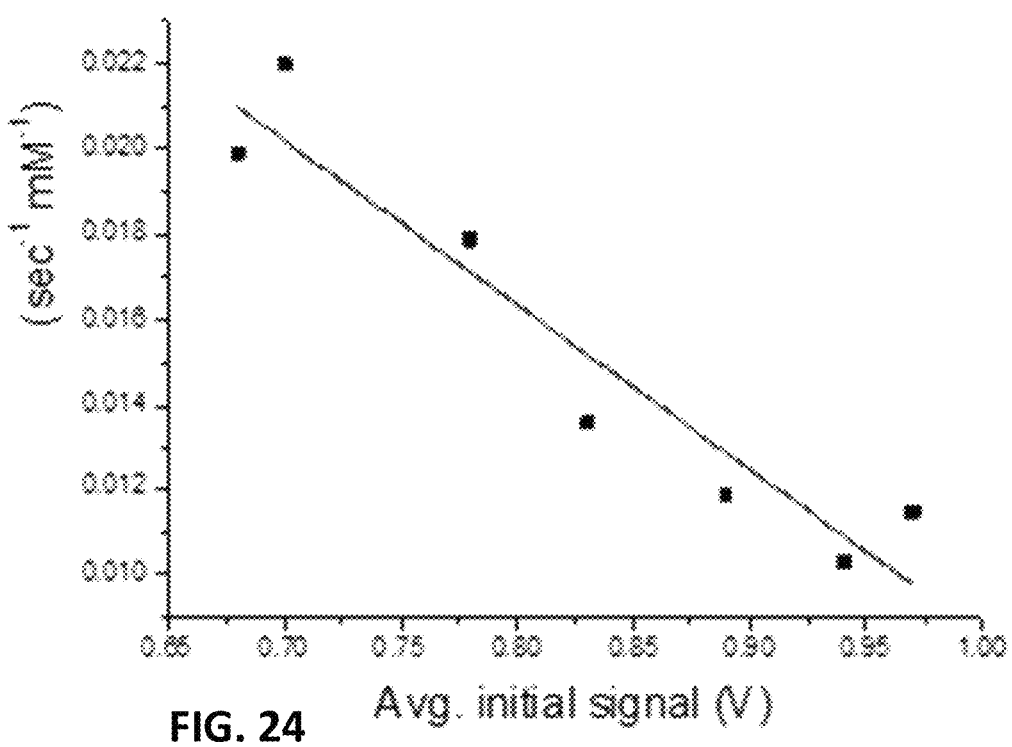
FIG. 24 shows a demonstration of quantifiable generic sensors sensitivity that enable calibration free strategies for quantification of ammonia.

Example 20: Results and Discussion—Sensor Use with Free Calibration for Quantification of Ammonia Intelligent algorithms can be built based on quantified generic sensor sensitivity and used as means of avoiding sensor calibration (either every time before the sensor use or device and sensor used). The intelligent algorithms are fed with physical/chemical behaviors such as the sensor sensitivity for different sensor's initial working conditions, such the initial signal (V) before analyte sensing. FIG. 24 shows a demonstration of quantifiable generic sensors sensitivity that enable calibration free strategies for quantification of ammonia.

FIG. 24 illustrates the relation between the measured initial signal from the sensing area of different sensors with the slope of the sensor's corresponding calibration curves ranging from 3.6 mM to 18.6 mM. The relation between these two variables is linear with the regression coefficient is $R^2=0.88$. This linear relation can help to build the calibration free intelligent algorithm for quantification of ammonia.

Figure 25:
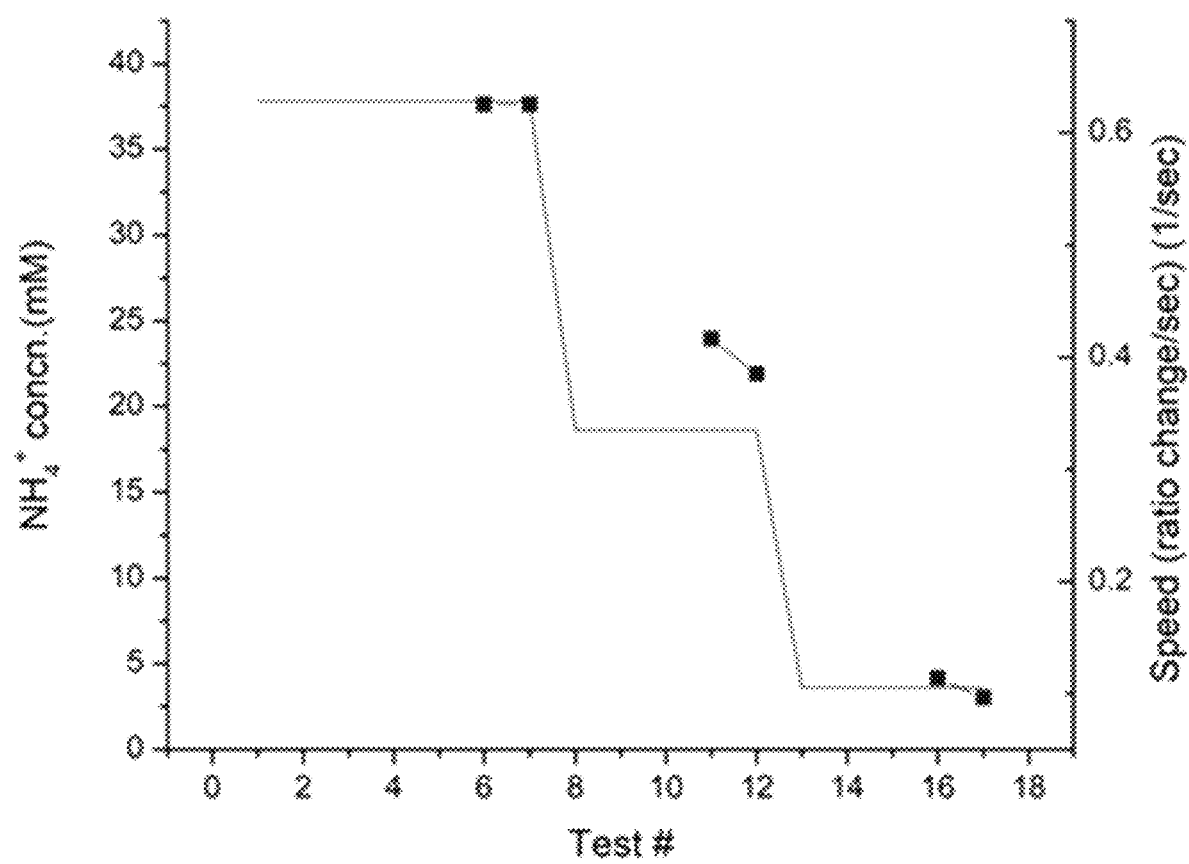
FIG. 25 shows a continuous measurement from 37.6 mM to 3.6 mM of $NH_4^+$.

Example 21: Results and Discussion—Sensor Use for Continuous Quantification of Ammonia with High Accuracy FIG. 25 shows a continuous measurement from 37.6 mM to 3.6 mM of $NH_4^+$, which matches the actual ammonia concentration with errors smaller than <15%. As illustrated in FIG. 25, the applications described above can lead to successful continuous quantification of ammonia with small differences between the measured ammonia value by the sensor from this application, and the true ammonia concentration. The "Speed" is a parameter defined for CODA used to quantify the $NH_4^+$ concentration.

While the present disclosure has been discussed in terms of certain embodiments, it should be appreciated that the present disclosure is not so limited. The embodiments are explained herein by way of example, and there are numerous modifications, variations and other embodiments that may be employed that would still be within the scope of the present disclosure.

What is claimed is:

1. A cartridge comprising:
a distributor layer configured to receive a sample of a bodily fluid comprising ammonium ($NH_4^+$);
an alkaline layer in contact with the distributor layer and configured to convert at least a portion of the ammonium ($NH_4^+$) into ammonia ($NH_3$);
a hydrophobic layer in contact with the alkaline layer and configured to dispel at least a portion of the ammonia ($NH_3$); and
an indicator layer configured to change color in response to an amount of the ammonia ($NH_3$).

2. The cartridge of claim 1, wherein the distributor layer comprises a filter.

3. The cartridge of claim 1, wherein the alkaline layer comprises at least one of organic hydroxide, sodium hydroxide, and buffer at pH 10 or higher.

4. The cartridge of claim 1, wherein the alkaline layer comprises polyethylene (PE) film.

5. The cartridge of claim 1, wherein the hydrophobic layer comprises polytetrafluoroethylene, polytetrafluoroethylene derivative or a cellulose derivative.

6. The cartridge of claim 1, wherein the indicator layer comprises a filter paper.

7. The cartridge of claim 1, wherein the indicator layer comprises at least one of bromophenol blue, bromothymol blue, and a plant-based pH indicator.

8. An analyzer comprising:
a cartridge comprising:
a distributor layer configured to receive a sample of a bodily fluid comprising ammonium ($NH_4^+$);
an alkaline layer in contact with the distributor layer and configured to convert at least a portion of the ammonium ($NH_4^+$) into ammonia ($NH_3$);
a hydrophobic layer in contact with the alkaline layer and configured to dispel the ammonia ($NH_3$); and
an indicator layer configured to change in color in response to a quantity of the ammonia ($NH_3$); and
a sensor comprising:
at least one light emitting diode configured to illuminate the indicator layer;
at least one photodiode configured to measure absorbance changes of the indicator layer; and
a processor configured to at least one of: quantify the amount of the ammonia ($NH_3$) based on the absorbance changes, identify relative changes in the quantified amount of ammonia ($NH_3$) over time.

9. The analyzer of claim 8, wherein the processor is further configured to detect at least one of altered organ function, altered tissue function, and altered metabolic status based on the quantified amount of ammonia ($NH_3$) or the relative changes in the quantified amount of ammonia ($NH_3$) over time.

10. The analyzer of claim 8, further comprising a user interface device configured to receive at least one transmission of information from the sensor, the user interface device having a display including a graphical user interface, wherein the graphical user interface is configured to display the information.

11. The analyzer of claim 10, wherein the information corresponds to at least one of the quantified amount of the ammonia ($NH_3$) and the identified relative changes.

12. The analyzer of claim 8, wherein the at least one light emitting diode emits light at the maximum absorption wavelength of the indicator layer, and another of the at least one light emitting diode emits light at the minimum absorption wavelength of the indicator layer.

* * * * *